US012508405B2

(12) United States Patent
Fell et al.

(10) Patent No.: US 12,508,405 B2
(45) Date of Patent: Dec. 30, 2025

(54) SURGICAL METHOD, DEVICE, SYSTEM AND KIT FOR THE TREATMENT OF HYDROCEPHALUS

(71) Applicant: The Penn State Research Foundation, University Park, PA (US)

(72) Inventors: Barry M. Fell, Hummelstown, PA (US); Randy S. Haluck, Lititz, PA (US); Sprague W. Hazard, III, Hummelstown, PA (US); Elias B. Rizk, Harrisburg, PA (US)

(73) Assignee: The Penn State Research Foundation, University Park, PA (US)

( * ) Notice: Subject to any disclaimer, the term of this patent is extended or adjusted under 35 U.S.C. 154(b) by 359 days.

(21) Appl. No.: 17/914,399

(22) PCT Filed: Mar. 24, 2021

(86) PCT No.: PCT/US2021/023908
§ 371 (c)(1),
(2) Date: Sep. 26, 2022

(87) PCT Pub. No.: WO2021/195225
PCT Pub. Date: Sep. 30, 2021

(65) Prior Publication Data

US 2023/0310816 A1 Oct. 5, 2023

Related U.S. Application Data

(60) Provisional application No. 62/993,988, filed on Mar. 24, 2020.

(51) Int. Cl.
*A61M 27/00* (2006.01)
*A61B 17/16* (2006.01)

(52) U.S. Cl.
CPC ....... *A61M 27/006* (2013.01); *A61B 17/1695* (2013.01)

(58) Field of Classification Search
CPC .............. A61M 1/1601; A61M 1/3609; A61M 2205/3331; A61M 1/1613; A61M 1/341;
(Continued)

(56) References Cited

U.S. PATENT DOCUMENTS 9,402,982 B2 8/2016 Baert et al.
9,737,697 B2 8/2017 Heilman et al.
(Continued)

FOREIGN PATENT DOCUMENTS

WO 9633766 A1 10/1996
WO 2020198289 A1 10/2020

OTHER PUBLICATIONS

Sharkey, Paul, Ventriculosagittal-Sinus Shunt, Journal of Neurosurgery, Publication dated May 11, 1964, pp. 362-367.
(Continued)

*Primary Examiner* — Leslie R Deak
(74) *Attorney, Agent, or Firm* — Dinsmore & Shohl LLP

(57) ABSTRACT

Methods, devices, systems, and/or kits that encompass various components for accessing cerebrospinal fluid (CSF) in a CSF containing space of a subject to drain the CSF into a dural venous sinus (DVS) of the subject via a single cranial hole are disclosed herein. The described methods, devices, systems and/or kits drain the CSF into the DVS to treat hydrocephalus in a manner that does not require penetration into the gray matter of the subject's brain.

6 Claims, 37 Drawing Sheets

(58) Field of Classification Search
CPC ...... A61M 2205/3327; A61M 2205/50; A61M 2205/52; A61M 2230/205; A61M 2230/30; A61M 2230/42; A61M 2230/50; A61M 1/3403; A61M 1/1615
See application file for complete search history.

(56) References Cited

U.S. PATENT DOCUMENTS

| | | | |
|---|---|---|---|
| 2003/0199831 | A1 | 10/2003 | Morris et al. |
| 2005/0059922 | A1 | 3/2005 | Kuhlman et al. |
| 2005/0085764 | A1 | 4/2005 | Borgesen |
| 2008/0195178 | A1 | 8/2008 | Kuzma |
| 2014/0073859 | A1 | 3/2014 | Schorn |
| 2015/0165166 | A1 | 6/2015 | Gill et al. |
| 2017/0119527 | A1 | 5/2017 | Chavez et al. |
| 2018/0256866 | A1 | 9/2018 | Malek et al. |
| 2019/0030322 | A1 | 1/2019 | Schulte et al. |

OTHER PUBLICATIONS

Baert, Edward Jozef, Treating Hydrocephalus with Retrograde Ventriculosinus Shunt: Prospective Clinical Study, www. sciencedirect. com; Oct. 2018, 9 pages.

Børgesen, Svend Erik, Shunting to the cranial venous sinus using the SinuShunt, Childs Nerv Syst (2004) 20:397-404 DOI 10.1007/ s00381-004-0914-6, pp. 397-404.

El-Shafei, Ismail L., The retrograde ventriculosinus shunt: concept and technique for treatment of hydrocephalus by shunting the cerebrospinal fluid to the superior sagittal sinus against the direction of blood flow, Child's Nerv Syst (2001) 17:457-465 DOI 10.1007/ s003810100456, p. 457-465.

Taylor, Joshua, Development of a computational model for macroscopic predictions of device-induced thrombosis, Biomech Model Mechanobiol (2016) 15:1713-1731 DOI 10.1007/s10237-016-0793-2.

Toma, Ahmed K., Ventriculosinus shunt, Received: Jun. 16, 2009 / Revised: Nov. 2, 2009 / Accepted: Jan. 2, 2010 / Published online: Feb. 23, 2010, Neurosurg Rev (2010) 33:147-153.

SURGICAL METHOD, DEVICE, SYSTEM AND KIT FOR THE TREATMENT OF HYDROCEPHALUS

CROSS-REFERENCE TO RELATED APPLICATIONS

This application is the U.S. National Stage of PCT/US2021/023908 filed on Mar. 24, 2021, which claims priority to U.S. Provisional Patent Application Ser. No. 62/993,988, filed Mar. 24, 2020. The present application is also related to U.S. Provisional Patent Application Ser. No. 62/823,223, filed Mar. 25, 2019. The entire content of both are incorporated herein by reference in their entirety.

TECHNICAL FIELD

The present disclosure generally relates to methods, devices, systems, and/or kits for the treatment of hydrocephalus, and more specifically, to methods, devices, systems and/or kits to drain cerebrospinal fluid (CSF) from a CSF containing space of a subject into a dural venous sinus (DVS).

BACKGROUND

Existing configurations for devices that are used to treat accumulation of excess fluid in a cranial space of a subject have attempted to address improved shunt designs, improved one-way valves, reduced catheter blockages, incorporate material improvements to reduce the occurrence of infections, or other variations in catheter (e.g., tube) systems to improve upon associated performance issues. However, such designs continue to suffer high failure rates from issues such as challenging surgical procedures to implant the catheters, too much or too little CSF fluid flow, susceptibility to periodic blockages or clots, infections, inadequate removal of excess fluid from any of the subarachnoid space or ventricles of the brain and drainage rates impacted by a change of subject position. Furthermore, concerns associated with existing and other proposed methods include the risk of significant bleeding, the risk of introducing air into the dural venous sinuses (e.g., potential embolism), and the inability to properly place a catheter in a CSF containing space.

SUMMARY

Various aspects of the present disclosure include methods, devices, systems, and/or kits that encompass various components for accessing cerebrospinal fluid (CSF) of a subject to drain the CSF into a dural venous sinus (DVS) of the subject via a single cranial hole. The methods, devices, systems and/or kits described herein drain the CSF into the DVS to treat hydrocephalus in a manner that may not require penetration into the gray matter of the subject's brain.

Additional features and advantages of the aspects described herein will be set forth in the detailed description which follows, and in part will be readily apparent to those skilled in the art from that description or recognized by practicing the aspects described herein, including the detailed description which follows, the claims, as well as the appended drawings.

It is to be understood that both the foregoing general description and the following detailed description describe various aspects and are intended to provide an overview or framework for understanding the nature and character of the claimed subject matter. The accompanying drawings are included to provide a further understanding of the various aspects, and are incorporated into and constitute a part of this specification. The drawings illustrate the various aspects described herein, and together with the description serve to explain the principles and operations of the claimed subject matter.

DETAILED DESCRIPTION

Figure 1B:
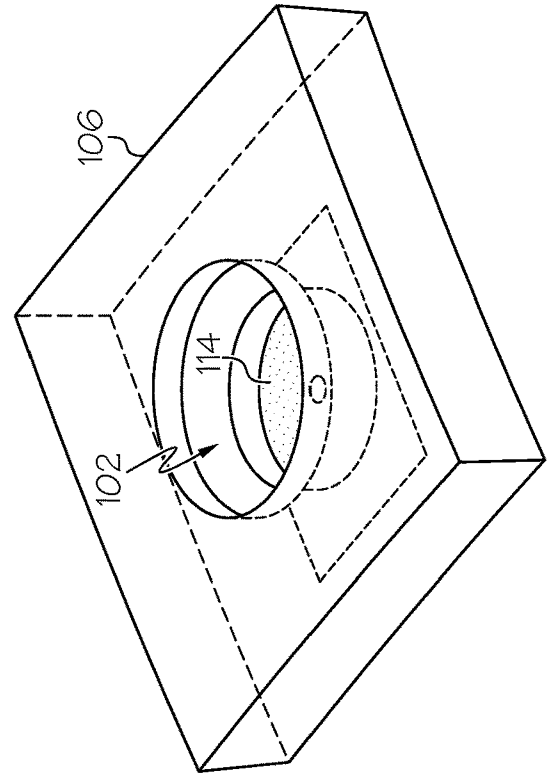
FIG. 1B depicts a perspective view of the illustrative DVS burr hole of FIG. 1A, according to one or more aspects shown and described herein.

Aspects of the present disclosure relate to methods, devices, systems, and/or kits for accessing a CSF containing space in a subject, and more particularly, to methods, devices, systems, and/or kits to drain cerebrospinal fluid (CSF) from a CSF containing space into the dural venous sinuses (DVS) (alternatively referred to as cerebral venous sinuses) in such a manner that does not cause penetration into the gray matter or other vital portions of the brain.

In various aspects, the devices and/or systems described herein are modular in nature. Accordingly, each modular device and/or system may be individually serviceable and/or individually replaceable (e.g., internal components such as an integrated drain that is substituted for a larger size or a pressure/check-valve spring for a higher/lower spring rate, or the addition or change of a pressure, volume flow, or patient position recording device). Methods described herein permit such servicing and/or replacing of the modular devices and/or systems without penetration of the gray matter of the brain. For example, if it is determined that an infection is present in either of an intrathecal or other CSF (e.g. lateral ventricle, cisterna magna, spinal column, etc.) space (CSF source) and/or an intravascular space (DVS), only one or more than one device portion needing changed may be replaced without replacing the entire device. Similarly, only one or more than one system portion needing changed may be replaced without replacing the entire system. Such an approach to remedying an infection or blockage is a less invasive approach that further limits the risk of unnecessarily penetrating the gray matter of the brain (e.g., where the proximal portion (CSF source) of the system is located in the lateral ventricle and is functioning properly).

As indicated, the present disclosure is related to U.S. Provisional Patent Application Ser. No. 62/823,223 (the "'223 application"), the entirety of which is incorporated by reference herein. The '223 application disclosed symmetrically-shaped cranial implants (e.g., SAS implant plug, DVS implant plug, and/or the like) in close proximity to one another. For example, each respective cranial implant could fit into a respective standard craniometry opening (e.g., of circular shape, approximately 14 mm in diameter, drilled via the disclosed guide device). While aspects of the present disclosure may utilize a single standard craniometry opening (FIG. 1A. e.g., DVS burr hole 102, of circular shape, approximately 14 mm in diameter), cranial implants of the present disclosure are not limited by the size and/or shape of a cranial opening. Accordingly, the devices and/or systems of the present disclosure may be readily used when an existing cranial opening is not a standard shape and/or size, as described herein (FIGS. 4-11, e.g., not a standard opening, bone growth has occurred, and/or the like). Furthermore, the devices and/or systems of the present disclosure may be readily used when a new cranial opening needs further adjustment (e.g., laterally and/or the like) to be appropriately positioned (e.g., over a DVS).

The '223 application further disclosed modular implants. For example, a SAS implant plug and/or a DVS implant plug could be removed to service and/or replace a SAS inlet drain implant and/or a DVS outlet drain implant, respectively. While aspects of the present disclosure may include removal of the DVS implant anchor disclosed herein (e.g., FIG. 1A, DVS implant anchor 202), various aspects allow the DVS implant anchor to remain in place while the DVS implant disclosed herein (e.g., FIG. 12, DVS implant 1224) is replaced in its entirety. In such aspects, surrounding growth of new bone may remain undisturbed.

The '223 application further disclosed SAS implant plugs and/or DVS implant plugs generally configured to fit into burr holes (e.g., drilled using the guide device, generally 14 mm in diameter) and of a predetermined (e.g., fixed) thickness. Aspects of the present disclosure, as described more fully herein, accommodate for the eccentricity of a hole created by trephination of the skull. In one example, a conventional perforator bit may be used to create the burr hole. In another example, a multi flute burr may be used to create a custom burr hole into the skull (e.g., a custom entry point to the dura). In either example, since the devices and or systems of the present disclosure are not configured to fit any specifically shaped and/or sized burr hole, the devices and/or systems disclosed herein may flexibly adapt to any burr hole and/or cranial hole irrespective of the device used to drill the burr hole and/or cranial hole. Furthermore, aspects of the present disclosure, as described herein, include methods, materials (e.g., adhesives or compliant fibrous or sponge-like pads containing adhesive), devices, and/or systems to realize an adjustable depth (e.g., FIG. 12, DVS implant 1224 threads and DVS implant anchor 202 threaded portion 220, anchor 202 provided in kit form with a selection of vertically longer attachments (FIG. 2D-2F) to accommodate a thicker skull) to ensure positive contact with the dura to form a watertight seal (e.g., not a predetermined/fixed depth). Moreover, since the devices and/or systems of the present disclosure are not dimensionally dependent on a shape and/or size of a burr hole, aspects of the present disclosure realize a smaller device and/or system footprint. For example, CSF implants (e.g., FIG. 21, CSF source tube 2102) and/or DVS implants (e.g., FIG. 12. DVS implant anchor 202, DVS implant 1224 and FIG. 19, PFC device 1970, and/or the like) of the present disclosure may be generally less than about 6 mm in diameter. In some aspects, such CSF implant and/or DVS implant components may be as small as 0.5 mm in diameter. A relatively smaller footprint may permit a plurality of entry points and/or a plurality of DVS implants along the DVS of the subject (e.g., within an existing burr hole, see FIGS. 4-11). In such aspects, if a catheter (FIG. 12, e.g., CSF outlet tip 1248 in the subject's DVS) needs to be replaced (e.g., due to infection, a clog, and/or the like) it, or its replacement, may be re-inserted at another entry point. Furthermore, the plurality of entry points along the DVS may permit access to different locations to be drained (e.g., instances of loculated hydrocephalus, non-communicating hydrocephalus, and/or the like). According to various aspects of the present disclosure, a distance between a CSF inlet implant (e.g., FIG. 21, CSF source tube 2102 at CSF source) and a DVS outlet implant (e.g., FIG. 12, DVS implant anchor 202, DVS implant 1224 and FIG. 19, PFC device 1970, and/or the like) of the devices and/or systems of the present disclosure may be in the range of about 0.3 cm to about 20 cm.

The '223 application further disclosed the SAS implant plugs and/or the DVS implant plugs as generally circular implant elements for cranial implantation. According to aspects of the present disclosure, an DVS implant anchor may include at least one anchor arm coupleable to a subject's skull. In some aspects, the DVS implant anchor may include a singular anchor arm (e.g., FIGS. 4-7). In other aspects, the DVS implant anchor may include a plurality of anchor arms (e.g., FIGS. 8-11). In such aspects, each of the plurality of anchor arms may be offset from one another at preset angles. According to various aspects, one or more than one anchor arm may be a same length or one or more than one anchor arm may be a different length. According to various aspects, each anchor arm may include a mounting aperture. In such aspects, a fastener (e.g., screw) may be positioned within the mounting aperture to couple the DVS implant anchor to the subject's skull. In some aspects, the mounting aperture may be a slot such that a position of the DVS implant anchor is adjustable. In such aspects, each anchor arm may include a fixation aperture. The fixation aperture may be a hole to permanently fix the DVS implant anchor in a determined position (e.g., an adjusted position).

The '223 application further disclosed the SAS implant plug (CSF inlet) and/or the DVS implant plug (CSF outlet) as a predetermined distance apart (e.g., based on burr holes drilled via the guide device). While aspects of the present disclosure may locate the CSF inlet that predetermined distance from the CSF outlet, the distance between the CSF inlet and the CSF outlet of the devices and/or systems of the present disclosure is not limited to that predetermined distance (e.g., may be any customized distance, a burr hole guide device is not required). Furthermore, aspects of the present disclosure more flexibly permit the CSF inlet and the CSF outlet to be positioned in locations less and/or not suitable for drilling holes via a guide device.

The '223 application further disclosed the use of an adhesive (e.g., dural sealant and/or the like) for sealing a DVS implant plug to the subject's dura. However, in such aspects, a surgeon may not have a direct visual of any area surrounding the DVS implant plug to confirm that a good seal to the dura has been achieved and/or that no leakage of blood is present. According to aspects of the present disclosure, in light of a reduced size of the DVS implant anchor (e.g., less than about 6 mm in diameter), an adhesive layer as shown in FIG. 2A, with or without a fibrous or sponge-like pad 215, may provide additional stability to and exert positive control of the dura such that the dura does not allow deflection of the dura during puncture while allowing a surgeon to directly observe whether a complete seal of the DVS implant with the dura has been achieved and whether any active bleeding is present. Other methods of exerting positive control of the dura during the procedure such as surface tension enhancers e.g. a stiffening gel, applying a temporary vacuum, or a temporary adhesive to exert positive positional control of the dura are also contemplated The '223 application further disclosed the DVS implant plug as including a depth limiting feature (e.g., a tapered portion of DVS implant to mimic a tapered portion of a burr hole to control advancement of the DVS implant plug into a subject's skull to avoid dura/brain/sinus damage, to avoid bleeding, and/or the like). According to aspects of present disclosure, the DVS implant anchor may be coupled (e.g., sealed) to the subject's dura before coupling a DVS implant including a DVS outlet drain (FIG. 12, e.g., CSF outlet tip 1248) to the DVS implant anchor. Further, according to aspects of the present disclosure, a threaded portion of the DVS implant permits a precise advancement of the DVS outlet drain into a covering (e.g., dura) of the DVS (e.g., covering of the DVS may vary from subject to subject). Further according to aspects of the present disclosure because the DVS implant placement assembly (e.g., FIG. 12, DVS implant placement assembly 1220) has a removable open needle insert, the proper location of the sinus can be confirmed when the needle passes through the dura covering and allows blood to escape. The needle (e.g., FIG. 12, DVS implant driver 1222, insertion driver) of the DVS implant placement assembly may then be withdrawn. According to various aspects the needle may have different configurations (e.g., shallow, cutting, bi-bladed, solid or coring, including cutting elements that don't allow flap formation, that removes a core, that has a low force of entry through the dura, and/or the like). Further in such aspects, the DVS implant (FIG. 12, DVS implant 1224) may be deployed (e.g., inserted) with a threading action until the desired depth is reached or contact with the dura layer is satisfactory. According to further aspects of the present disclosure, a gasket, washer, sealant, hemostatic agent, and/or a combination thereof may be utilized under the DVS component(s) (e.g., DVS implant anchor 202, DVS implant 1224, or the like) to assist with hemostasis and take up slack or variation in any height discrepancy.

The '223 application as well as the present disclosure realize the advantage of using a CSF source (e.g., cisterna magna) for the CSF versus the SAS or the use of a lateral ventricle. Due to the co-location of the choroid plexus which is connected to, and supplying, the lateral ventricles, there is a propensity for materials produced in the choroid plexus (e.g. CSF, various proteins, inflammatory tissue and the like) to clog a traditional catheter over time.

The '223 application contemplated possible manipulation of the cortical surface of the brain to place the CSF inlet apparatus. The CSF drain of the present disclosure does not require retraction nor manipulation of the surface of the cortex and therefore reduces the possibility of seizures and/or inadvertent bleeding. Aspects of the present disclosure may advantageously provide a percutaneous access point for a Pressure Flow Control device (e.g., FIG. 19, PFC device 1970).

The '223 application disclosed symmetrically shaped cranial implants (e.g., SAS implant plug, DVS implant plug, or the like) that may become dislodged (e.g., with normal and/or abnormal heterotopic ossification. According to aspects of the present disclosure, the cranial implants (e.g., FIG. 16, DVS implant subassembly 1660) may be fixated to the outer table of the skull and is less susceptible to dislodgment (e.g., due to bone growth). Certain variations of the cranial implants may be made in a manner to allow bone in-growth for enhanced stability or to allow for growth in the skull for pediatric patients or to promote implant stability and reduce infection risk.

The '223 application as well as the present disclosure may advantageously provide easy access to implants and/or implant components. In various aspects, if the subject gets an implant-related infection, the DVS implant may be easily removed and a pro-coagulant may be placed on top of the DVS in its place (e.g., without disturbing any gray matter of the brain).

The '223 application disclosed use of a directional outlet tip with an integral slit, or tulip shaped one-way flap valve. Aspects of the present disclosure utilize a one-way valve (e.g., FIG. 19, ball valve 1995) in the body of the PFC device 1970 (FIG. 19) to control any possible return flow from a temporary elevated sinus blood pressure that would be higher than the CSF pressure. According to various aspects, the valve may be self-activating and it will close immediately due to the pressure from the temporary back bleeding (i.e. possible during subject sneezing, coughing, and/or the like) into the catheter (e.g., FIG. 21, CSF source tube 2102). In some aspects, the valve may be a ball/spring (e.g., FIG. 19). In other aspects, the valve may be a polymeric flap-valve, a metallic flap-valve, and/or the like. According to various aspects, as soon as the dural venous pressure drops, the valve may open such that the outlet DVS tip (e.g., CSF outlet tip 1248 of the DVS implant 1224) will be immediately flushed by CSF as the CSF pressure overcomes the dural venous pressure (e.g., minimizes any chance of a blood clot (thrombosis) formation and subsequent blockages of the outlet tip). In some aspects, the one-way valve is an integral component of the PFC device 1970 (e.g., may be easily exchanged if there is any problem after the surgery). According to various aspects, the PFC device 1970 is designed (e.g., sized and/or dimensioned) to fit within the DVS implant 1224 with or without the use of an instrument that facilitates the positioning and/or engagement of the two components.

The '223 application as well as the present disclosure may utilize navigated CT scans and/or real-time fluoroscopy of the DVS, optionally incorporating a radio-opaque endovascular catheter guide wire, balloon, stent, contrast dye or similar, to assist in the location of the ideal target insertion point on the selected dural sinus to place the DVS components (e.g., DVS implant anchor 202, DVS implant 1224, or the like) as well as assist in the placement of the proximal portion of the CSF inlet (e.g., CSF source tube 2102), as described herein, properly into the selected CSF containing space (e.g. lateral ventricle, cisterna magna, SAS). According to aspects of the present disclosure, a pressure sensing element (e.g., FIG. 29, stylet 2905) may be integrated within a needle (e.g., FIG. 29, needle 2904) to detect when the CSF containing space (e.g., the cisterna magna) has been entered by sensing the relatively higher local pressure of the CSF.

Various U.S. Patents having related subject matter may include U.S. Pat. Nos. 8,672,871, 9,737,696, 9,737,697, 9,662,479, 10,058,686, 10,258,284, 10,272,230, 10,279,154, 10,307,576, and 10,307,577 (e.g., general referred to herein as the Heilman patents).

The Heilman patents utilize an endovascular approach that leaves a long (about 3 cm) outlet drain through the inferior petrosal sinus (IPS) into the jugular vein, utilizing a tube (0.16" ID) with a slit end to act as a one-way valve, placed via the IPS into the cerebellopontine angle cistern. The Heilman patents access the CSF though the sinus to the cistern. This is opposite of the disclosure of the '223 application and the present disclosure. According to aspects of the '223 application and the present disclosure, CSF is accessed independent of the DVS implant used to access the sinus. Accordingly, aspects of the '223 application and the present disclosure may access the SAS (e.g., including the cisternal space or lateral ventricle) from anywhere inside (e.g., the lateral ventricle) or surrounding the brain (e.g., gray matter), from the spinal column e.g. around the spinal cord, without being limited to the cerebellopontine angle cistern.

In addition, the Heilman patent device only accesses the CSF from within the constraints of the interior (to the skull/neck) inferior petrosal sinus. According to aspects of the '223 application and the present disclosure, the DVS device could be used to access any exterior (e.g., to the brain) dural sinus (e.g., sagittal sinus, transverse sinus, and/or the like). Further, the Heilman patent's drain portion is relatively long (about 3 cm), presenting a very large foreign body presence in the inferior petrosal sinus as well as the jugular. According to aspects of the '223 application and the present disclosure, the DVS device only minimally protrudes (e.g., less than about 1-3 mm) into the DVS. Furthermore, the DVS device of the '223 application and the present disclosure is a modular design that allows for easy changing (e.g., the DVS is accessible from the outside of the subject's skull). Also, the DVS device of the '223 application and the present disclosure, the modular design allows for the CSF flow to be from above or below the location of the DVS. According to aspects of the present disclosure, the desired flow and back-pressure can be easily modified with an easy substitution of the PFC device (e.g., sub-component) as required for each subject. Such an adjustment may be done without disturbing the outlet portion of the DVS. Oppositely, the Heilman patents are limited to having to completely remove the implant to change the flow and pressure conditions for a subject. Namely, the Heilman patents place the flow control device (e.g., 3 mm long, with length-wise slits) in the drainage end of its tubing. This slit area is surround by blood at all times and thus will be susceptible to blockages caused by blood clots. According to aspects of the present disclosure, the PFC device does not reside in the bloodstream but instead is located just above the sinus (e.g., removably housed in the body of the DVS implant). If a blockage were to occur, the PFC device of the present disclosure may be easily exchanged in an outpatient setting. Lastly, the Heilman patents have no ready available access to sample CSF contents (i.e. proteins, bacteria, and/or the like). According to aspects of the present disclosure, CSF is easily accessible via needle access to the PVC just below skin level.

Another U.S. Patent having related subject matter may include U.S. Pat. No. 9,402,982 (e.g., generally referred to herein as the Baert patent) for a minimally-advancing luminal catheter. The Baert patent places a tubular shunt from the ventricle into the sagittal sinus and utilizes a stop element on the tubing to limit the insertion depth of the tubing into the sagittal sinus. Another U.S. Patent having related subject matter may include U.S. Pat. No. 10,625,061 (e.g., generally referred to herein as the Borgesen patent) for shunting CSF to a sinus system cavity. The Borgesen patent uses a tubular element with a one-way valve and an attached stent-like device for locating an outlet inside the sinus and away from any endothelium surface, i.e., centered (central) in the sinus flow. In contrast to the Baert patent and the Borgesen patent, aspects of the present disclosure require no such depth limiting component since our DVS implant anchor is sitting on top of the dura, before attachment of the DVS implant which contains the CSF outlet. Further, the depth of the DVS implant, of the present disclosure, in one instance, has a threaded body that allows for precise advancement of the CSF outlet into, and through, the dural sinus covering where the thickness of the dura can vary from patient to patient and in another instance, PFC-DVS drain assembly contains a drain (e.g., CSF outlet) component, with a length between 1 to 2.5 mm that is selected to only minimally penetrate (e.g. 1.5 mm or less) the inner wall of the superior DVS. The implant insertion driver, of the present disclosure, allows for differences in skull thickness as well as allowing for a prescribed amount of implant to be inserted into DVS to minimize the risk of thrombosis.

Reference will now be made in detail to various aspects of the methods, devices, systems, and/or kits of the present disclosure to drain CSF from a subject's CSF containing space into the subject's DVS, examples of which are illustrated in the accompanying drawings. Whenever possible, the same reference numerals will be used throughout the drawings to refer to the same or like parts.

Figure 1A:
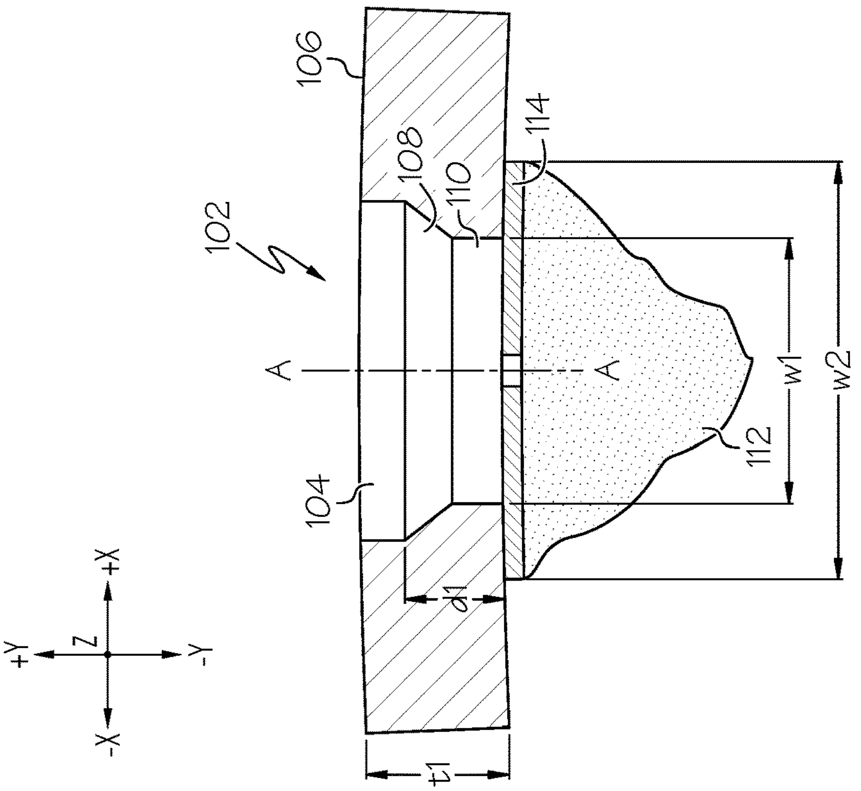
FIG. 1A depicts a cross-sectional view of an illustrative DVS burr hole 102 as drilled in a subject's skull, according to one or more aspects shown and described herein.

FIG. 1A depicts a cross-sectional view of an illustrative DVS burr hole 102 as drilled in a subject's skull 106 (e.g., cranium), according to various aspects of the present disclosure. In some aspects, the DVS burr hole 102 may be created using an off-the-shelf ACRA-CUT® cranial perforator (ACRA-CUT®, Acton, Massachusetts) adjustable to subject size (e.g., adult or pediatric). Referring to FIG. 1A, according to various aspects, a DVS burr hole 102 is defined by a first aperture portion 104, a second aperture portion 108, and a third aperture portion 110 through a thickness "t1" of the skull 106 about a first axis (e.g., axis A-A as depicted in FIG. 1A). According to various aspects, a diameter associated with the first aperture portion 104 may be larger than a diameter associated with the third aperture portion 110. In such an aspect, the second aperture portion 108 may gradually decrease in diameter from the diameter associated with the first aperture portion 104 to the diameter associated with the third aperture portion 110 thereby defining a taper or chamfer therebetween. Referring to FIG. 1A, such DVS burr hole 102 portions are defined within the thickness "t1," a known distance from an interface between the skull bone and underlying dura 114. According to various aspects, a drill (e.g., a step drill designed to pop through the lower table/surface of the skull bone 106 without penetrating the dura) may be used to drill the DVS burr hole 102 with such defined portions. In one example, the third aperture portion 110 may be a third diameter (e.g., about 11 mm) through a third part (e.g., about 2 mm) of the thickness "t1" of the skull 106. Further in such an example, the first aperture portion 104 may be a first diameter (e.g., about 14 mm) through a first variable part (e.g., about "X" mm) of the thickness "t1" of the skull 106 (e.g., variable due to potential differences in thickness of a skull of the subject, e.g., an adult subject versus a juvenile subject). Yet further in such an example, the second aperture portion 108 may transition between the first diameter (e.g., about 14 mm) to the third diameter (e.g., about 11 mm) at a predefine angle (e.g.,) 45° through a second part (e.g., about 2 mm-3 mm) of the thickness "t1" of the skull 106. Overall, referring to FIG. 1A, a depth "d1" defined by the second part of the thickness "t1" of the skull 106 and the third part of the thickness "t1" of the skull 106 may be a controlled, predetermined distance. As described herein, various implant designs (e.g., FIG. 2A, DVS implant anchor 202) may take into account this controlled, predetermined distance "d1" (e.g., FIG. 2A, depth "d2" of the DVS implant anchor 202 may substantially equal depth "d1" as depicted in FIG. 1A).

Referring still to FIG. 1A, the DVS burr hole 102 should be positioned in close proximity to and/or over a (laterally) central portion of a dural venous sinus (DVS) 112 (e.g., generally depicted by a triangular shape in FIG. 1A, e.g., the transverse sinus). Here, navigated CT, x-ray, and/or fluoroscopy imaging of the DVS, optionally incorporating a radio-opaque endovascular catheter guide wire, balloon, stent, contrast dye or similar, to assist in the location of the ideal target insertion point on the selected dural sinus may be used to locate a drill (e.g., cranial perforator) over the DVS 112 before drilling the DVS burr hole 102 and also used to direct final placement of the DVS implant. If the DVS 112 is not visually evident (e.g., to the surgeon) after the DVS burr hole 102 has been drilled, the DVS 112 location may be visually confirmed with a UV light (e.g., may appear purple in color), or by using one or more radio-opaque IV contrast dyes, in conjunction with fluoroscopy or by using near infra-red light (e.g. via an AccuVein® Vein Finder, Medford, New York or the like) to identify the DVS 112 location. The DVS 112, as described herein, may be the sagittal sinus (SS), the transverse sinus (TS), and/or the like, through which blood flows). In view of FIG. 1A, the third aperture portion 110 of the DVS burr hole 102 may be marginally smaller (e.g., w1<w2) than the target portion (e.g., central portion of "t2" as depicted in FIG. 1A) of the DVS 112. For example, a subject's torcular herophili (e.g., confluence of the sinuses) may be about 10 mm (e.g., on average).

FIG. 1B depicts a perspective view of the illustrative DVS burr hole 102 of FIG. 1A, according to various aspects of the present disclosure. In view of FIG. 1B, the DVS burr hole 102 has been drilled through the subject's skull 106 to expose the dura 114 for access to the subject's DVS 112 (e.g., below dura 114 as depicted in FIG. 1A).

FIG. 2A depicts a cross-sectional view of an illustrative DVS implant anchor 202 positioned within the DVS burr hole 102 of FIG. 1A, according to various aspects of the present disclosure. Referring to FIG. 2A, a first portion 206 of an anchor body 204 may be defined in a first longitudinal direction (e.g., in the +X direction of the coordinate axes of FIG. 2A) and a second portion 208 of the anchor body 204 may be defined in a second longitudinal direction (e.g., in the −X direction of the coordinate axes of FIG. 2A). A connector portion 207 may couple the first portion 206 to the second portion 208. More specifically, the connector portion 207 may couple the first portion 206 to the second portion at an offset depth "d3" as depicted in FIG. 2A. In some aspects, the offset depth "d3" may correspond to a depth of the first part of the thickness "t1" of the skull 106 (FIG. 1A, e.g., depth of the first aperture portion 104 of the DVS burr hole 102). According to various aspects described herein, the connector portion 207 and the first portion 206 may be referred to as an implant anchor arm 209. According to various aspects of the present disclosure, the anchor body 204 of the DVS implant anchor 202, including the first portion 206, the connector portion 207, and/or the second portion 208, may be manufactured using a material (e.g., polymer (silicon rubber or the like), metal (stainless steel, titanium or the like), polyester, and/or the like, or biologics or resorbable materials (e.g., collagen, magnesium or various polymers) suitable for the uses described herein. Furthermore, the anchor body 204 of the DVS implant anchor 202 may be manufactured via various processes (e.g., a blow molding process, an injection molding process, a machining process, a 3D printing process, and/or the like).

An adjustment hole 210 and a fixation hole 212 may be defined in the first portion 206 of the anchor body 204 (see FIG. 2B), about a second axis (e.g., axis B-B as depicted in FIG. 2A) and about a third axis (e.g., axis C-C as depicted in FIG. 2A), respectively. Similarly, a DVS implant aperture 214 may be defined, about a fourth axis (e.g., axis D-D as depicted to be generally orthogonal to the DVS 214 in FIG. 2A) in the second portion 208 of the anchor body 204.

Still referring to FIG. 2A, each of the adjustment hole 210 and the fixation hole 212 may be located (e.g., in the +X/−X longitudinal direction of the coordinate axes of FIG. 2A) on the first portion 206 such that the adjustment hole 210 and the fixation hole 212 are over the subject's skull 106 when the DVS implant aperture 214 is positioned within the DVS burr hole 102 (FIG. 1A). In some aspects, the fourth axis (FIG. 2A, e.g., axis D-D) of the DVS implant aperture 214 may be aligned with the first axis (FIG. 1A, e.g., axis A-A) of the DVS burr hole 102 to centrally locate (e.g., initially) the DVS implant aperture 214 within the DVS burr hole 102. In other aspects, the DVS implant anchor 202 may be adjusted (e.g., initially and/or subsequently) such that the fourth axis (e.g., axis D-D) is not in alignment with the first axis (e.g., axis A-A) of the DVS burr hole 102 (e.g., in alignment with any other axis perpendicular to the X-Z plane of the coordinate axes of FIG. 2A within the DVS burr hole 102). In this vein, according to various aspects, each of the adjustment hole 210 and the fixation hole 212 may be located (e.g., in the +X/−X longitudinal direction of the coordinate axes of FIG. 2A) on the first portion 206 such that the adjustment hole 210 and the fixation hole 212 are over the subject's skull 106 when the DVS implant aperture 214 is positioned anywhere within the DVS burr hole 102.

In further view of FIG. 2A, the DVS implant aperture 214 may be defined by an outer diameter 218 and an inner diameter 216 of the second portion 208. Further in view of FIG. 2A, a threaded portion 220 may be defined in the inner diameter 216 of the second portion 208. The threaded portion 220 may threadedly receive a DVS implant (e.g., FIG. 12), as discussed herein.

Figure 2B:
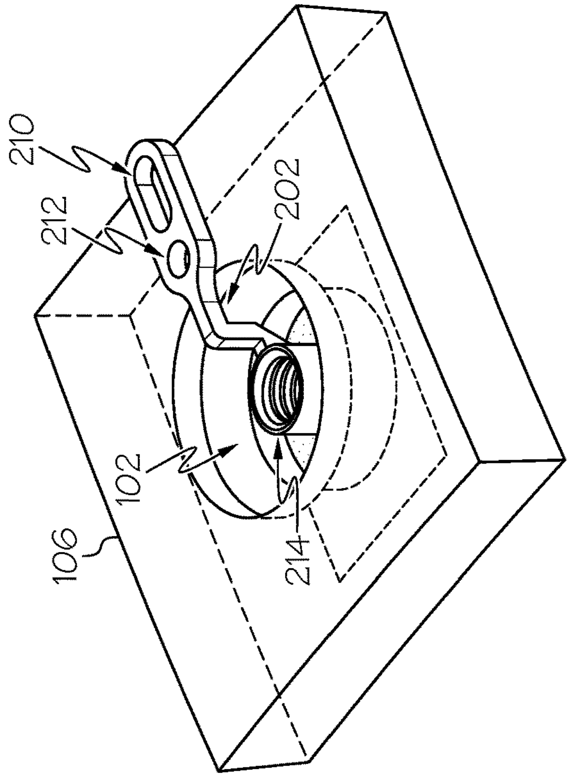
FIG. 2B depicts a perspective view of the illustrative DVS implant anchor 202 of FIG. 2A, according to one or more aspects shown and described herein.
Figure 2A:
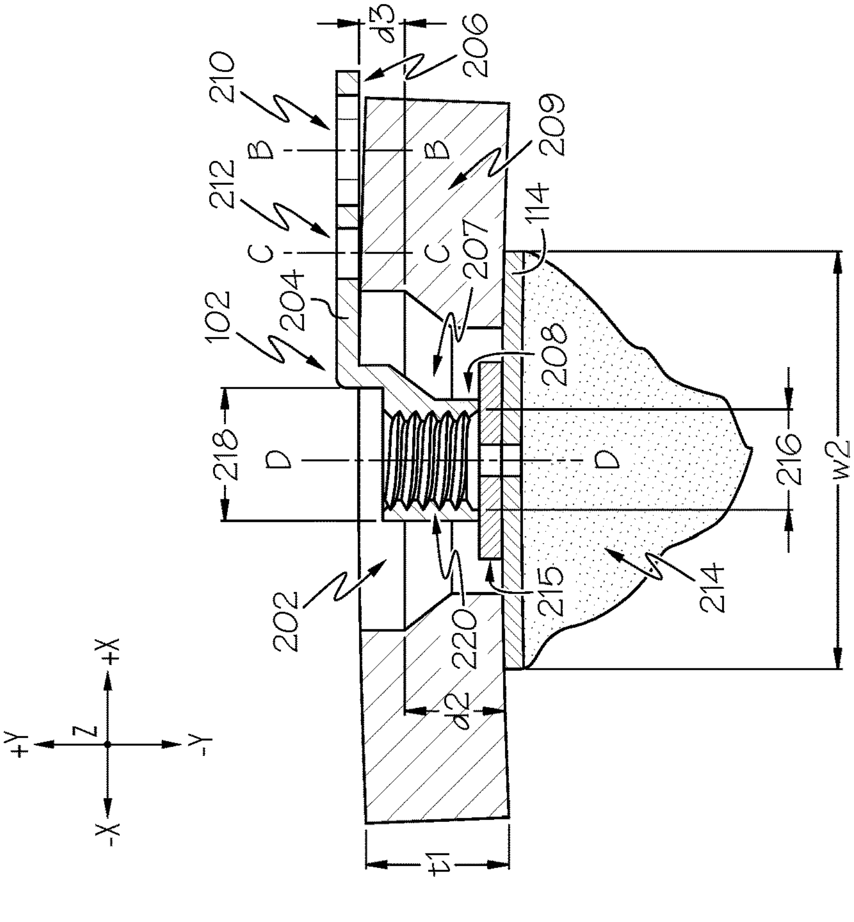
FIG. 2A depicts a cross-sectional view of an illustrative DVS implant anchor positioned within the DVS burr hole of FIG. 1A, according to one or more aspects shown and described herein.

FIG. 2B depicts a perspective view of the illustrative DVS implant anchor 202 of FIG. 2A, according to various aspects of the present disclosure. In view of FIG. 2B, each of the adjustment hole 210 and the fixation hole 212 are located over the subject's skull 106 when the DVS implant aperture 214 is positioned (e.g., centrally and/or non-centrally) within the DVS burr hole 102. Further in view of FIG. 2B, the adjustment hole 210 may be defined as a slotted hole and the fixation hole 212 may not be a slotted hole (e.g., circular). In view of FIG. 2B, it should be appreciated that the position of the adjustment hole 210 and the fixation hole 212 may be switched. Such an aspect may permit a slotted adjustment hole to extend into/over the DVS burr hole 102 while still permitting use of the fixation hole 212 to secure the DVS implant anchor 202 to the subject's skull 106.

Figure 2D:
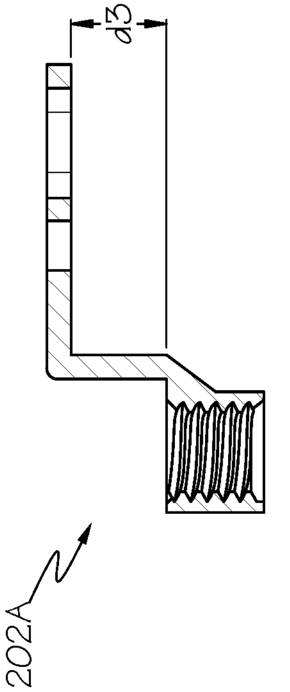
FIG. 2D depicts a cross-sectional view of an illustrative DVS implant anchor, according to one or more aspects shown and described herein.
Figure 2E:
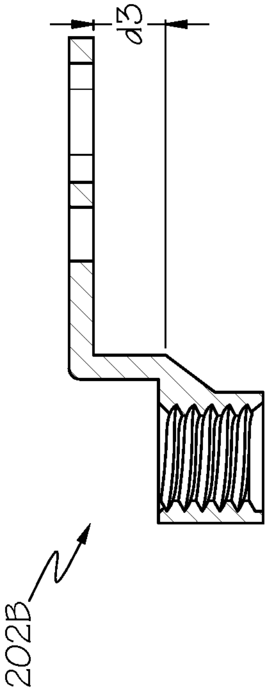
FIG. 2E depicts a cross-sectional view of an illustrative DVS implant anchor, according to one or more aspects shown and described herein.
Figure 2F:
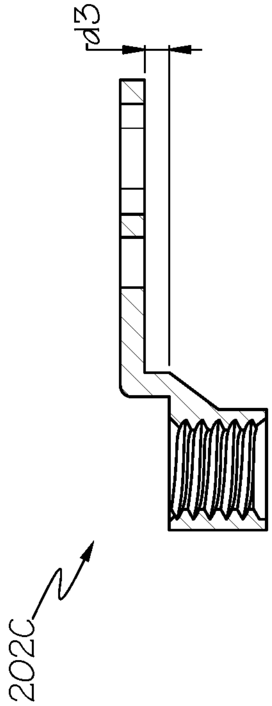
FIG. 2F depicts a cross-sectional view of an illustrative DVS implant anchor, according to one or more aspects shown and described herein.
Figure 2C:
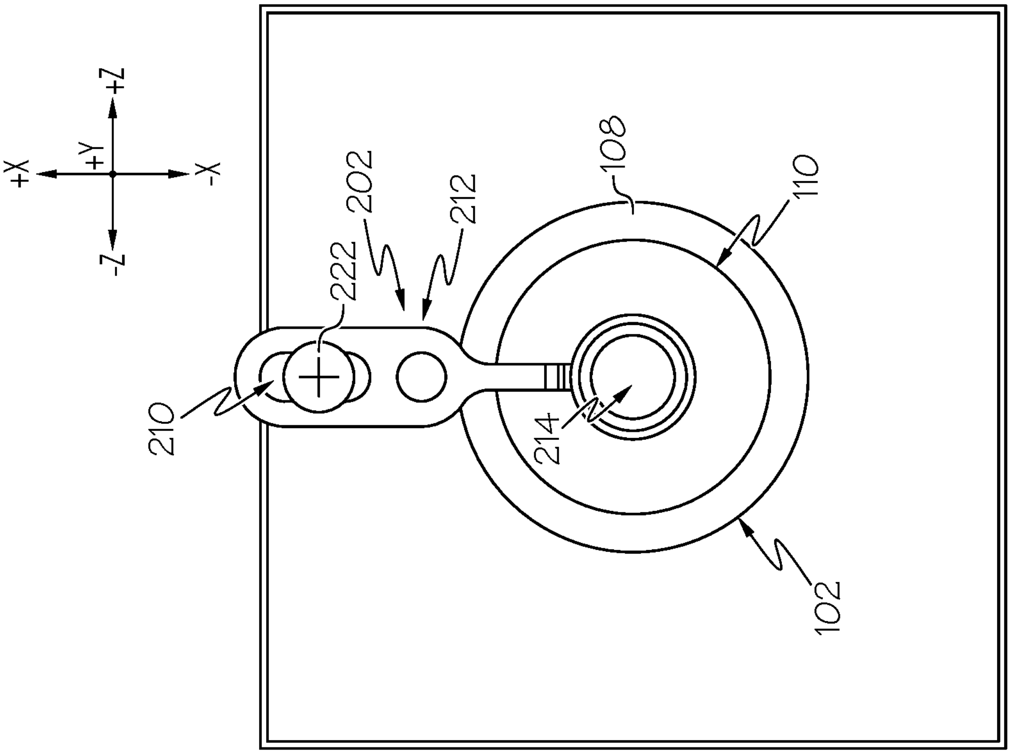
FIG. 2C depicts a top view of the illustrative DVS implant anchor 202 of FIG. 2A, according to one or more aspects shown and described herein.

FIG. 2C depicts a top view of the illustrative DVS implant anchor 202 of FIG. 2A, according to various aspects of the present disclosure. In FIG. 2C, the subject's dura 114 has been removed for case of illustration. Referring to FIG. 2B, for illustration purposes, the DVS implant aperture 214 of the DVS implant anchor 202 is positioned concentrically within the DVS burr hole 102 (e.g. over the DVS 112 midline). More specifically, the DVS implant aperture 214 is positioned concentrically with respect to the second aperture portion 108 and the third aperture portion 110 (see also FIG. 2A), recognizing that, in practice, the DVS implant aperture 214 could be positioned anywhere within the third aperture portion 110. Furthermore, in view of FIG. 2C, a first fastener 222 (e.g. surgical screw and/or the like) may be fastened through the adjustment hole 210 to adjustably couple the DVS implant anchor 202 to the subject's skull 106 and a second fastener 224 (not shown, similar to the first fastener 222) may be fastened through the fixation hole 212 to fixedly couple the DVS implant anchor 202 to the subject's skull 106.

Figure 3:
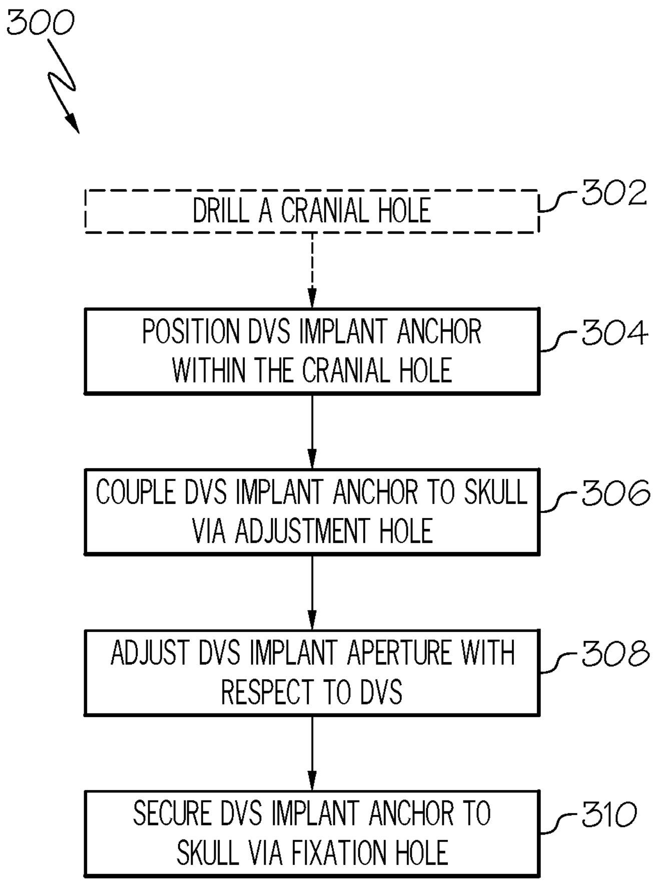
FIG. 3 depicts a flow diagram of an illustrative method for coupling the DVS implant anchor of FIG. 2A to a subject's skull, according to one or more aspects shown and described herein.

FIG. 3 depicts a flow diagram of an illustrative method 300 for coupling the DVS implant anchor 202 of FIG. 2A to a subject's skull 106, according to various aspects of the present disclosure. Referring to FIG. 3, at block 302, the method may include drilling a cranial hole. According to various aspects, the cranial hole may include a DVS burr hole 102 (e.g., FIG. 1A). Block 302 is shown in phantom as optional. Here, according to various aspects of the present disclosure, a cranial hole (e.g., burr hole) may already exist in the subject's skull 106. This is a clear benefit of the DVS implant anchor 202 as described herein. More specifically, referring briefly to FIG. 2A, the DVS implant anchor 202 of the present disclosure is not limited to any specific cranial hole (e.g., the DVS burr hole 102 of FIG. 1A). According to various aspects, the DVS implant anchor 202 may be inserted within any cranial hole having access to the subject's DVS 112 (FIG. 1A) where that cranial hole can accommodate the outer diameter 218 of the second portion 208 of the DVS implant anchor 202 (see FIG. 2A). Accordingly, in light of FIG. 2A, aspects of the present disclosure may include a plurality of DVS implant anchors 202 where each DVS implant anchor 202 may include a different inner diameter 216 and/or outer diameter 218 and/or a different combination of d2 and d3 values to accommodate various patient t1 values (FIG. 1A, skull thickness). For example, according to various aspects, DVS implant anchors 202 may be sized and/or dimensioned for adult subjects, DVS implant anchors 202 may be sized and/or dimensioned for juvenile subjects, and/or the like. The anchor material may optionally have the ability to be flexible or compliant enough to facilitate surgical use, allow for post-surgical dural swelling or retraction and adjusting for subsequent bone growth after the surgery. In addition, as shown in FIGS. 2D-2F, illustrative implant anchors are illustrated including different values of d3 (FIG. 2A). For example, an illustrative implant anchor 202A is shown in FIG. 2D having a value d3 greater than a value d3 of an illustrative implant anchor 202B illustrated in FIG. 2E, which is greater than a value d3 of an illustrative implant anchor 202C illustrated in FIG. 2F.

Referring now to FIGS. 2G-2K, an endovascular approach is disclosed to locate a target implant access to a DVS 240 extending in a longitudinal direction beneath a subject's skull 242. In embodiments, under fluoroscopic guidance, a catheter wire 244, for example, a 014-016 catheter wire, is fed through a jugular bulb or other suitable originating venous access point to the DVS location (e.g. the transverse or the sagittal sinus) where the CSF drain device/implant will be implanted, as discussed herein. Endovascular techniques such as where the catheter wire 244 is substituted with wires that contain various transducer portions to provide ultrasound imaging, pressure measurements, or venography can be used to assist in selection of the location. Deployment of the catheter wire 244 into the DVS 240 may also may include features or components to facilitate or augment these techniques such as, for example, the use of balloons to expand the DVS 240 or centralize the location of the catheter wire 244.

Figure 2G:
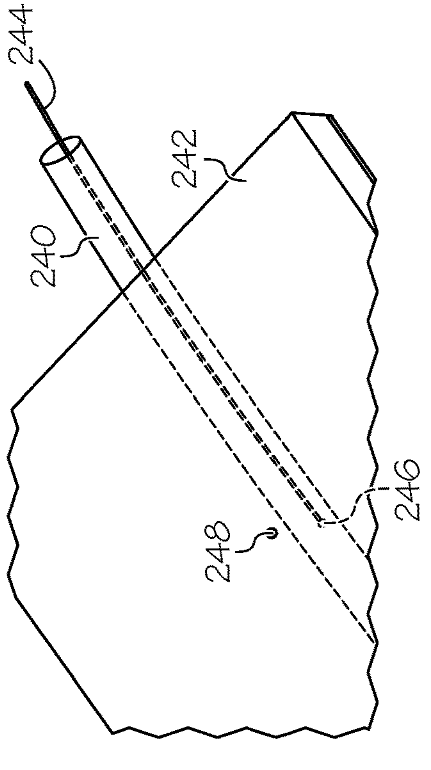
FIG. 2G depicts a perspective view of a catheter wire being fed through a stent and a DVS, according to one or more aspects shown and described herein.

FIG. 2G depicts the catheter wire 244 extending through the DVS 240 and an external, opaque x-ray marker, such as a needle, not shown, is used to identify with fluoroscopic guidance an end 246 of the catheter wire 244. The end 246 of the catheter wire 244 is then marked, as indicated by marking 248, on the subject's skull 242. The location of the marking confirms a location of the end 246 of the catheter wire 244 being centralized laterally (i.e., along a longitudinal mid-line) within the DVS 240.

Figure 2H:
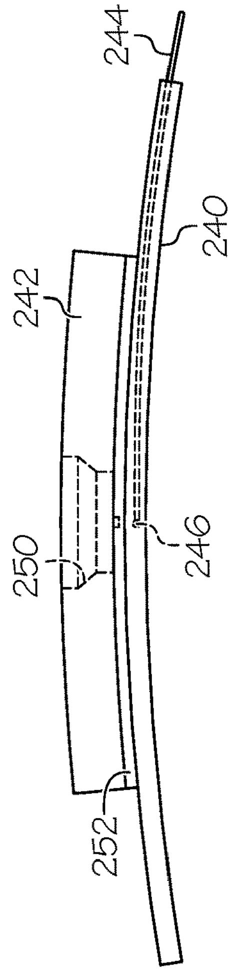
FIG. 2H depicts a cross-sectional view of the catheter wire of FIG. 2G extending through the stent and the DVS of FIG. 2G, according to one or more aspects shown and described herein.
Figure 2I:
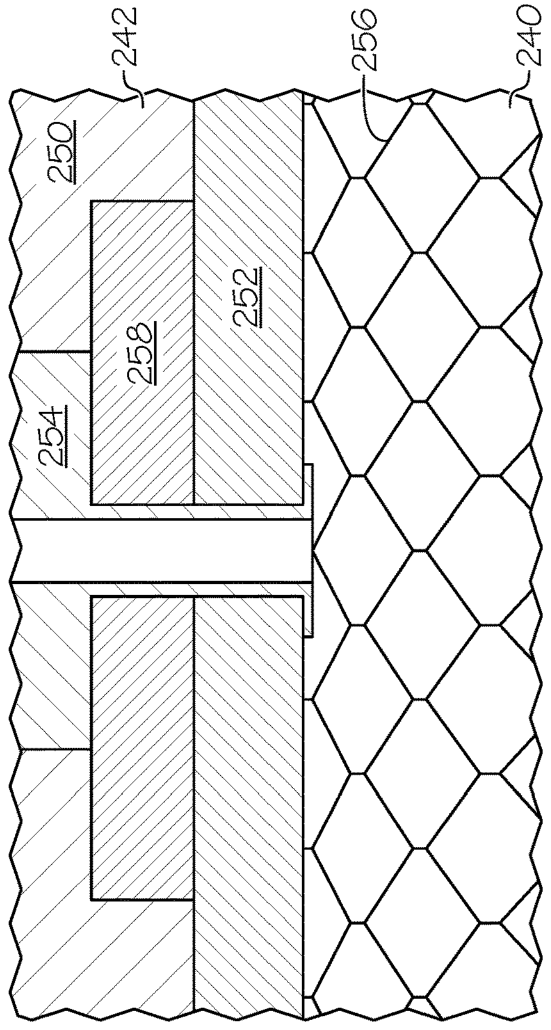
FIG. 2I depicts an enlarged cross-sectional view of a CSF drain implant engaging the stent of FIG. 2G, according to one or more aspects shown and described herein.

FIG. 2H depicts a burr hole 250 formed, e.g., by performing a craniotomy, at the marked location corresponding to the end 246 of the catheter wire 244. The burr hole 250 may be formed using a burring or drilling device being sure to maintain an orthogonal direction of the drilling device while forming the burr hole 250. Use of a burr guide is described in more detail herein with or without navigational guidance.

After the burr hole 250 is formed, i.e., craniotomy is performed, any remaining portion of the skull 242 is removed to expose the dura 252. Again, similar to the technique shown in FIG. 2G, using a needle as an x-ray identifier and utilizing fluoroscopy, the end 246 of the catheter wire 244 is marked on the dura 252. The size of the burr hole 250 may be adjusted to be wider as necessary.

Figure 21:
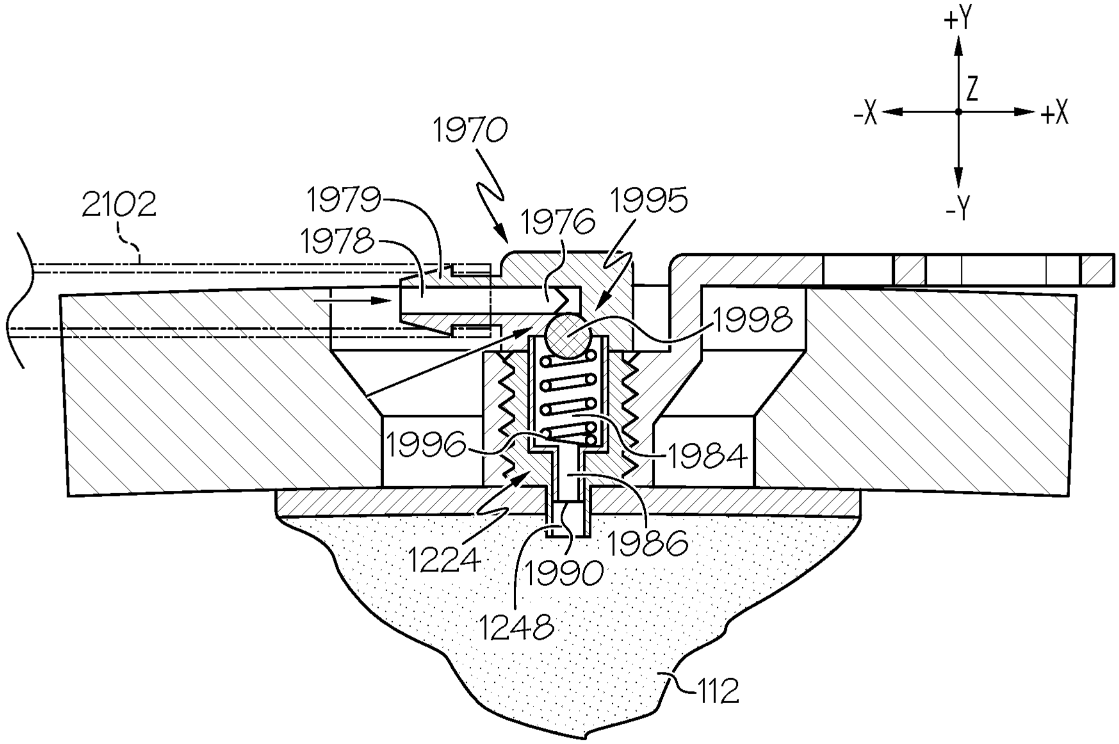
FIG. 21 depicts a cross-sectional view of the ball valve of the PFC device of FIG. 19 in a closed position, according to one or more aspects shown and described herein.

FIG. 21 depicts an implant 254, such as implant 1224, within the burr hole 250 and aligned with the marking on the dura 252. It should be appreciated that a stent 256, or other expanding or otherwise fixed intravascular implant, may be placed within the DVS 240 at the target location, i.e., the end 246 of the catheter wire 244, to establish and maintain a uniform shape of the DVS 240. As shown, the implant at least partially extends through the dura 252 and into the stent 256 to secure the implant 254 within the target location of the DVS 240. More specifically, the implant 254 may then be mechanically or adhesively joined or co-located to the stent 256 for additional stability and location control of the implant to the DVS 240. In addition, a dura stiffening pad 258, as discussed in more detail herein, may be positioned between the dura 252 and a planar bottom surface of the implant 254.

Figure 2K:
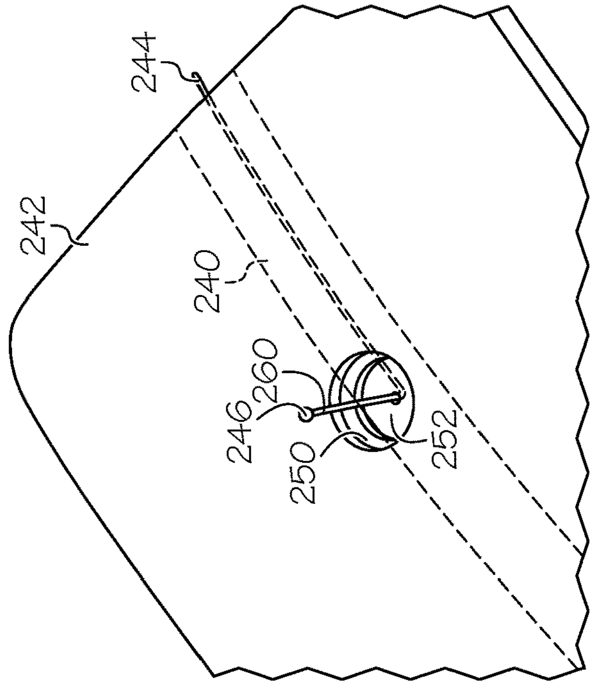
FIG. 2K depicts a perspective view of a needle extending from a distal end of the catheter wire of FIG. 2G and extending out of the DVS, according to one or more aspects shown and described herein.
Figure 2J:
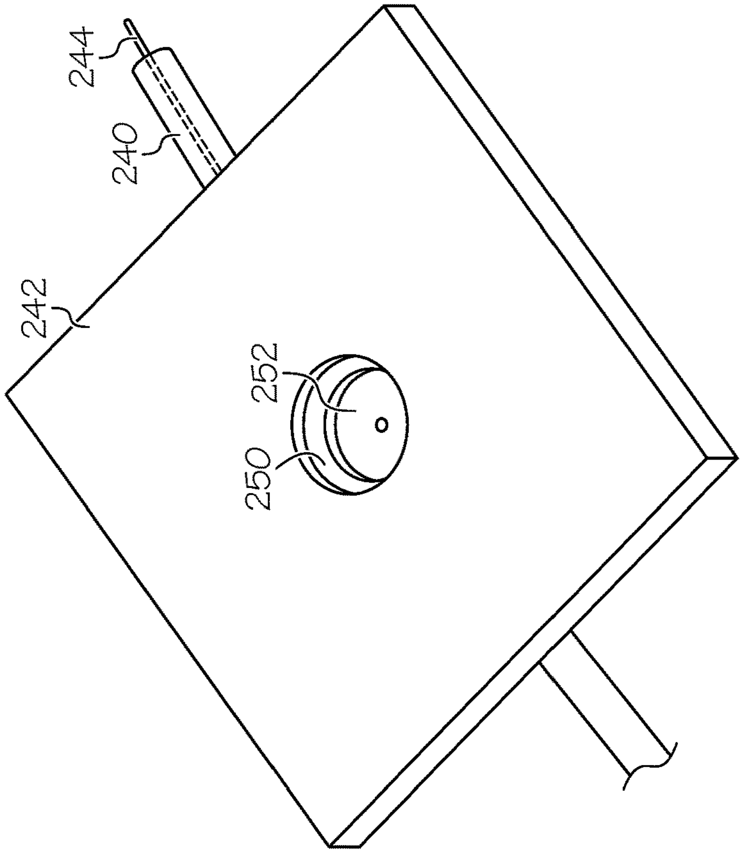
FIG. 2J depicts a perspective view of an end of the catheter being marked, according to one or more aspects shown and described herein.

In other embodiments, FIGS. 2J and 2K depict the end 246 of the catheter wire 244 being passed upward through the dura 252 and through the burr hole 250. Similar to the technique shown in FIG. 2G, using a needle as an x-ray identifier and utilizing fluoroscopy to identify the end 246 of the catheter wire 244, the needle marks the dura 252 relative to the position of the end 246 of the catheter wire 244. Thereafter, the end 246 of the catheter wire 244, which has a sharp tip, and a catheter sheath with a curved end, is directed to pass the catheter wire 244 up through the region of exposed dura 252, using a combination of fluoroscopic guidance and visual deformation of the exposed dura 252 to guide the catheter wire 244 through the dura 252. The exposed portion 260 of the catheter wire 244 can then be used as a direct visual guide for positioning the implant 254 on the dura 252 by placing an implant anchor, such as implant anchor 202, over the burr hole 250 and aligning the implant 254 with the now exposed portion 260 of the catheter wire 244 extending through the dura 252.

Still referring to FIG. 3, at block 304, the method may include positioning the DVS implant anchor 202 within the cranial hole. As described herein, in some aspects, the cranial hole may be the DVS burr hole 102 (FIG. 1A). At block 306, the method may include coupling the DVS implant anchor 202 to the subject's skull 106 via the adjustment hole 210 (FIG. 2B). In such aspects, a first fastener 222 may be used to couple the DVS implant anchor 202 to the subject's skull 106. According to various aspects, the coupling may include advancing the first fastener 222 into the subject's skull 106 until a head of the first fastener 222 snuggly holds the DVS implant anchor 202 against the subject's skull 106.

Referring still to FIG. 3, at block 308, the method may include adjusting the DVS implant aperture 214 of the DVS implant anchor 202 with respect to the subject's DVS. The depth of the burr hole is first measured. Then implant anchor 202 is selected from an available kit containing various configurations of the anchor 202 as representatively shown in FIG. 2A, including variations that provide for use in deeper or shallower burr holes, such as those illustrated in FIGS. 2D-2F. Ideally, the correct size will allow the bottom of the anchor 202 to just contact the exposed dura. Optionally, an adhesive or a conformal fibrous or sponge-like material pad 215 that contains adhesive, may also be applied to the bottom of the anchor 202 to secure the dura to the bottom of the anchor 202 to add positional stability to, and exert positive control of, the dura such that the dura does not allow deflection of the dura during puncture. The pad 215 acts to reinforce an area of puncture such that tearing of the dura and/or a risk of subsequent bleeding and/or leakage of CSF is minimized. The pad 215 may be made of temporary (e.g. resorbable) or permanent materials. For example, according to various aspects, the DVS implant aperture 214 may be positioned and/or repositioned to a central portion of the subject's DVS. In such aspects, the DVS implant aperture 214 may be positioned and/or repositioned via the adjustment hole 210. More specifically, in light of FIG. 2C, the DVS implant aperture 214 may be translated, via a slot of the adjustment hole 210, in a first longitudinal direction (e.g., in the +X direction of the coordinate axes of FIG. 2C) and/or in a second longitudinal direction (e.g., in the −X direction of the coordinate axes of FIG. 2C). Furthermore, in light of FIG. 2C, the DVS implant aperture 214 may be rotated about the first fastener 222 (e.g., in the X-Z plane of the coordinate axes of FIG. 2C) to any position within the DVS burr hole 102 (e.g., to position the DVS implant aperture over the subject's DVS).

Yet further in view of FIG. 3, at block 310, the method may include securing the DVS implant anchor 202 to the subject's skull via the fixation hole 212). In such aspects, the second fastener 224 may be used to fixedly couple the DVS implant anchor 202 to the subject's skull 106. According to various aspects, the coupling may include advancing the second fastener 224 into the subject's skull 106 until a head of the first fastener 222 tightly holds the DVS implant anchor 202 against the subject's skull 106 to prevent further movement of the DVS implant anchor 202.

FIGS. 4-7 depict top views of a plurality of illustrative DVS implant anchors, each including a plurality of equal length implant anchor arms, according to various aspects of the present disclosure. Here, although FIGS. 4-7 each depict two implant anchor arms, it should be understood that the DVS implant anchors of the present disclosure may include at least one implant anchor arm and/or more than two implant anchor arms. Similar to as described herein, each of the plurality of DVS implant anchors of FIGS. 4-7 may be manufactured using a material (e.g., polymer (silicon rubber or the like), metal (stainless steel, titanium or the like), polyester, and/or the like) suitable for the uses described herein and may be manufactured via various processes (e.g., a blow molding process, an injection molding process, a machining process, a 3D printing process, and/or the like).

Figure 4:
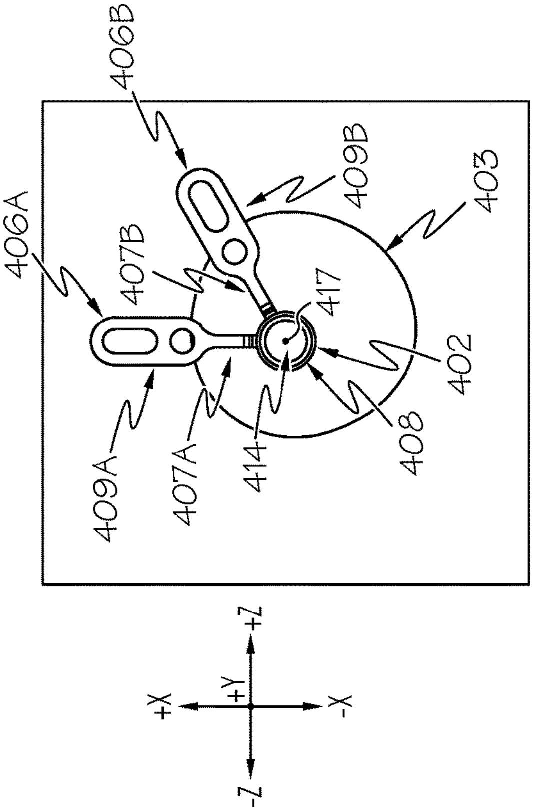
FIG. 4 depicts an illustrative DVS implant anchor including a first implant anchor arm and a second implant anchor arm of equal length, according to one or more aspects shown and described herein.

FIG. 4 depicts an illustrative DVS implant anchor 402 including a first implant anchor arm 409A and a second implant anchor arm 409B of equal length, according to various aspects of the present disclosure. The first implant anchor arm 409A may include a first portion 406A and a connector portion 407A, the connector portion 407A coupling the first portion 406A to the second portion 408 of the DVS implant anchor 402. Similarly, the second implant anchor arm 409B may include a first portion 406B and a connector portion 407B, the connector portion 407B coupling the first portion 406B to the second portion 408 of the DVS implant anchor 402. As depicted in FIG. 4, the first implant anchor arm 409A may be positioned in a first direction (e.g., in the +X direction of the coordinate axes associated with FIGS. 4-7) and the second implant anchor arm 409B may be positioned at an angle relative to the first implant anchor arm 409A (e.g., about a center 417 of a DVS implant aperture 414 of the second portion 408). In view of FIG. 4, the angle may be an acute angle (e.g., in a range between about 0 degrees and about 90 degrees). Further as depicted in FIG. 4, a length of the first implant anchor arm 409A and a length of the second implant anchor arm 409B may be substantially equal. According to various aspects, the length of the first implant anchor arm 409A and the second implant anchor arm 409B may be based on a cranial hole 403 (e.g., a maximum distance between any edge of the cranial hole 403 and a central location of the cranial hole 403) plus a length to ensure that at least part of the first portion 406A and the first portion 406B, respectively are positioned over the subject's skull 106. In view of FIG. 4, the cranial hole 403 may not be a circular hole (e.g., oblong, oval, irregularly shaped, an opening larger than the DVS burr hole 102 of FIG. 1A, and/or the like). According to various aspects, as a DVS burr hole 102 is utilized, the roundness of the DVS burr hole may cede (e.g., wear and tear, new bone growth, and/or the like). Accordingly, the length of the first implant anchor arm 409A and the second implant anchor arm 409B may allow the DVS implant aperture 414 to be positioned anywhere within the cranial hole 403. The DVS anchor 402 may also be used to adjust the DVS implant position to be orthogonal to the DVS.

Figure 5:
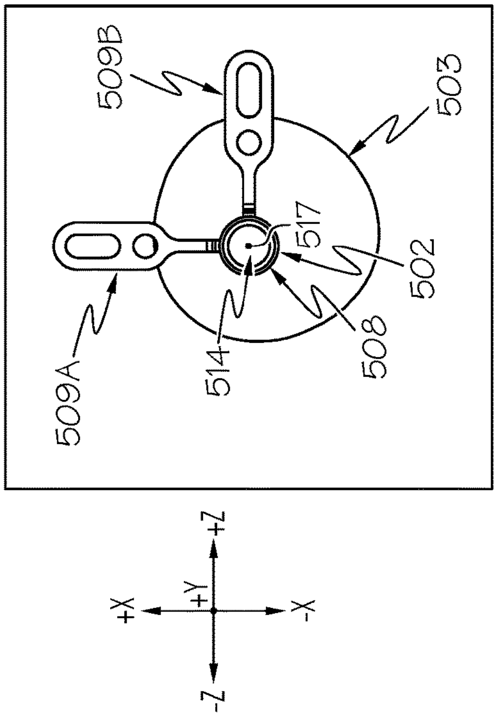
FIG. 5 depicts another illustrative DVS implant anchor including a first implant anchor arm and a second implant anchor arm of equal length, according to one or more aspects shown and described herein.

FIG. 5 depicts another illustrative DVS implant anchor 502 including a first implant anchor arm 509A and a second implant anchor arm 509B of equal length, according to various aspects of the present disclosure. Similar to as described in FIG. 4, the first implant anchor arm 509A may be positioned in a first direction (e.g., in the +X direction of the coordinate axes associated with FIGS. 4-7) and the second implant anchor arm 509B may be positioned at an angle relative to the first implant anchor arm 509A (e.g., about a center 517 of a DVS implant aperture 514 of the second portion 508 of the DVS implant anchor 502). In view of FIG. 5, the angle may be a substantially right angle (e.g., about 90 degrees). Further, similar to FIG. 4, a length of the first implant anchor arm 509A and the second implant anchor arm 509B may be based on a cranial hole 503.

Figure 6:
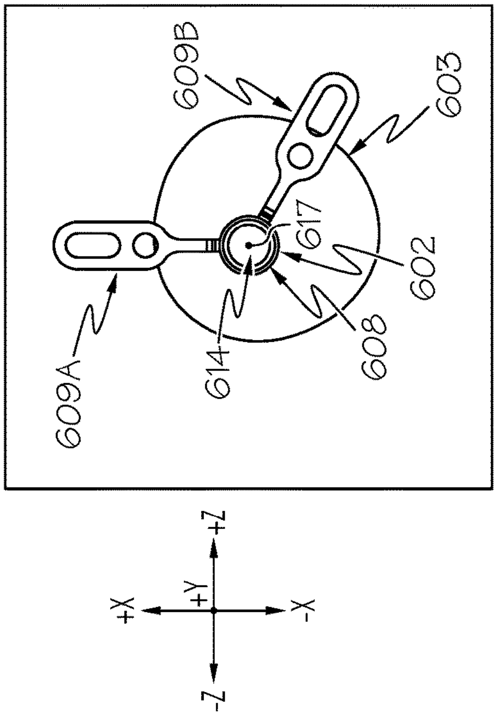
FIG. 6 depicts yet another illustrative DVS implant anchor including a first implant anchor arm and a second implant anchor arm of equal length, according to one or more aspects shown and described herein.

FIG. 6 depicts yet another illustrative DVS implant anchor 602 including a first implant anchor arm 609A and a second implant anchor arm 609B of equal length, according to various aspects of the present disclosure. Similar to as described in FIG. 4, the first implant anchor arm 609A may be positioned in a first direction (e.g., in the +X direction of the coordinate axes associated with FIGS. 4-7) and the second implant anchor arm 609B may be positioned at an angle relative to the first implant anchor arm 609A (e.g., about a center 617 of a DVS implant aperture 614 of the second portion 608 of the DVS implant anchor 602). In view of FIG. 6, the angle may be an obtuse angle (e.g., in a range between about 90 degrees to about 180 degrees). Further, similar to FIG. 4, a length of the first implant anchor arm 609A and the second implant anchor arm 609B may be based on a cranial hole 603.

Figure 7:
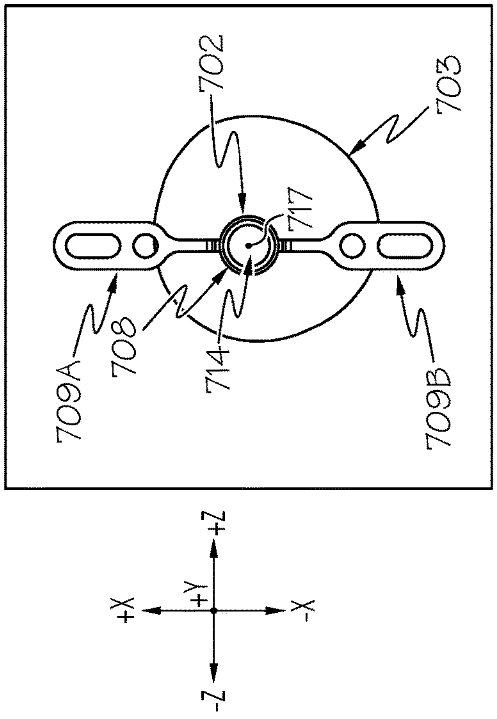
FIG. 7 depicts yet a further illustrative DVS implant anchor including a first implant anchor arm and a second implant anchor arm of equal length, according to one or more aspects shown and described herein.

FIG. 7 depicts yet a further illustrative DVS implant anchor 702 including a first implant anchor arm 709A and a second implant anchor arm 709B of equal length, according to various aspects of the present disclosure. Similar to as described in FIG. 4, the first implant anchor arm 709A may be positioned in a first direction (e.g., in the +X direction of the coordinate axes associated with FIGS. 4-7) and the second implant anchor arm 709B may be positioned at an angle relative to the first implant anchor arm 709A (e.g., about a center 717 of a DVS implant aperture 714 of the second portion 708 of the DVS implant anchor 702). In view of FIG. 7, the angle may be a substantially straight angle (e.g., about 180 degrees). Further, similar to FIG. 4, a length of the first implant anchor arm 709A and the second implant anchor arm 709B may be based on a cranial hole 703.

FIGS. 8-11 depict top views of a plurality of illustrative DVS implant anchors, each including a plurality of non-equal length implant anchor arms, according to various aspects of the present disclosure. Again, although FIGS. 8-11 each depict two implant anchor arms, it should be understood that the DVS implant anchors of the present disclosure may include at least one implant anchor arm and/or more than two implant anchor arms. Similar to as described herein, each of the plurality of DVS implant anchors of FIGS. 8-11 may be manufactured using a material (e.g., polymer (silicon rubber or the like), metal (stainless steel, titanium or the like), polyester, and/or the like) suitable for the uses described herein and may be manufactured via various processes (e.g., a blow molding process, an injection molding process, a machining process, a 3D printing process, and/or the like).

Figure 8:
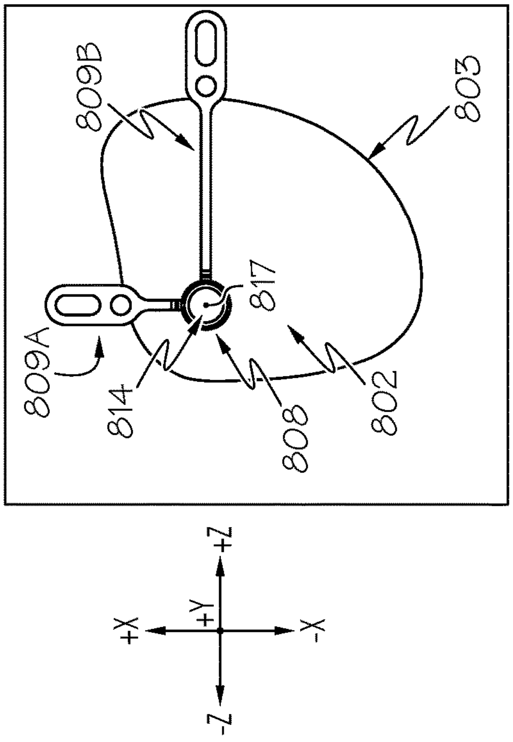
FIG. 8 depicts an illustrative DVS implant anchor including a first implant anchor arm and a second implant anchor arm of non-equal length, according to one or more aspects shown and described herein.

FIG. 8 depicts an illustrative DVS implant anchor 802 including a first implant anchor arm 809A and a second implant anchor arm 809B of non-equal length, according to various aspects of the present disclosure. Similar to as described in FIG. 5, the first implant anchor arm 809A may be positioned in a first direction (e.g., in the +X direction of the coordinate axes associated with FIGS. 8-11) and the second implant anchor arm 809B may be positioned at an angle relative to the first implant anchor arm 809A (e.g., about a center 817 of a DVS implant aperture 814 of the second portion 808 of the DVS implant anchor 802). In view of FIG. 8, the angle may be a substantially right angle (e.g., about 90 degrees). Further, similar to FIG. 5, a length of the first implant anchor arm 809A and the second implant anchor arm 809B may be based on a cranial hole 803.

Figure 9:
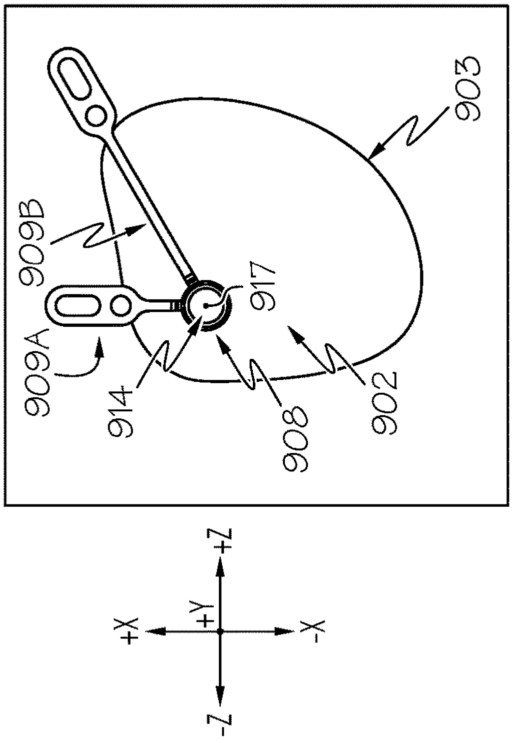
FIG. 9 depicts another illustrative DVS implant anchor including a first implant anchor arm and a second implant anchor arm of non-equal length, according to one or more aspects shown and described herein.

FIG. 9 depicts another illustrative DVS implant anchor 902 including a first implant anchor arm 909A and a second implant anchor arm 909B of non-equal length, according to various aspects of the present disclosure. Similar to as described in FIG. 4, the first implant anchor arm 909A may be positioned in a first direction (e.g., in the +X direction of the coordinate axes associated with FIGS. 8-11) and the second implant anchor arm 909B may be positioned at an angle relative to the first implant anchor arm 909A (e.g., about a center 917 of a DVS implant aperture 914 of the second portion 908 of the DVS implant anchor 902). In view of FIG. 9, the angle may be an acute angle (e.g., in a range between about 0 degrees and about 90 degrees). Further, similar to FIG. 4, a length of the first implant anchor arm 909A and the second implant anchor arm 909B may be based on a cranial hole 903.

Figure 10:
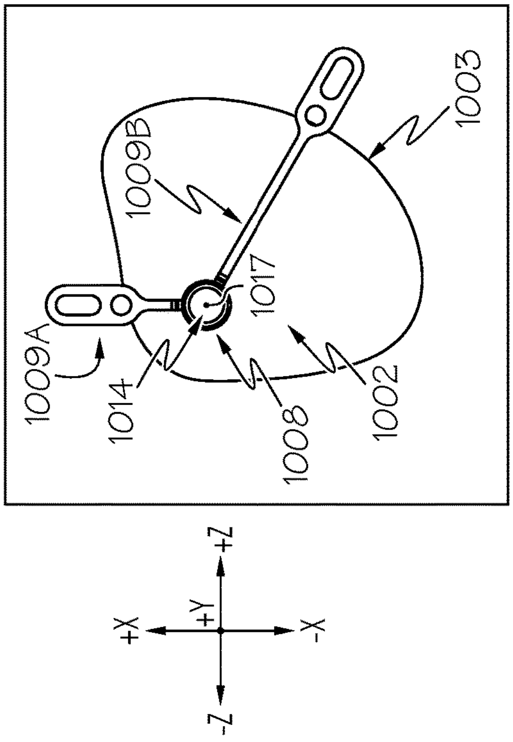
FIG. 10 depicts yet another illustrative DVS implant anchor including a first implant anchor arm and a second implant anchor arm of non-equal length, according to one or more aspects shown and described herein.

FIG. 10 depicts yet another illustrative DVS implant anchor 1002 including a first implant anchor arm 1009A and a second implant anchor arm 1009B of non-equal length, according to various aspects of the present disclosure. Similar to as described in FIG. 6, the first implant anchor arm 1009A may be positioned in a first direction (e.g., in the +X direction of the coordinate axes associated with FIGS. 8-11) and the second implant anchor arm 1009B may be positioned at an angle relative to the first implant anchor arm 1009A (e.g., about a center 1017 of a DVS implant aperture 1014 of the second portion 1008 of the DVS implant anchor 1002). In view of FIG. 10, the angle may be an obtuse angle (e.g., in a range between about 90 degrees to about 180 degrees). Further, similar to FIG. 4, a length of the first implant anchor arm 1009A and the second implant anchor arm 1009B may be based on a cranial hole 1003.

Figure 11:
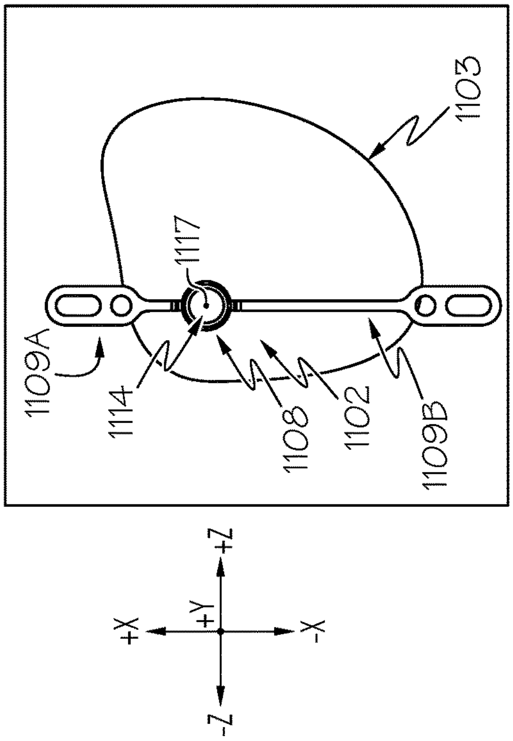
FIG. 11 depicts yet a further illustrative DVS implant anchor including a first implant anchor arm and a second implant anchor arm of non-equal length, according to one or more aspects shown and described herein.

FIG. 11 depicts yet a further illustrative DVS implant anchor 1102 including a first implant anchor arm 1109A and a second implant anchor arm 1109B of non-equal length, according to various aspects of the present disclosure. Similar to as described in FIG. 7, the first implant anchor arm 1109A may be positioned in a first direction (e.g., in the +X direction of the coordinate axes associated with FIGS. 8-11) and the second implant anchor arm 1109B may be positioned at an angle relative to the first implant anchor arm 1109A (e.g., about a center 1117 of a DVS implant aperture 1114 of the second portion 1108 of the DVS implant anchor 1102). In view of FIG. 11, the angle may be a substantially straight angle (e.g., about 180 degrees). Further, similar to FIG. 4, a length of the first implant anchor arm 1109A and the second implant anchor arm 1109B may be based on a cranial hole 1103.

Figure 12:
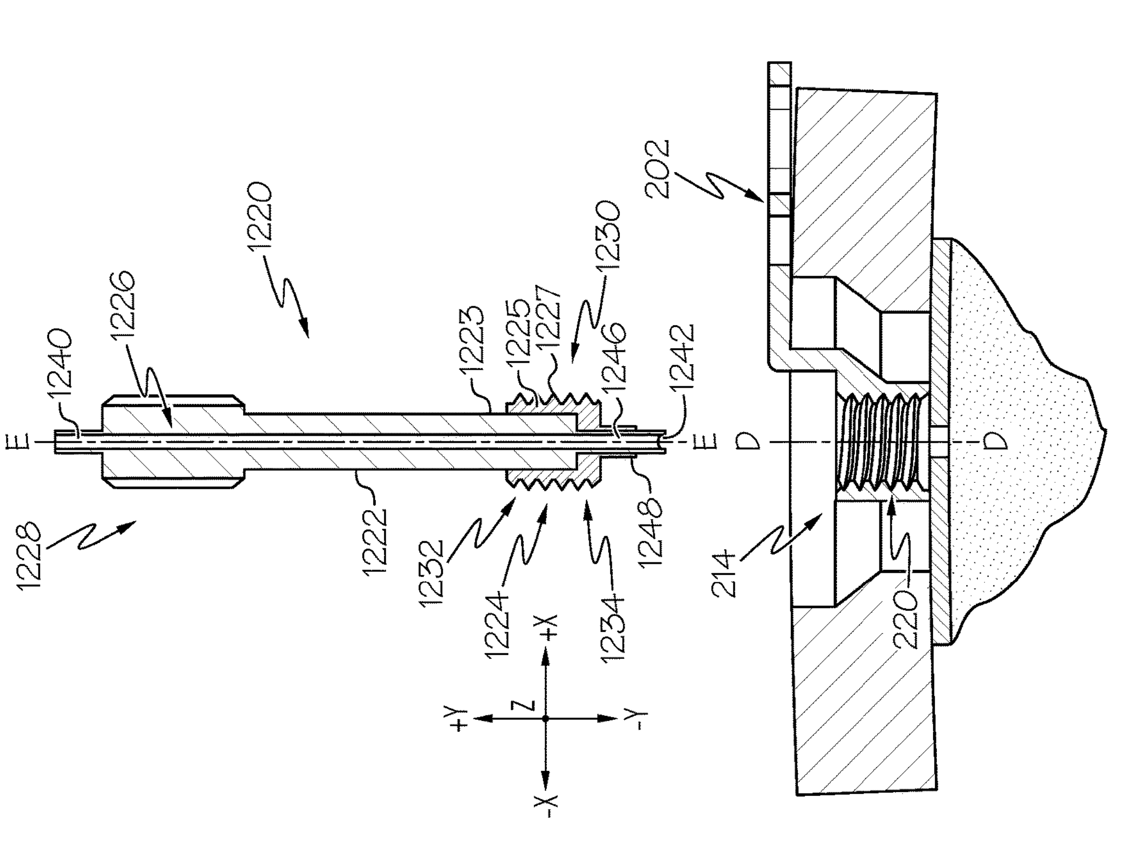
FIG. 12 depicts a cross-sectional view of an illustrative DVS implant placement assembly, according to one or more aspects shown and described herein.

FIG. 12 depicts a cross-sectional view of an illustrative DVS implant placement assembly 1220, according to various aspects of the present disclosure. Referring to FIG. 12, the DVS implant placement assembly 1220 may include a DVS implant driver 1222 and a DVS implant 1224. Each of the DVS implant driver 1222 and the DVS implant 1224 may be manufactured using a material (e.g., polymer (silicon rubber or the like), metal (stainless steel, titanium or the like), polyester, and/or the like) suitable for the uses described herein and may be manufactured via various processes (e.g., a blow molding process, an injection molding process, a machining process, a 3D printing process, and/or the like).

Figure 13:
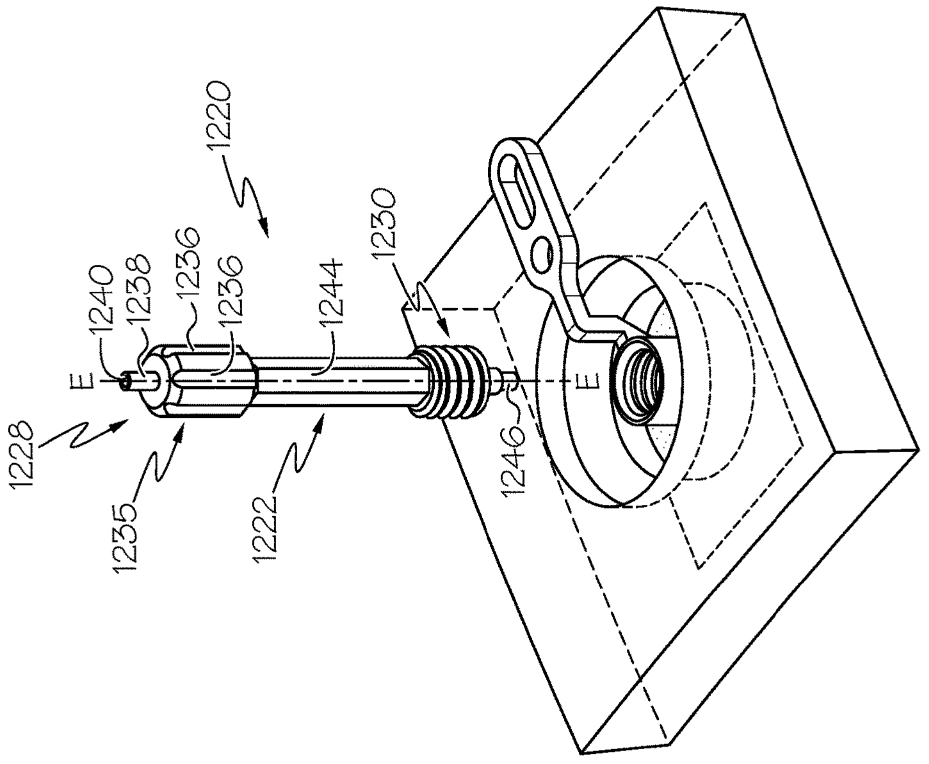
FIG. 13 depicts a perspective view of the illustrative DVS implant placement assembly of FIG. 12, according to one or more aspects shown and described herein.

In view of FIG. 12, a blood flow lumen 1226 may be defined within the DVS implant driver 1222 about a fifth axis (e.g., the E-E axis as depicted in FIG. 12) between an blood flow outlet 1240 at or near a first end 1228 (e.g., in the +Y direction of the coordinate axes of FIGS. 12 and 13) and a blood flow inlet 1242 at or near a second end 1230 (e.g., in the −Y direction of the coordinate axes of FIGS. 12 and 13). The DVS implant 1224 may include a DVS implant body 1225 defined by an internal surface 1223 and an external surface 1227, as described further herein.

FIG. 13 depicts a perspective view of the illustrative DVS implant placement assembly 1220 of FIG. 12, according to various aspects of the present disclosure. In light of FIG. 13, the first end 1228 of the DVS implant driver 1222 may include a finger grip 1235 configured for a user (e.g., surgeon) to grip and/or to rotate the DVS implant driver 1222 (e.g., in a clockwise direction and/or a counter-clockwise direction) about the fifth axis (e.g., axis E-E as depicted in FIG. 13). According to various aspects, the finger grip 1235 may include a plurality of radially extending protrusions 1236. In view of FIG. 13, a first cylindrical protrusion 1238 may extend in a first vertical direction (e.g., in the +Y direction of the coordinate axes of FIG. 13) from the finger grip 1235. The blood flow lumen 1226 (FIG. 12) may extend upward through the first cylindrical protrusion 1238 to the blood flow outlet 1240. Further in view of FIG. 13, a geometrically-shaped protrusion 1244 may extend in a second vertical direction (e.g., in the −Y direction of the coordinate axes of FIG. 13) from the finger grip 1235 toward the second end 1230. The blood flow lumen 1226 (FIG. 12) may similarly extend downward through the geometrically-shaped protrusion 1244 toward the blood flow inlet 1242. According to various aspects, the geometrically-shaped protrusion 1244 may be hexagonally shaped. Here, it should be understood that the geometrically-shaped protrusion 1244 may be of another shape profile (e.g., rectangular, octagonal, triangular, polygonal, and/or the like) to provide rotational control over the individual and joined components. Yet further in view of FIG. 13, at or near the second end 1230 of the DVS implant driver 1222 a second cylindrical protrusion 1246 (see also FIG. 12) may extend in the second vertical direction (e.g., in the −Y direction of the coordinate axes of FIG. 13) from the geometrically-shaped protrusion 1244. The blood flow lumen 1226 (FIG. 12) may extend downward through the second cylindrical protrusion 1246 to the blood flow inlet 1242. According to various aspects of the present disclosure, the second cylindrical protrusion 1246 may function as a needle configured to penetrate a subject's dura, as described further herein. It is understood that the portion of the implant that comprises the blood flow inlet 1242 may be available in different lengths and diameters to accommodate patient specific variables such as desired minimum or maximum CSF flow rates or pressure requirements and can be selected by the surgeon at the time of the surgery.

Referring again to FIG. 12, the DVS implant 1224 of the DVS implant placement assembly 1220 may include a first portion 1232 (e.g., in the +Y direction of the coordinate axes of FIG. 12) and a second portion 1234 (e.g., in the −Y direction of the coordinate axes of FIG. 12). Viewing FIG. 13, in light of FIG. 12, the first portion 1232 of the DVS implant 1224 may be shaped and/or dimensioned to receive the second end 1230 of the DVS implant driver 1222, and/or vice versa. More specifically, according to various aspects, the internal surface 1223 of the first portion 1232 of the DVS implant 1224 may mimic the geometrically-shaped protrusion 1244 of the DVS implant driver 1222. Similarly, the second portion 1234 of the DVS implant 1224 may be shaped and/or dimensioned to receive the second end 1230 of the DVS implant driver 1222, and/or vice versa. More specifically, according to various aspects, the internal surface 1223 of the second portion 1234 of the DVS implant 1224 may mimic the second cylindrical protrusion 1246 of the DVS implant driver 1222.

Still referring to FIG. 13, in light of FIG. 12, the first portion 1232 of the DVS implant 1224 may be shaped and/or dimensioned to be received within the DVS implant aperture 214 of the DVS implant anchor 202. More specifically, according to various aspects, threads may be defined on the external surface 1227 of the first portion 1232 of the DVS implant 1224 for threaded engagement with the threaded portion 220 of the DVS implant anchor 202. Furthermore, the external surface 1227 of the second portion 1234 of the DVS implant 1224 may be shaped and/or dimensioned for insertion within the subject's dura 114. More specifically, according to various aspects, the external surface 1227 of the second portion 1234 may concentrically surround at least a portion of the second cylindrical protrusion 1246 of the DVS implant driver 1222 to form a CSF outlet tip 1248 of the DVS implant 1224, as described herein. According to some aspects the inner diameter and/or outer diameter of the CSF outlet tip 1248 may be constant throughout various sizing ranges. Furthermore, although the CSF outlet tip 1248 is illustrated as pointing straight downward (e.g., in the −Y direction of the coordinate axes of FIG. 12) the present disclosure is not so limited. For example, in some aspects, the CSF outlet tip 1248 may be curved (e.g., away from the −Y direction toward the X-Z plane of the coordinate axes of FIG. 12). In such aspects, for example, the CSF outlet tip 1248 may also be curved to point into or against the blood flow of the subject's DVS 112.

Figure 14:
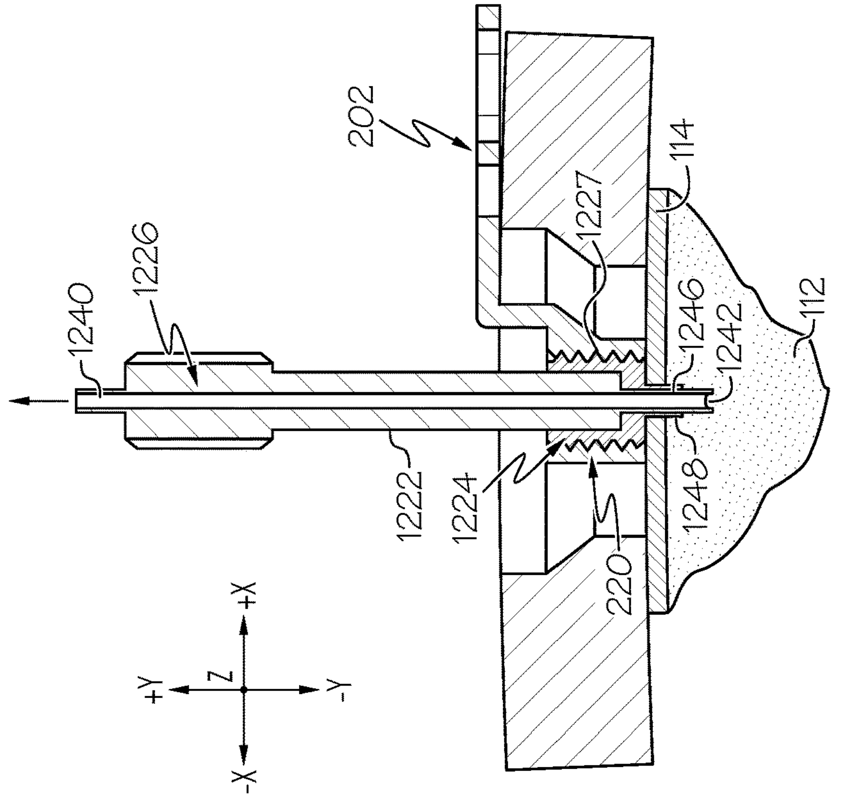
FIG. 14 depicts a cross-sectional view of the illustrative DVS implant placement assembly of FIG. 12 coupled to the DVS implant anchor of FIG. 2A, according to one or more aspects shown and described herein.

FIG. 14 depicts a cross-sectional view of the illustrative DVS implant placement assembly 1220 of FIG. 12 coupled to the DVS implant anchor 202 of FIG. 2A, according to various aspects of the present disclosure. Referring to FIG. 14, threads defined on the external surface 1227 of the DVS implant 1224 have been threadedly engaged, in a first direction (e.g., in a clockwise-direction if right-handed threads, in a counter-clockwise direction if left-handed threads) with the threaded portion 220 of the DVS implant anchor 202 to advance the DVS implant 1224 in a second vertical direction (e.g., in the −Y direction of the coordinate axes of FIG. 14) toward and penetratingly through the subject's dura 114. More specifically, as the DVS implant 1224 is controllably advanced/rotated into the DVS implant anchor 202, the second cylindrical protrusion 1246 of the coupled DVS implant driver 1222 may controllably pierce and/or penetrate the subject's dura 114. In view of FIG. 14, once the second cylindrical protrusion 1245 pierces and/or penetrates the subject's dura 114, blood (e.g., from the subject's DVS 112) may flow into the blood flow inlet 1242 of the DVS implant driver 1222, up through (e.g., in the +Y direction of the coordinate axes of FIG. 14) the blood flow lumen 1226 of the DVS implant driver 1222, and out of the blood flow outlet 1240 of the DVS implant driver 1222 (e.g., generally depicted via an arrow in FIG. 14). Such blood flow may confirm the location of the subject's DVS 112. Accordingly, second cylindrical protrusion 1246 may be controllably advanced (e.g., via the DVS implant driver 1222 and the DVS implant 1224) through the DVS implant anchor 202 until such blood flow is present. Further in view of FIG. 14, after the second cylindrical protrusion 1246 initially pierces and/or penetrates the subject's dura 114, the CSF outlet tip 1248 (e.g., concentrically surrounding the second cylindrical protrusion 1246) of the DVS implant 1224 may controllably pierce and/or penetrate the subject's dura 114 until the DVS implant 1224 is controllably seated within the subject's DVS 112 and against (e.g., through, on top of, and/or in contact with) the subject's dura 114 (e.g., as depicted in FIG. 14) or, in the case where an adhesive is used through, on top of, and/or in contact with the pad that is, in turn, in contact with the dura. In some aspects, after blood flow confirmation, the DVS implant 1224 may be controllably advanced/rotated into the DVS implant anchor 202 a metered amount (e.g., one more full rotation, and/or the like). A pitch of the threads of the DVS implant 1124 and/or the threaded portion 220 of the DVS implant anchor 202 may control the amount by which the second cylindrical protrusion 1246 and/or the CSF outlet tip 1248 pierces and/or penetrates the subject's dura 114. Once the DVS implant 1224 is seated within the subject's DVS 112 and/or against the subject's dura 114, advancement/rotation of the DVS implant 1224 into the DVS implant anchor 202 is ceased. In light of FIG. 14, although the DVS implant 1224 is illustrated as threaded into/through (e.g., in the −Y direction of the coordinate axes of FIG. 14) all the threaded portion 220 of the DVS implant anchor 202, it should be appreciated that blood flow may be present and further advancement of the DVS implant 1224 ceased prior to all the threaded portion 220 of the DVS implant anchor 202 being utilized. It is also understood that the threads used on the DVS implant 1224 and the threaded portion 220 may be of a locking design that will prevent any unintentional relative movement between the DVS implant 1224 and the threaded portion 220.

Figure 15:
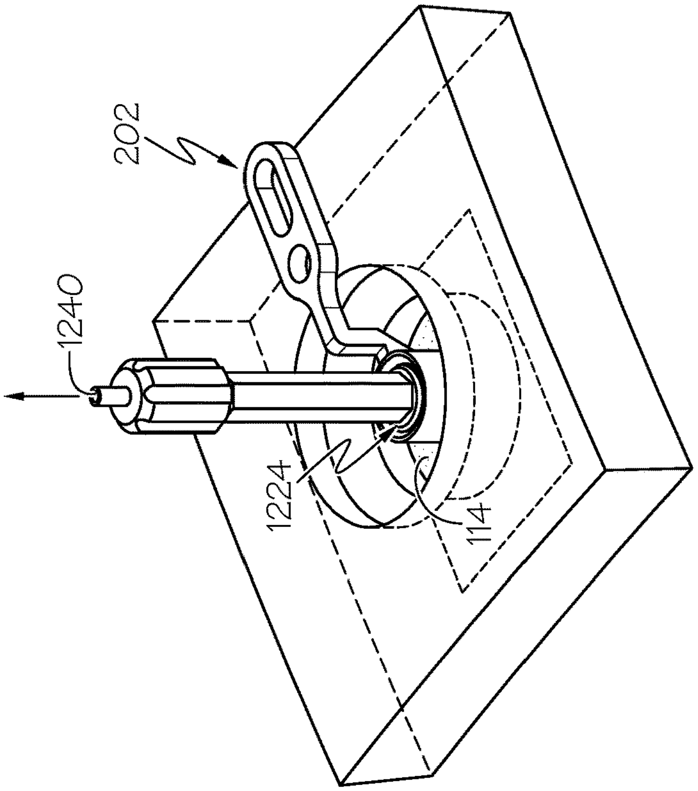
FIG. 15 depicts a perspective view of the illustrative DVS implant placement assembly of FIG. 12 coupled to the DVS implant anchor of FIG. 2A, according to one or more aspects shown and described herein.

FIG. 15 depicts a perspective view of the illustrative DVS implant placement assembly 1220 of FIG. 12 coupled to the DVS implant anchor 202 of FIG. 2A, according to various aspects of the present disclosure. Similar to FIG. 14, blood may flow out of the blood flow outlet 1240 (e.g., generally depicted via an arrow in FIG. 15) to confirm access to the subject's DVS 112 through the subject's dura 114. Once blood flow is present and the DVS implant 1224 is seated as described herein, the DVS implant 1224 is in an installed position within the DVS implant anchor 202, as depicted in FIG. 15.

Figure 16:
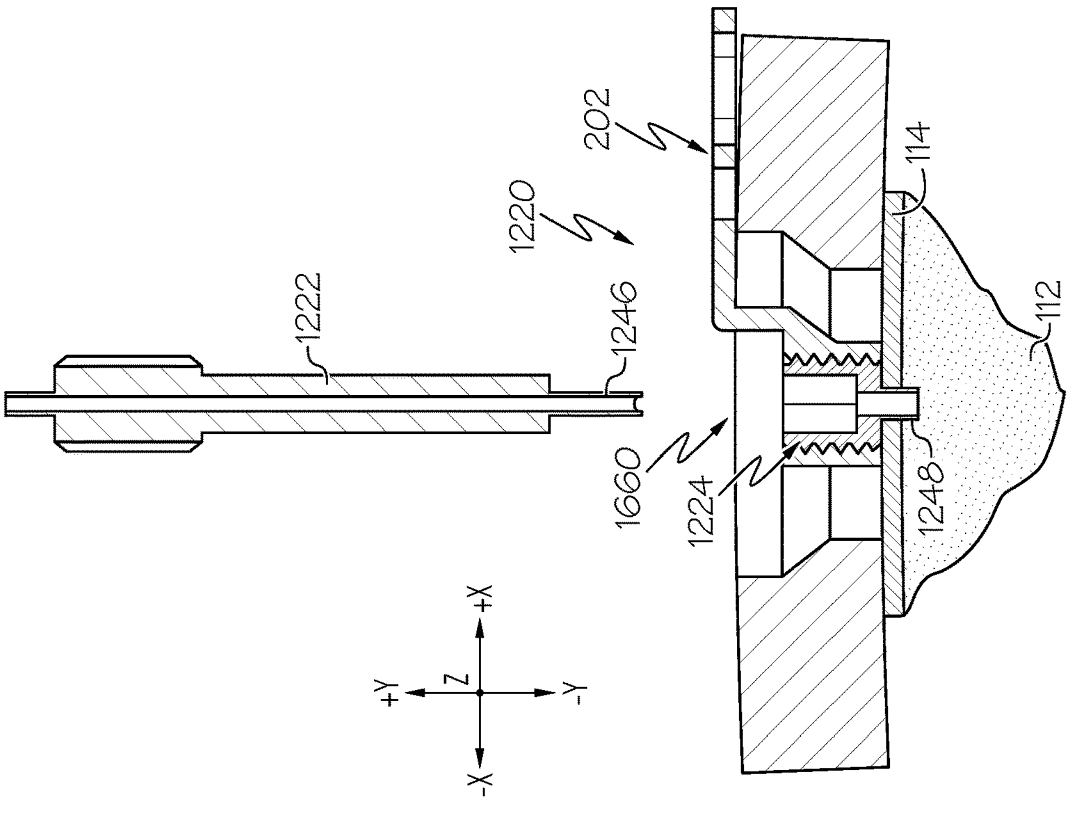
FIG. 16 depicts a cross-sectional view of the illustrative DVS implant driver of the DVS implant placement assembly decoupled from the DVS implant of the DVS implant placement assembly, according to one or more aspects shown and described herein.

FIG. 16 depicts a cross-sectional view of the illustrative DVS implant driver 1222 of the DVS implant placement assembly 1220 decoupled from the DVS implant 1224 of the DVS implant placement assembly 1220, according to various aspects of the present disclosure. In view of FIG. 16, the DVS implant placement assembly 1220 is configured such that the DVS implant driver 1222 (e.g., and its second cylindrical protrusion 1246) may be decoupled and/or removed from the DVS implant 1224 after the seating and/or placement of the DVS implant 1224 in the installed position. In light of FIG. 16, the CSF outlet tip 1248 of the DVS implant 1224 remains inserted into the subject's DVS 112 through the subject's dura 114. According to various aspects described herein, a DVS implant subassembly 1660 may include the DVS implant 1224 coupled, in its installed position, within the DVS implant anchor 202.

Figure 17:
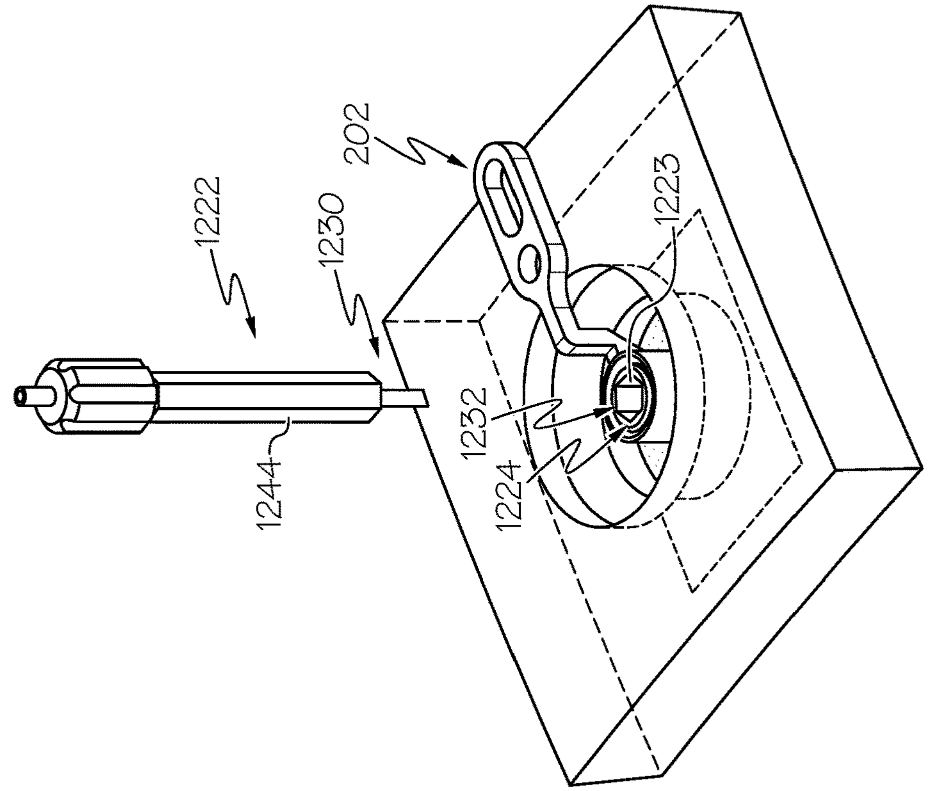
FIG. 17 depicts a perspective view of the illustrative DVS implant driver of the DVS implant placement assembly decoupled from the DVS implant of the DVS implant placement assembly, according to one or more aspects shown and described herein.

FIG. 17 depicts a perspective view of the illustrative DVS implant driver 1222 of the DVS implant placement assembly 1220 decoupled from the DVS implant 1224 of the DVS implant placement assembly 1220, according to various aspects of the present disclosure. Referring to FIG. 17, as described herein, the first portion 1232 of the DVS implant 1224 may be shaped and/or dimensioned to receive the second end 1230 of the DVS implant driver 1222, and/or vice versa. As depicted in FIG. 17, according to various aspects, the internal surface 1223 of the first portion 1232 of the DVS implant 1224 may mimic the geometrically-shaped protrusion 1244 of the DVS implant driver 1222 (e.g., hexagonally shaped). Here, it should be understood that the geometrically-shaped protrusion 1244 may be of another shape profile (e.g., rectangular, octagonal, triangular, polygonal, and/or the like) and the internal surface 1223 of the first portion 1232 of the DVS implant 1224 may mimic that shape profile.

Figure 18:
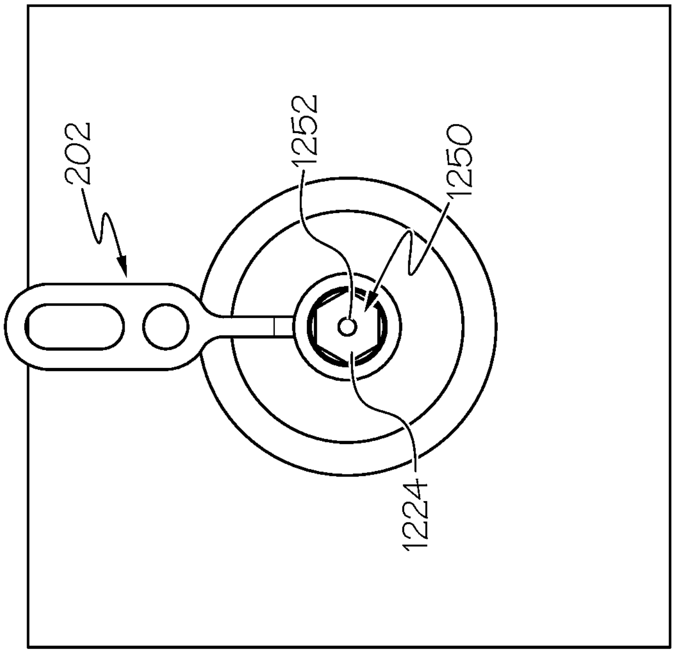
FIG. 18 depicts a top view of the illustrative DVS implant seated within the DVS implant anchor, according to one or more aspects shown and described herein.

FIG. 18 depicts a top view of the illustrative DVS implant 1224 seated within the DVS implant anchor 202, according to various aspects of the present disclosure. Referring to FIG. 18, a CSF flow aperture 1250, having an internal surface 1252, may be defined in the CSF outlet tip 1248 (see FIG. 16) for the flow of CSF into the subject's DVS 112 (FIG. 16).

Figure 19:
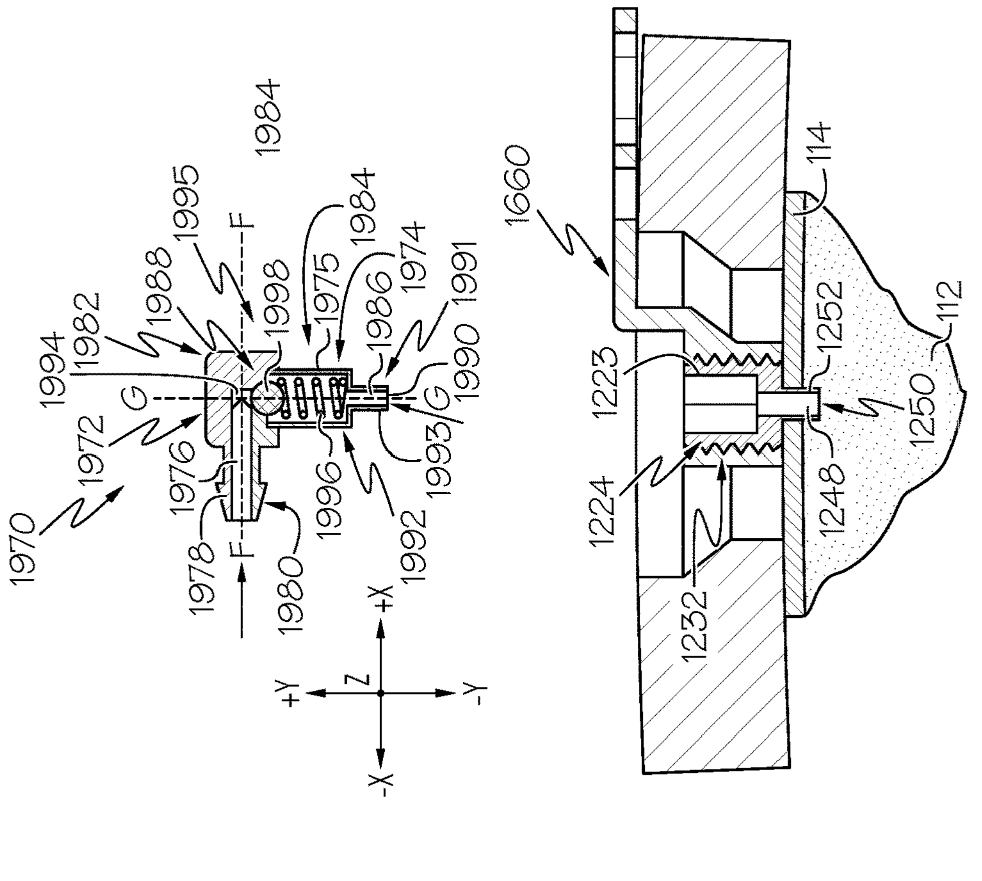
FIG. 19 depicts a cross-sectional view of an illustrative CSF pressure and flow control (PFC) device insertable within the DVS implant subassembly of FIG. 16, according to one or more aspects shown and described herein.

FIG. 19 depicts a cross-sectional view of an illustrative CSF pressure and flow control (PFC) device 1970 insertable (e.g., generally depicted by an arrow in FIG. 19) within the DVS implant subassembly 1660 of FIG. 16, according to various aspects of the present disclosure. The PFC device 1970 and its various components, as described herein, may be manufactured using a material (e.g., polymer (silicon rubber or the like), metal (stainless steel, titanium or the like), polyester, anti-coagulation materials, and/or the like) suitable for the uses described herein and may be manufactured via various processes (e.g., a blow molding process, an injection molding process, a machining process, a 3D printing process, and/or the like).

Referring to FIG. 19, the PFC device 1970 may include a CSF inlet portion 1972 and a CSF outlet portion 1974. Referring to FIG. 19, the PFC device 1970 may also include an integrated pump reservoir mechanism for at least one of collecting, purging, testing, dispensing medication or cleaning all or a portion of the PFC. A first CSF flow lumen 1976 may be defined within the CSF inlet portion 1972 about a sixth axis (e.g., the F-F axis as depicted in FIG. 19) from a PFC inlet tip 1978 at a first portion 1980 (e.g., in the −X direction of the coordinate axes of FIG. 19) to a central portion 1982 of the CSF inlet portion 1972. CSF may flow into (e.g., generally depicted by an arrow in FIG. 19) the CSF flow lumen 1976, as described herein. A mechanical device chamber 1984 and second CSF flow lumen 1986 may be defined within the CSF outlet portion 1974 about a seventh axis (e.g., the G-G axis as depicted in FIG. 19) from a first portion 1988 (e.g., in the +Y direction of the coordinate axes of FIG. 19) to a PFC outlet tip 1990 of a PFC outlet protrusion 1991 at a second portion 1992 (e.g., in the −Y direction of the coordinate axes of FIG. 19) of the CSF outlet portion 1974. According to various aspects, the PFC outlet tip 1990 may be sized (e.g., inner diameter) for a predetermined CSF flow rate at a predetermined pressure (e.g., based on the subject, e.g., adult, juvenile, and/or the like). In view of FIG. 19, the first CSF flow lumen 1976 may be fluidically coupled to the mechanical device chamber 1984 and the second CSF flow lumen 1986 via a funnel-shaped coupler 1994. In light of FIG. 19, the mechanical device chamber 1984 may be shaped and/or sized to house a mechanical device 1996 (e.g., a spring and/or the like). Further, a fluid stop device 1998 (e.g., ball) may be forcibly positioned, via the mechanical device 1996 against the funnel of the funnel-shaped coupler 1994 to controllably prevent CSF fluid flow and/or blood flow. The fluid stop device 1998 and the funnel-shaped coupler 1994 and/or the mechanical device 1996 may be referenced herein as a ball valve 1995, for example. However, it should be understood that the mechanical device 1996 may alternatively be a slit valve, a pinch valve, and any other suitable known or yet to be developed valve. According to various aspects, the ball valve 1995 may be configured as a one-way valve (e.g., such that CSF is able to flow into the DVS while blood is prevented from flowing out of the DVS).

Still referring to FIG. 19, an external surface 1975 of the mechanical device chamber 1984 of the CSF outlet portion 1974 may be shaped and/or dimensioned to slidingly fit within the internal surface 1223 of the first portion 1232 of the DVS implant 1224, and/or vice versa. In some aspects, the external surface 1975 may be shaped and/or dimensioned to interferingly fit within the internal surface 1223 to fittingly retain and/or seal the PFC device 1970 within the DVS implant subassembly 1660. Similarly, an external surface 1993 of the PFC outlet protrusion 1991 of the CSF outlet portion 1974 may be shaped and/or dimensioned to slidingly fit within the internal surface 1252 of the CSF flow aperture 1250 defined in the CSF outlet tip 1248 of the DVS implant 1224, or vice versa. More specifically, according to various aspects, the external surface 1993 may concentrically fit within at least a portion of the CSF outlet tip 1248 of the DVS implant 1224. In some aspects, the external surface 1993 may be shaped and/or dimensioned to interferingly fit within the internal surface 1252 to fittingly retain and/or seal the PFC device 1970 within the DVS implant subassembly 1660.

PFC-DVS drain assembly 1970 contains a drain (e.g. CSF outlet) component, with a length between 1 to 2.5 mm and an inner diameter ranging from 0.2 mm to 2 mm, that is to be placed into the superior portion of a DVS and penetrating the inner surface of the superior wall by 0.5 mm to 3 mm. The CSF outlet 1248 can be placed with a specific orientation with regard to the direction of blood flow between +90/0/−90 degrees where 0 degrees is the drain opening parallel to the blood flow and +90 degrees where the drain opening is directed into the blood flow and −90 degrees where the drain opening with the blood flow (e.g. downstream) and all angles in-between. The PFC-DVS drain assembly 1970 also contains an inlet portion for connection to the CSF source and a body 1970 between the DVS drain and DVS inlet that optionally contains a reservoir (e.g. for medication delivery or fluid sample collection) and/or a pressure differential controlled valve, and/or a flow control method and/or various measurement devices that can record pressure, flow volume/rate, and patient position relative to a previous position (e.g. from lying down on a bed to standing up)

Figure 20:
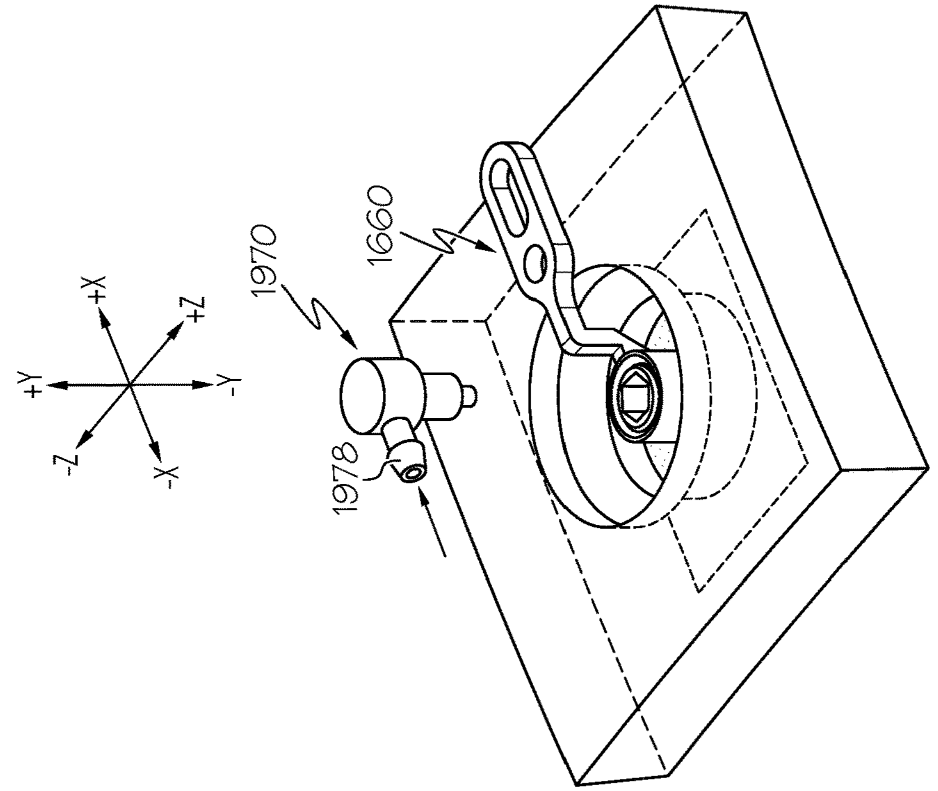
FIG. 20 depicts a perspective view of the illustrative PFC device of FIG. 19 insertable within the DVS implant subassembly 1660 of FIG. 16, according to one or more aspects shown and described herein.

FIG. 20 depicts a perspective view of the illustrative PFC device 1970 of FIG. 19 insertable (e.g., generally depicted by an arrow in FIG. 20) within the DVS implant subassembly 1660 of FIG. 16, according to various aspects of the present disclosure. As described herein, CSF may flow into (e.g., generally depicted by an arrow in FIG. 20) the PFC inlet tip 1978 of the PFC device 1970. According to aspects of the present disclosure, insertion of the PFC device 1970 into the DVS implant subassembly 1660 may prevent (e.g., via the ball valve 1995) blood from flowing (e.g., in the +Y direction of the coordinate axes of FIG. 20) from the subject's DVS 112.

FIG. 21 depicts a cross-sectional view of the ball valve 1995 of the PFC device 1970 of FIG. 19 in a closed position, according to various aspects of the present disclosure. Referring to FIG. 21, a CSF source tube 2102 may be coupled to the PFC inlet tip 1978 of the PFC device 1970. The CSF source tube 2102 be manufactured using a material (e.g., polymer (silicon rubber or the like), a flexible metal (stainless steel, titanium or the like), a polyester, an anti-coagulation material, and/or the like) suitable for the uses described herein and may be manufactured via various processes (e.g., an extrusion process, a blow molding process, an injection molding process, a machining process, a 3D printing process, and/or the like). A retention feature 1979 (e.g., barb, or the like) may be defined on the PFC inlet tip 1978 to releasably couple the CSF source tube 2102 to the PFC device 1970. In view of FIG. 21, in the closed position, the fluid stop device 1998 is forcibly positioned, via the mechanical device 1996, against the funnel of the funnel-shaped coupler 1994 (see FIG. 22, hidden by fluid stop device 1998 in FIG. 21) to prevent CSF fluid flow (e.g., in the +X direction of the coordinate axes of FIGS. 21 and 22) from the CSF source tube 2102, through the PFC inlet tip 1978, and through the CSF flow lumen 1976 of the PFC device 1970. Furthermore, in the closed position, the fluid stop device 1998 is forcibly positioned, via the mechanical device 1996, against the funnel of the funnel-shaped coupler 1994 (FIG. 22) to prevent blood flow (e.g., in the +Y direction of the coordinate axes of FIGS. 21 and 22) from the subject's DVS 112, through the CSF outlet tip 1248 of the DVS implant 1224, and through the second CSF flow lumen 1986 of the PFC outlet tip 1990 and the mechanical device chamber 1984 of the PFC device 1970. According to various aspects, the ball valve 1995 may remain in the closed position until there is sufficient CSF pressure and/or flow rate to overcome the mechanical device 1996 such that the CSF may drain into the subject's DVS 112.

Figure 22:
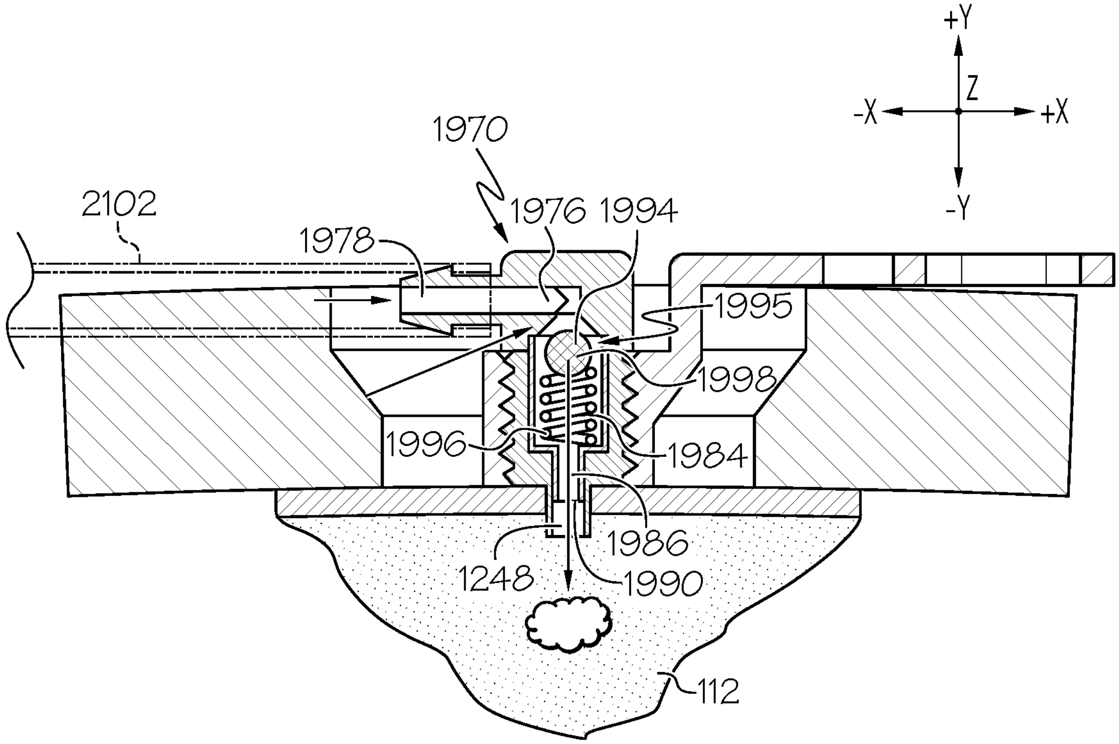
FIG. 22 depicts a cross-sectional view of the ball valve of the PFC device of FIG. 19 in an open position, according to one or more aspects shown and described herein.

FIG. 22 depicts a cross-sectional view of the ball valve 1995 of the PFC device 1970 of FIG. 19 in an open position, according to various aspects of the present disclosure. Referring to FIG. 22, in the open position, CSF delivered via the CSF source tube 2102 is sufficient (e.g., at a predetermined pressure and/or flow rate) to overcome the mechanical device 1996 such that the fluid stop device 1998 is dislodged from the funnel of the funnel-shaped coupler 1994 (see FIG. 22 in light of FIG. 21, mechanical device 1996 relatively compressed) to permit CSF fluid flow (e.g., in the +X direction of the coordinate axes of FIGS. 21 and 22) from the CSF source tube 2102, through the PFC inlet tip 1978, through the CSF flow lumen 1976, through the funnel-shaped coupler 1994, through the mechanical device chamber 1984, through the second CSF flow lumen 1986 of the PFC outlet tip 1990, and through the CSF outlet tip 1248 into the subject's DVS 112 (e.g., generally depicted via an arrow in FIG. 22). Furthermore, in the open position, the predetermined pressure and/or flow rate of the CSF may prevent blood from the subject's DVS 112 from flowing in a direction reverse of that as described herein.

Figure 23:
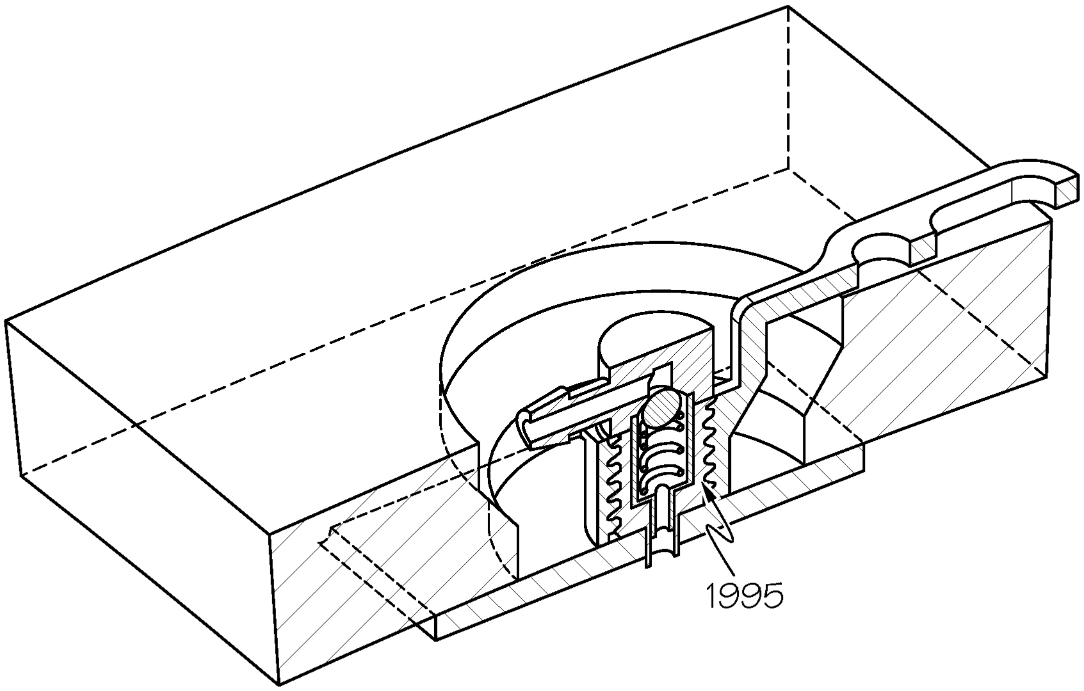
FIG. 23 depicts a perspective view of the PFC device of FIG. 21, according to one or more aspects shown and described herein.
Figure 24:
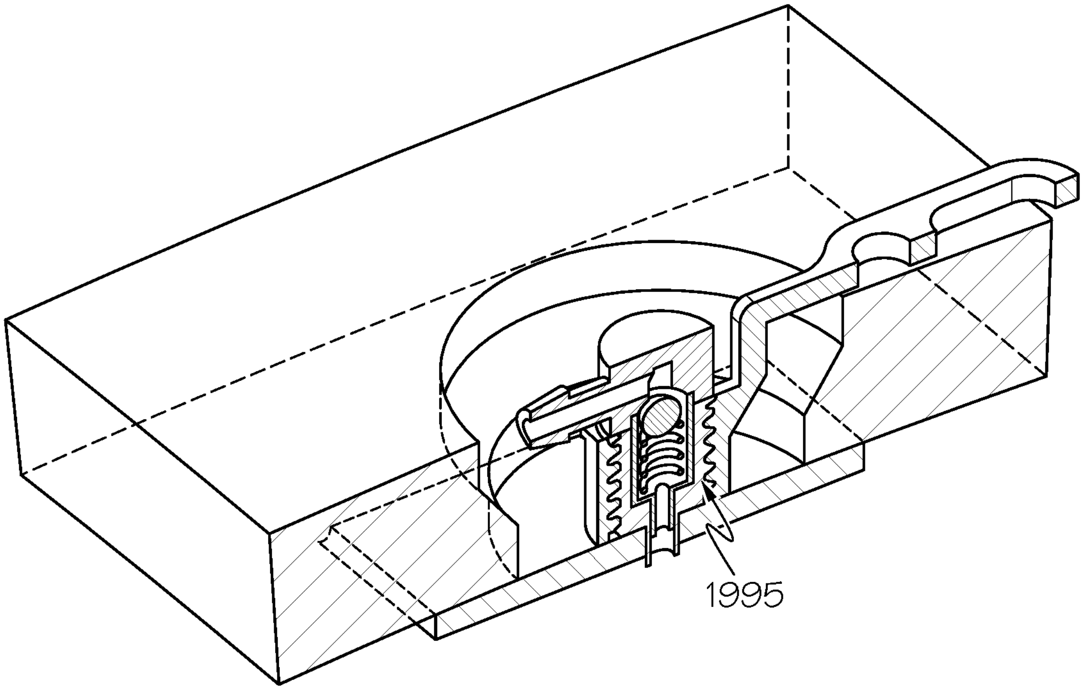
FIG. 24 depicts a perspective view of the PFC device of FIG. 22, according to one or more aspects shown and described herein.

FIG. 23 depicts a perspective view of the PFC device of FIG. 21 and FIG. 24 depicts a perspective view of the PFC device of FIG. 22, according to various aspects of the present disclosure. More specifically, FIG. 23 depicts the ball valve 1995 in the closed position and FIG. 24 depicts the ball valve 1995 in the open position.

Figure 26:
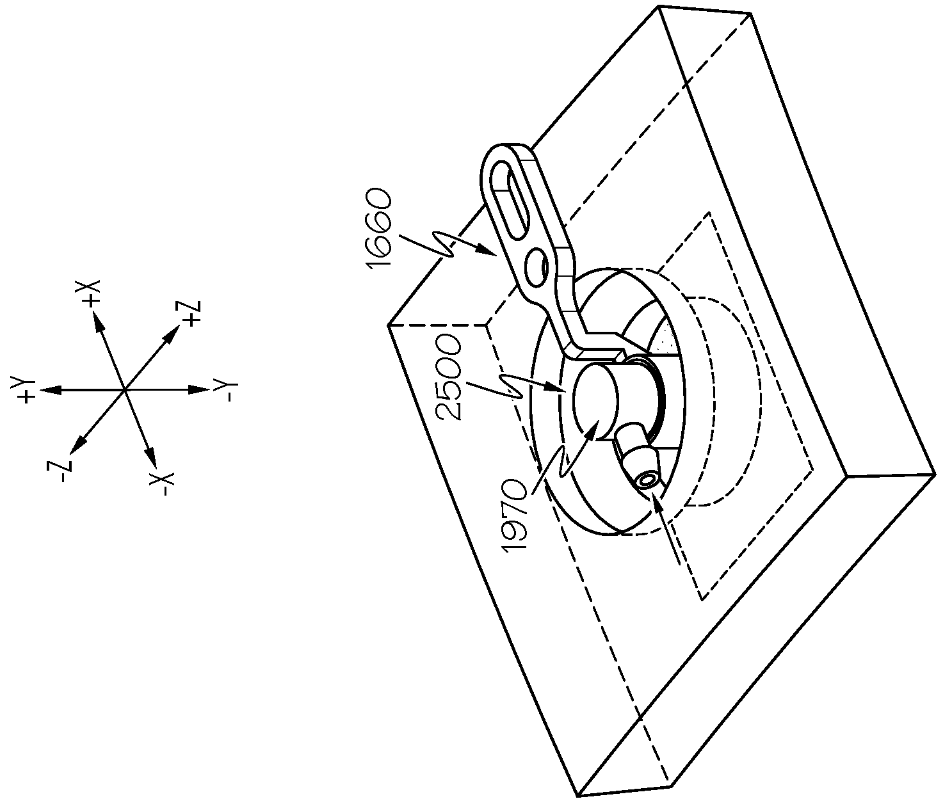
FIG. 26 depicts a perspective view of the PFC-DVS drain assembly of FIG. 25, according to one or more aspects shown and described herein.
Figure 25:
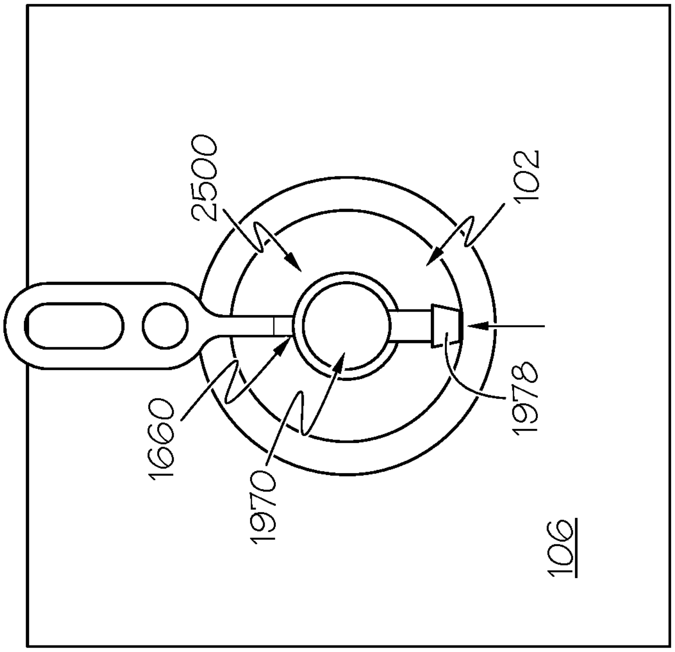
FIG. 25 depicts a top view of the PFC device of FIG. 19 inserted within the DVS implant subassembly of FIG. 16 to form a PFC-DVS drain assembly, according to one or more aspects shown and described herein.

FIG. 25 depicts a top view of the PFC device 1970 of FIG. 19 inserted within the DVS implant subassembly 1660 of FIG. 16 to form a PFC-DVS drain assembly 2500, according to various aspects of the present disclosure. Referring to FIG. 25, the PFC device 1970, when inserted within the DVS implant subassembly 1660, may be referred to herein as a PFC-DVS drain assembly 2502. As illustrated in FIG. 23, CSF (e.g., generally depicted via an arrow in FIG. 23) may flow into the PFC inlet tip 1978 to drain through the DVS burr hole 102 in the subject's skull 106 and into the subject's DVS 112. FIG. 26 depicts a perspective view of the PFC-DVS drain assembly 2500 of FIG. 25, according to various aspects of the present disclosure.

Figure 27:
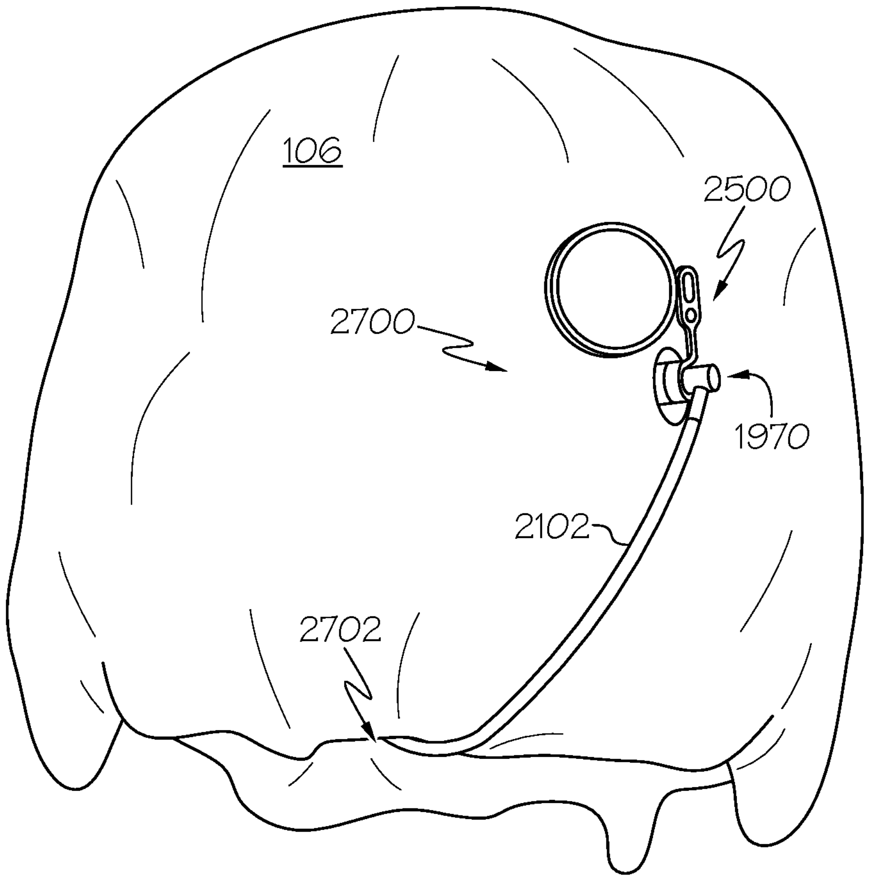
FIG. 27 depicts a perspective view of the illustrative PFC-DVS drain assembly of FIG. 25 coupled to a posterior subject skull with a CSF source tube coupled to the PFC device of the PFC-DVS drain assembly, according to one or more aspects shown and described herein.

FIG. 27 depicts a perspective view of the illustrative PFC-DVS drain assembly 2500 of FIG. 25 coupled to a posterior subject skull 106 with a CSF source tube 2102 coupled to the PFC device 1970 of the PFC-DVS drain assembly 2500, according to various aspects of the present disclosure. According to various aspects of the present disclosure, the PFC-DVS drain assembly 2500 when coupled to a CSF source 2702 (e.g., cisterna magna) via the CSF source tube 2102 may be referred to herein as a single burr hole hydrofix implant 2700. According to various aspects, the CSF source tube 2102 may include a silicone tube. A penny is depicted in FIG. 27 to illustrate example dimensions of the various single burr hole hydrofix implant 2700 components. Here, it should be understood that the components (e.g., DVS implant anchor 202, DVS implant 1224, the PFC device 1970, the CSF source tube 2102, and/or the like) of the single burr hole Hydrofix implant 2700 are modular in nature. Accordingly, any component of the single burr hole Hydrofix implant 2700 may be serviced and/or replaced as needed with less risk to the subject (e.g., via a no or minimally invasive procedure).

Figure 28:
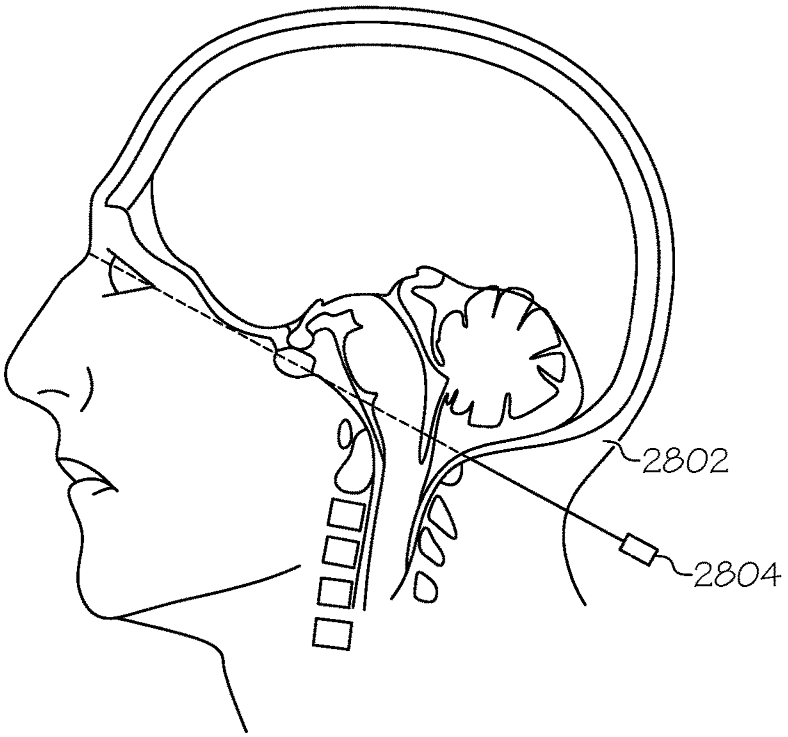
FIG. 28 depicts a sagittal view of a subject illustrating the location of the cisterna magna, according to one or more aspects shown and described herein.

In light of FIG. 27, a CSF source 2702 may be a subject's cisterna magna as shown or lateral ventricle or SAS or spinal cord/column. FIG. 28 depicts a sagittal view of a subject illustrating the location of the cisterna magna 2802, according to various aspects of the present disclosure. In some aspects, the cisterna magna 2802 may be difficult to access (e.g., due to muscle and/or the like) as an adequate source or pool of CSF. Accordingly, various procedures and/or tools may be used to access a subject's cisterna magna. In light of FIG. 28, a surgeon may use a needle 2804 to access the cisterna magna 2802.

Figure 29:
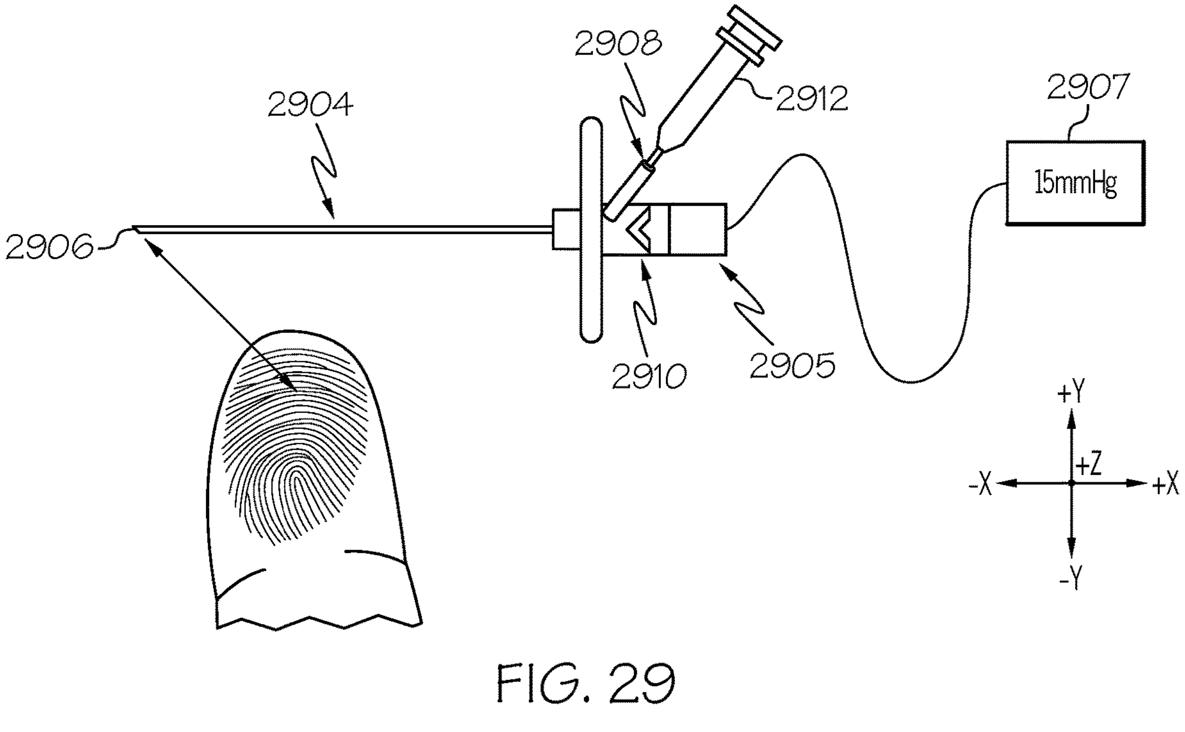
FIG. 29 depicts an illustrative needle to access CSF located at a subject's cisterna magna, according to one or more aspects shown and described herein.

FIG. 29 depicts an illustrative needle 2904 to access CSF located at a subject's cisterna magna 2802, according to various aspects of the present disclosure. Referring to FIG. 29, the needle 2904 (e.g., a modified Tuohy needle) may include a stylet 2905 having an optical pressure transducer 2906 (e.g., a fiber optic pressure sensor, FOP-MIV, FOP-260, FOP-M200, and/or the like) positioned at a first end (e.g., in the −X direction of the coordinate axes of FIG. 29), a side port 2908 positioned at and/or near a second end (e.g., in the +X direction of the coordinate axes of FIG. 29), and a one-way valve 2910 positioned at and/or near the second end. According to various aspects, the stylet 2905 may couple to a user interface 2907 to view a CSF pressure (e.g., 15 mm Hg), the side port 2908 may be used to confirm CSF (e.g., via a syringe 2912) and the one-way valve 2910 may be weak enough to open upon insertion of a CSF source tube 2102 (FIG. 21) but strong enough to prevent copious amounts of CSF from leaking out (e.g., when the CSF source tube 2102 is not inserted). According to various aspects, the stylet 2905 is sized and/or dimensioned such that it does not fill the entire orifice of the needle 2904 (e.g., so that CSF can pass).

Figure 30:
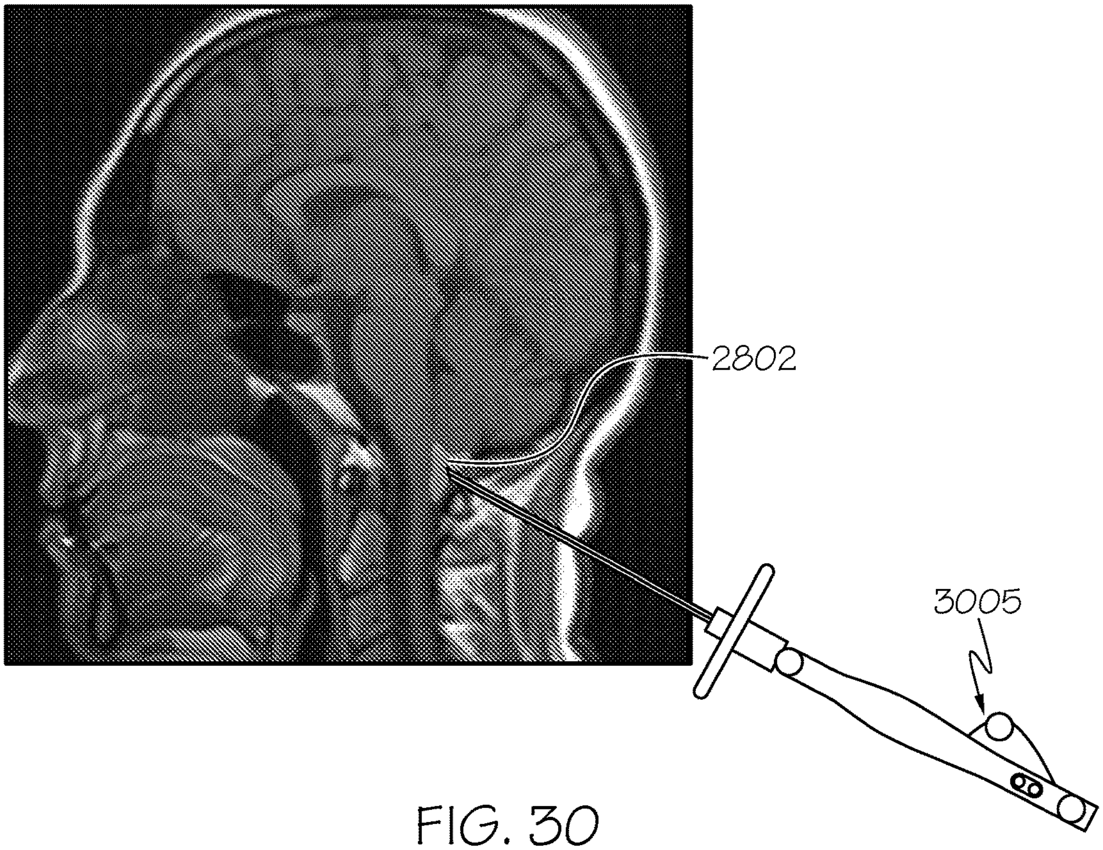
FIG. 30 depicts a sagittal view of a subject illustrating a navigation of the needle of FIG. 29, according to one or more aspects shown and described herein.

FIG. 30 depicts a sagittal view of a subject illustrating a navigation of the needle 2904 of FIG. 29, according to various aspects of the present disclosure. Referring to FIG. 30, the needle 2904 may be navigatingly inserted (e.g., via a positionally encoded (e.g. wired, optical, RF) handle incorporating a pressure measuring stylet 3005) into the cisterna magna 2802. The higher fluid pressure of the CSF, present in patients with hydrocephalus, is indicating by a rise in the pressure reading once the needle enters the cisterna magna. As depicted in FIG. 30, the cisterna magna 2802 is positioned over the arch of the C1 vertebra. According to various aspects, CSF may be drawn through the needle 2904 to confirm insertion into the cisterna magna 2802 (see FIG. 29, e.g., via side port 2908 and a syringe 2912).

Figure 31:
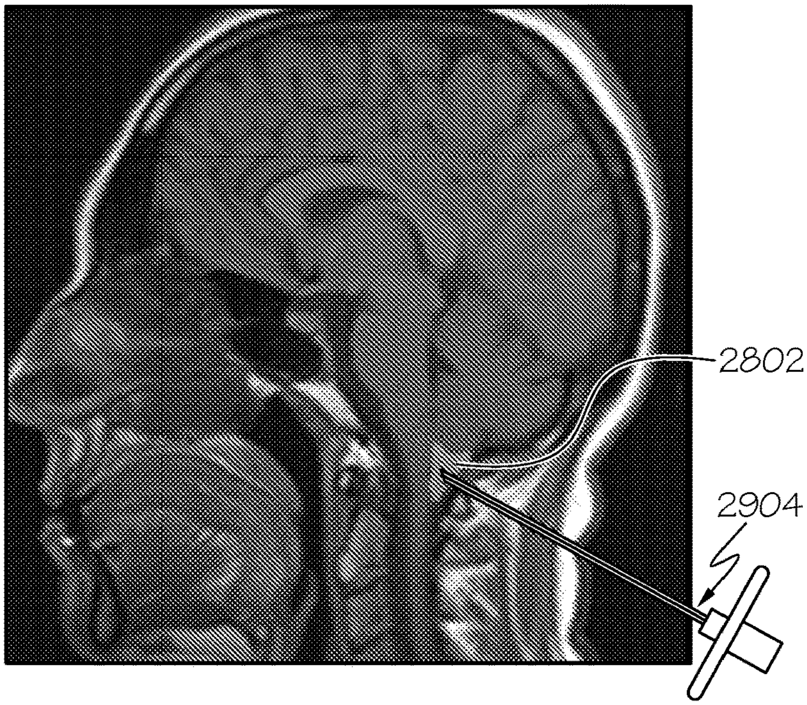
FIG. 31 depicts the sagittal view of FIG. 30 with the optical encoder stylet of FIG. 30 removed, according to one or more aspects shown and described herein.

FIG. 31 depicts the sagittal view of FIG. 30 with the navigated stylet 3005 of FIG. 30 removed, according to various aspects of the present disclosure. Referring to FIG. 30, the needle 2904 may remain inserted within the cisterna magna 2802 until the catheter tubing has been successfully placed.

Figure 32:
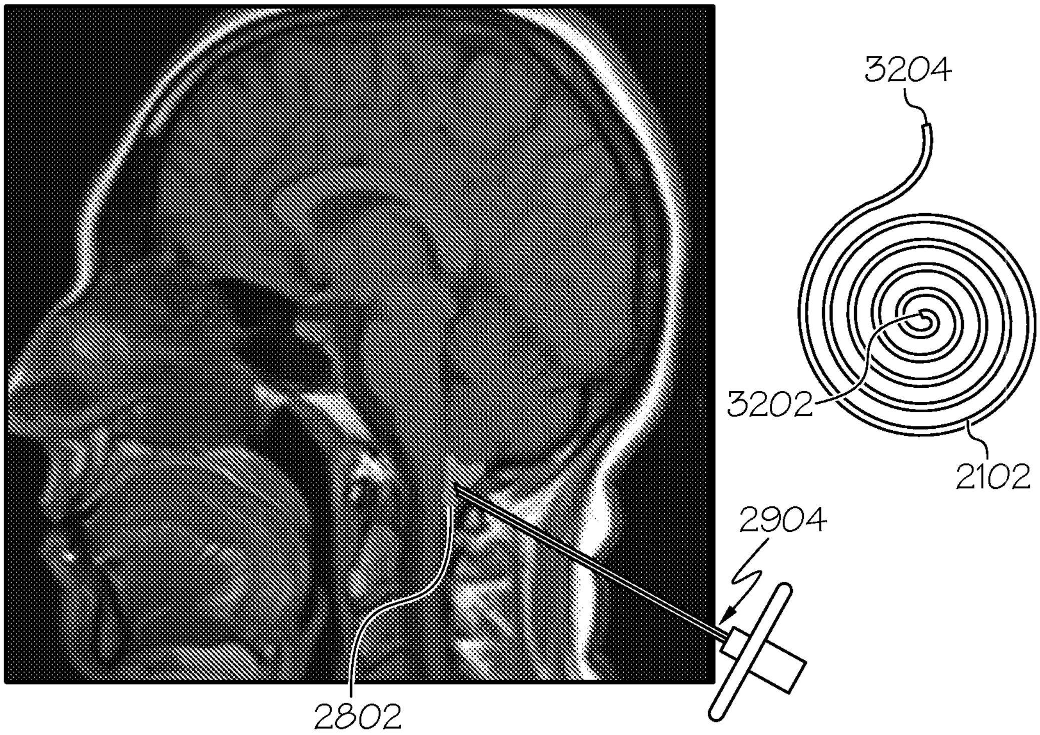
FIG. 32 depicts the sagittal view of FIG. 30 where a CSF source tube is positioned to be threaded through the needle into the cisterna magna, according to one or more aspects shown and described herein.

FIG. 32 depicts the sagittal view of FIG. 30 where a CSF source tube 2102 (e.g., catheter, silicone tube, and/or the like) is positioned to be threaded through the needle 2904 into the cisterna magna 2802, according to various aspects of the present disclosure. More specifically, a first end 3202 of the CSF source tube 2102 may be threaded through the needle 2904 into the cisterna magna 2802. According to various aspects, after the first end 3202 of the CSF source tube 2102 is positioned within the cisterna magna 2802, the needle 2904 may be slidingly removed (e.g., over the CSF source tube 2102 and off of the second end 3204 of the CSF source tube 2102) from the subject while the first end 3202 of the CSF source tube 2102 remains in the cisterna magna 2802.

Figure 33:
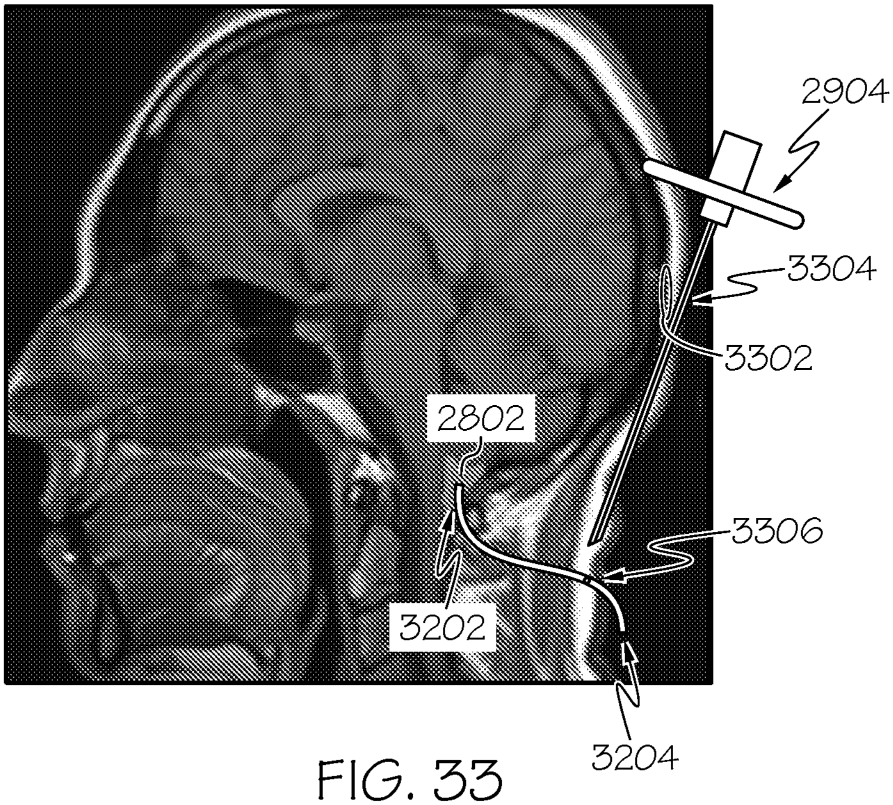
FIG. 33 depicts the sagittal view of FIG. 30 where the needle may be used to tunnel, subcutaneously, from an incision at and/or near a cranial hole (e.g., a DVS burr hole) to an exit point of the CSF source tube, according to one or more aspects shown and described herein.

FIG. 33 depicts the sagittal view of FIG. 30 where the needle 2904 may be used to tunnel, subcutaneously, from an incision 3304 (e.g., inferior portion) at and/or near a cranial hole 3302 (e.g., DVS burr hole 102) to an exit point 3306 of the CSF source tube 2102, according to various aspects of the present disclosure. Referring to FIG. 33, the first end 3202 of the CSF source tube 2102 may remain positioned within the cisterna magna 2802 while the second end 3204 of the CSF source tube 2102 may be threaded/passed retrograde through the needle 2904 (e.g., subcutaneously) toward the cranial hole 3302.

Figure 34:
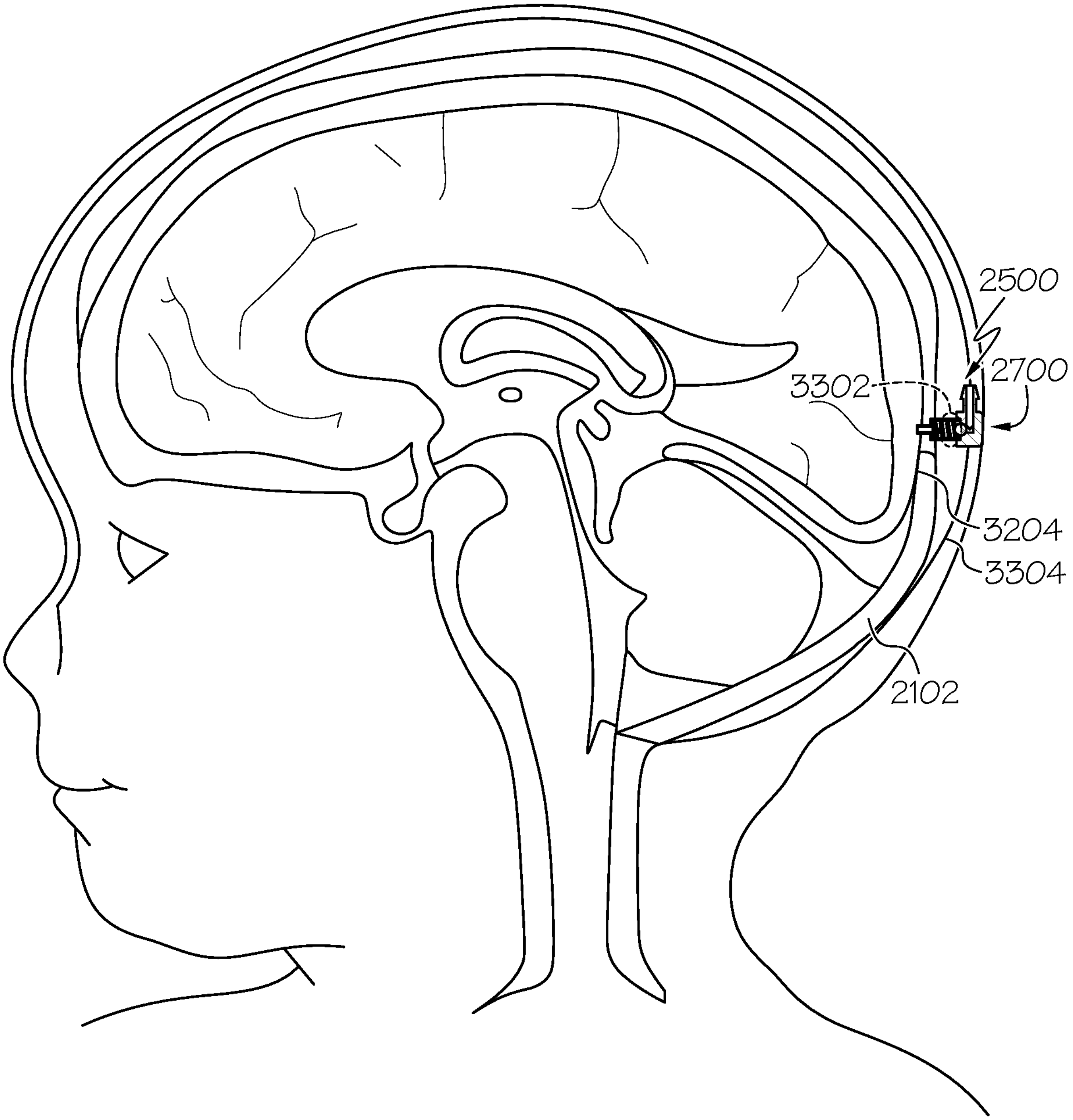
FIG. 34 depicts another sagittal view after the needle of FIG. 33 has been slidingly removed from the incision at and/or near the cranial hole, according to one or more aspects shown and described herein.

FIG. 34 depicts another sagittal view after the needle 2904 of FIG. 33 has been slidingly removed (e.g., over the CSF source tube 2102 and off of the second end 3204) from the incision 3304 at and/or near the cranial hole 3302, according to various aspects of the present disclosure. According to aspects of the present disclosure, excess CSF source tube 2102, initially extending out of the incision 3304, may be cut to length (e.g., as shown in FIG. 34) to fit onto the PFC-DVS drain assembly 2500 (FIG. 25, e.g., the PFC inlet tip 1978 of FIG. 21) to form the single burr hole hydrofix implant 2700 (FIG. 27).

Figure 35:
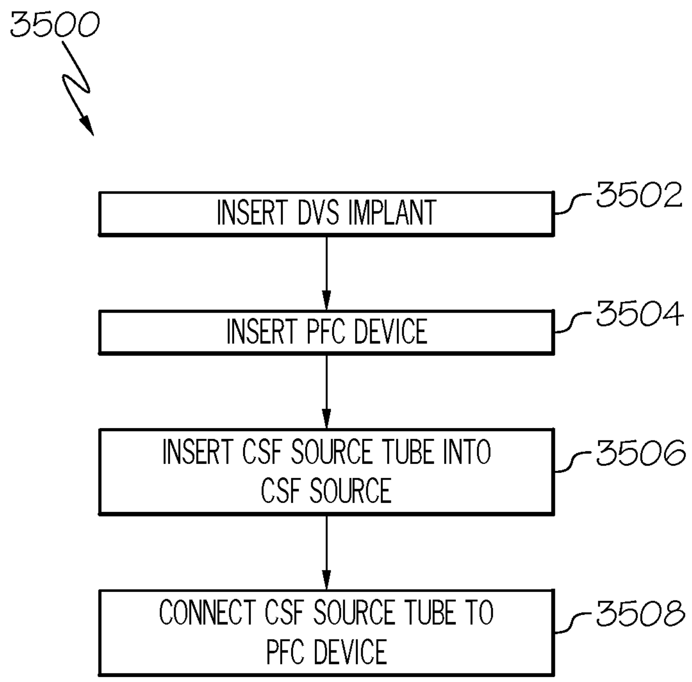
FIG. 35 depicts a flow diagram of an illustrative method for coupling the single burr hole Hydrofix implant of FIG. 27 to a subject's skull 106, according to one or more aspects shown and described herein.

FIG. 35 depicts a flow diagram of an illustrative method 3500 for coupling the single burr hole hydrofix implant 2700 of FIG. 27 to a subject's skull 106, according to various aspects of the present disclosure. Referring to FIG. 35, block 3502 may include inserting the DVS implant 1224 (e.g., into the DVS implant anchor 202). Here, it should be understood that the method 300 of FIG. 3, as described herein, may have already been performed. According to various aspects, the DVS implant 1224 may be advanced into the subject's dura, as described herein, via a DVS implant driver 1222. At block 3504, the PFC device 1970 may be inserted (e.g., after removal of the DVS implant driver 1222) within the DVS implant 1224 as described herein. At block 3506, the CSF source tube 2102 may be placed in a CSF source (e.g., cisterna magna, lateral ventricle, or SAS) as described herein. At block 3508, the CSF source tube 2102 may be coupled to the PFC device 1970.

FIG. 36A through 46B depicts another surgical method for the placement of a DVS implant device, as described herein using a DVS implant device alignment assembly. Utilizing CT and/or MRI navigation assisted techniques or with endovascular fluoroscopic techniques, or a combination of both, and then marking the desired drill/burr location, first on the scalp, then on the upper table of the skull, the ideal target location of a DVS implant may be identified in the manner described herein.

Figure 36B:
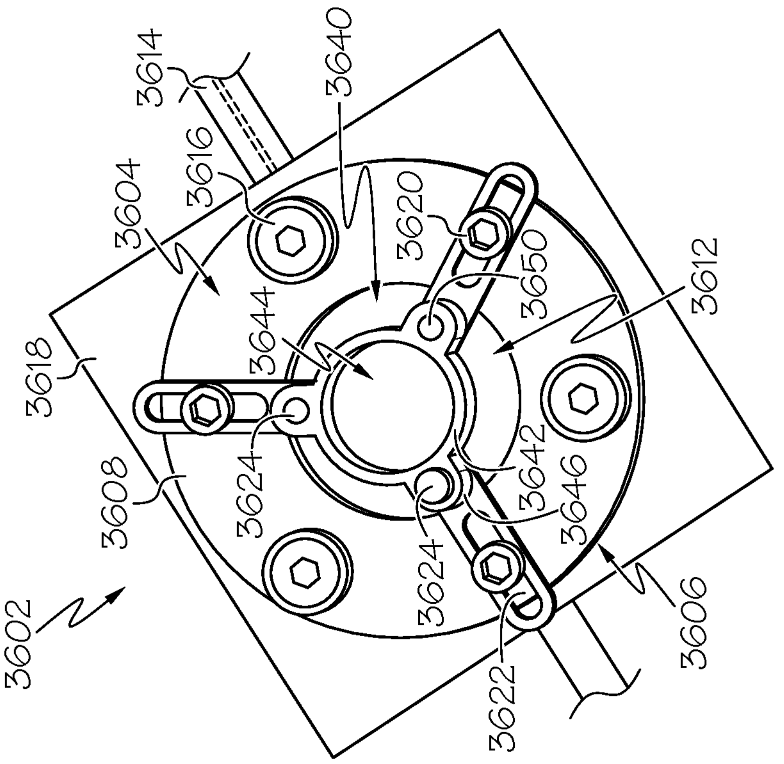
FIG. 36B depicts a perspective view of the guide assembly of FIG. 36A and a burr guide, according to one or more aspects shown and described herein.
Figure 36A:
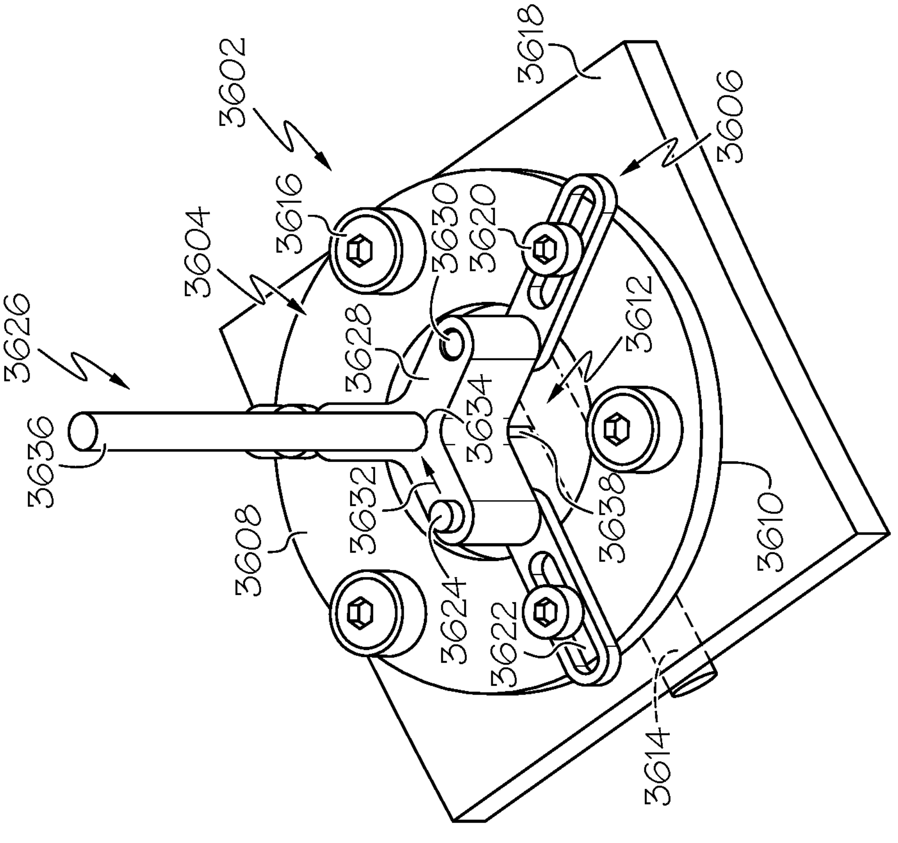
FIG. 36A depicts a perspective view of an illustrative guide assembly including a procedure guide instrument and a plurality of locking adjustment arms positioned on a subject's skull, a probe guide and a navigated probe tip positioned on the guide assembly, according to one or more aspects shown and described herein.

FIG. 36A depicts an illustrative guide assembly 3602 including a procedure guide instrument 3604 and a plurality of locking adjustment arms 3606. The procedure guide instrument 3604 has an upper surface 3608 and an opposite lower surface 3610. An aperture 3612 is formed in the procedure guide instrument 3604 extending through the upper surface 3608 and the lower surface 3610. As described in more detail herein, the guide assembly 3602 is initially positioned such that the aperture 3612 formed in the procedure guide instrument 3604 is positioned over the DVS 3614, which extends in a longitudinal direction. The procedure guide instrument 3604 includes one or more adjustment screws 3616 for securing the procedure guide instrument 3604 on the subject's skull 3618. It should be appreciated that any suitable locking members other than adjustment screws 3616 may be provided for securing the procedure guide instrument 3604 onto the subject's skull 3618. As shown, a plurality of adjustment screws 3616 are positioned around the aperture 3612. The procedure guide instrument 3604 includes one or more fasteners 3620 extending from the upper surface 3608 thereof for securing each of the locking adjustment arms 3606 to the upper surface 3608 of the procedure guide instrument 3604, as described herein.

The locking adjustment arms 3606 allow for a variety of alignment devices to be secured to the procedure guide instrument 3604 and positioned about the aperture 3612. Although the guide assembly 3602 is illustrated as including three locking adjustment arms 3606, it should be appreciated that fewer arms may be provided such as, for example, one or two. Alternatively, additional locking adjustment arms 3606 may be provided to provide additional control over movement of the alignment devices. Each locking adjustment arm 3606 has a slot 3622 formed therein extending in a radial direction from the aperture 3612 and a positioning element such as, for example, a pin 3624 extending in a direction perpendicular to the slot 3622. It should be appreciated that the pin 3634 is one example of a positioning element and other positioning elements now known or yet to be developed could be substituted, but that a pin is preferred for certain embodiments. When a plurality of locking adjustment arms 3606 are provided, one or more of the pins 3624 may have a different diameter than the other pins 3624 to correctly orient the various alignment devices positioned on the procedure guide instrument 3604. Additionally, one of the pins 3624 may be color-coded to advantageously identify a correct orientation thereof. Each fastener 3620 extends through a corresponding slot 3622 formed in the locking adjustment arm 3606 such that each locking adjustment arm 3606 is slidably positionable along the upper surface 3608 of the procedure guide instrument 3604. The fasteners 3620 may be tightened to secure the locking adjustment arms 3606 in position relative to the procedure guide instrument 3604.

As shown in FIG. 36A, a probe guide 3626 is positioned on the procedure guide instrument 3604. The probe guide 3626 includes one or more legs 3628 extending in a radial direction relative to the aperture 3612 of the procedure instrument guide when positioned thereon. Each leg 3628 has a hole 3630 formed therein for receiving a corresponding one of the pins 3624. In embodiments, an arrow 3632 may be provided on the probe guide 3626 for advantageously indicating the direction of the longitudinal axis of the DVS 3614. The probe guide 3626 also has a channel 3634 extending in an axial direction relative to the aperture 3612 for receiving a navigated probe tip 3636. It is intended that the probe guide 3626, and thus, the navigated probe tip 3636 are positioned above the DVS 3614. Once the navigated probe tip 3636 is inserted into the probe guide 3626, the probe guide 3626 is permitted to move relative to the aperture 3612 of the procedure guide instrument 3604 by allowing the locking adjustment arms 3606 to be slidably positioned relative to the procedure guide instrument 3604. Once the end 3638 of the navigated probe tip 3636 is aligned with the target location by adjusting the position of the probe guide 3626, which may be determined based on, for example, a previously marked location on the subject's skull or the fluoroscopic/catheter wire method discussed herein, the locking adjustment arms 3606 are locked in place to secure the probe guide 3626 in position on the procedure guide instrument 3604. Thereafter, the navigated probe tip 3636 is inserted further into the channel 3634 of the probe guide 3626 such that the end 3638 of the navigated probe tip 3636 contacts the subject's skull 3618 and leaves a mark indicating a target location for drilling. In this manner, all subsequent steps leading up to and including the insertion of the DVS implant may advantageously maintain reference to the original target location with the locking adjustment arms 3606 locked in position on the procedure guide instrument 3604.

Once the target location for drilling has been marked by the navigated probe tip 3636, the probe guide 3626 and navigated probe tip 3636 are unsecured from the guide assembly 3602 and removed. Thereafter, as shown in FIG. 36B, a burr guide 3640 is positioned on the guide assembly 3602. The burr guide 3640 includes a body 3642 defining a circular channel 3644 for receiving a drill device, not shown. Similar to the probe guide 3626, the burr guide 3640 includes one or more legs 3646 extending in a radial direction from the body 3642 relative to the circular channel 3644. Each leg 3646 has a hole 3650 formed therein for receiving a corresponding one of the pins 3624. Once the burr guide 3640 is positioned on the guide assembly 3602, a burr hole 3652 may be drilled by the drill device at the target location. The burr hole 3652 is formed in a direction that is orthogonal to the subject's skull 3618, i.e., perpendicular to the dura 3654, and to the DVS 3614.

Figure 37:
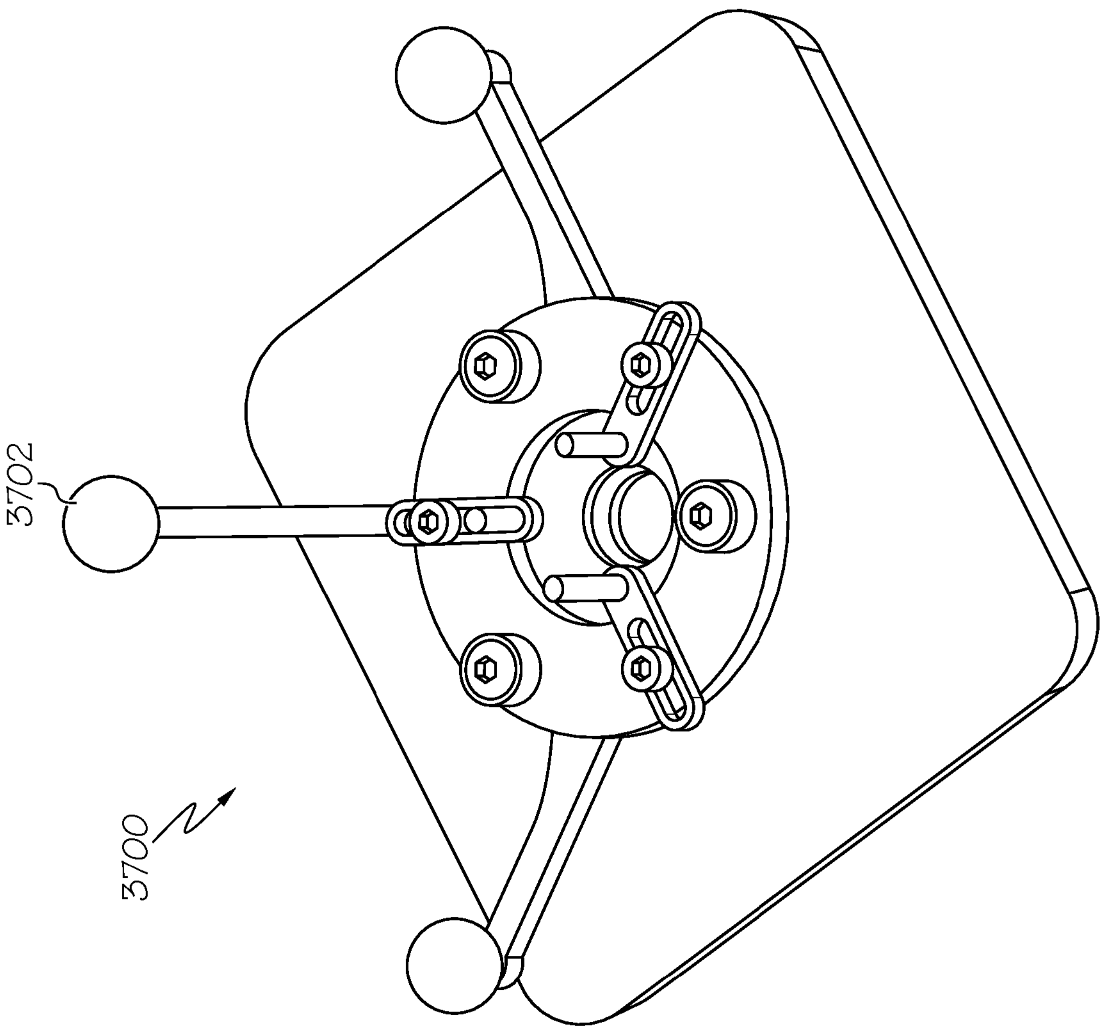
FIG. 37 depicts a perspective view of an illustrative guide assembly including tracking elements positioned on a subject's skull, according to one or more aspects shown and described herein.

FIG. 37 depicts a variant of the procedure guide instrument 3700 that includes additional navigation components 3702, for example, infra-red reflectors and the like. The navigation components 3702 allow the procedure guide instrument 3700 to couple its position on the skull 3618 to a commercially available CT or MRI navigation guidance method, such as Stealth sold by Medtronics or the like.

Figure 38A:
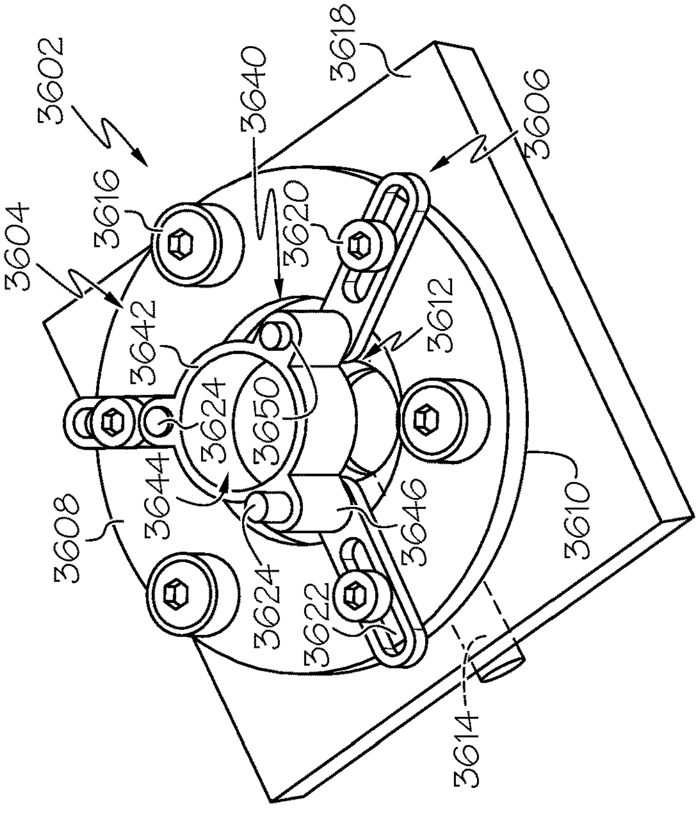
FIG. 38A depicts the guide assembly of FIG. 36A and the burr guide of FIG. 36B after a burr hole is formed in the subject's skull, according to one or more aspects shown and described herein.
Figure 38B:
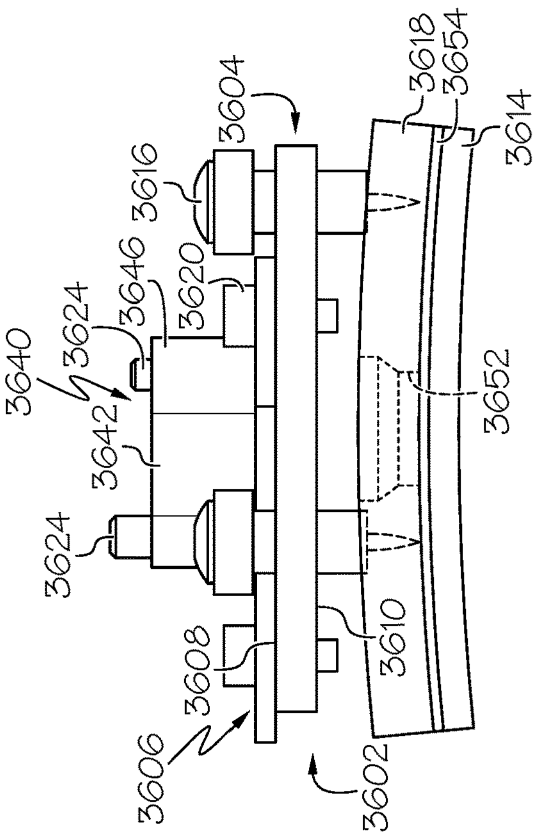
FIG. 38B depicts a cross-sectional view of the guide assembly of FIG. 36A and the burr guide of FIG. 36B after a burr hole is formed in the subject's skull, according to one or more aspects shown and described herein.
Figure 39:
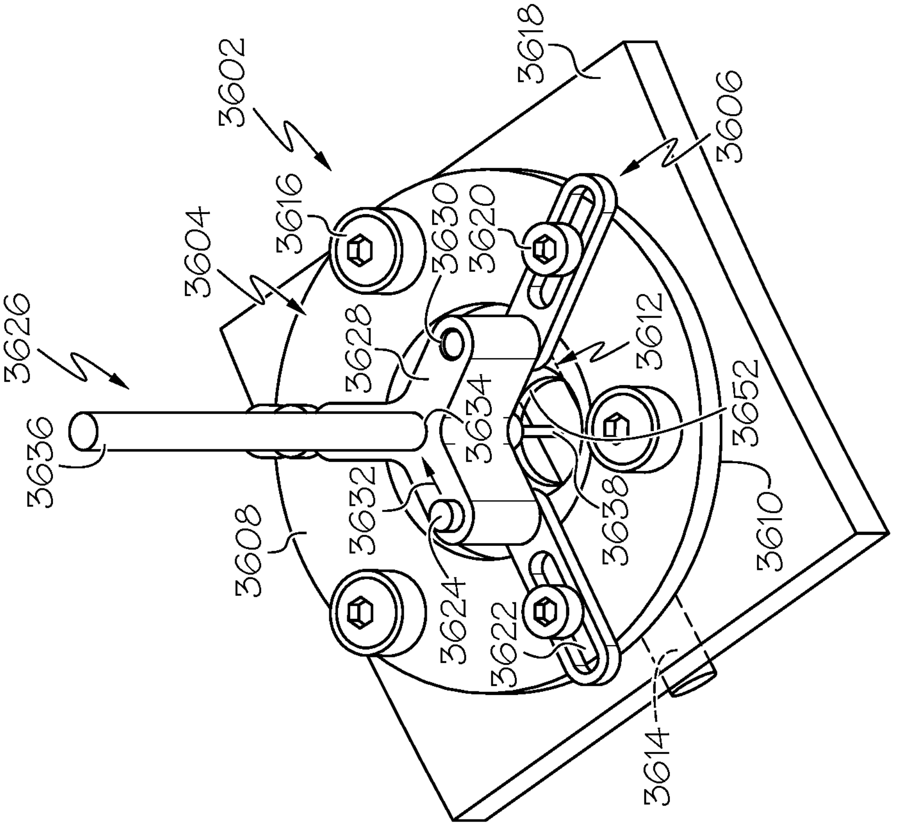
FIG. 39 depicts a perspective view of the guide assembly and the probe guide of FIG. 36A after the burr hole is formed, according to one or more aspects shown and described herein.

FIGS. 38A and 38B depict the burr guide 3640 provided on the guide assembly 3602 after the burr hole 3652 has been formed in the subject's skull 3618. Once the burr hole 3652 has been formed, the burr guide 3640 is unsecured and removed from the guide assembly 3602. As shown in FIG. 39, the probe guide 3626 and the navigated probe tip 3636 may be repositioned on the guide assembly 3602. This allows for confirmation that the burr hole 3652 was accurately formed over the DVS 3614. Additionally, the navigated probe tip 3636 may be utilized to provide another marking for purposes of confirming insertion points throughout the remaining steps of the procedure.

Figure 40B:
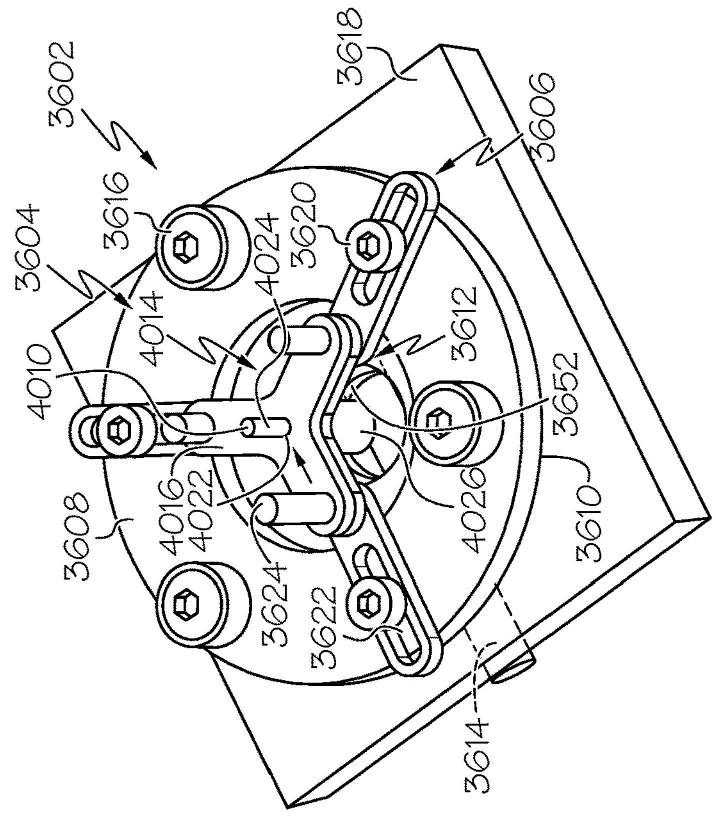
FIG. 40B depicts a perspective view of the guide assembly of FIG. 36A, the needle guide of FIG. 40A, and a safety stop positioned on the needle guide, according to one or more aspects shown and described herein.
Figure 40A:
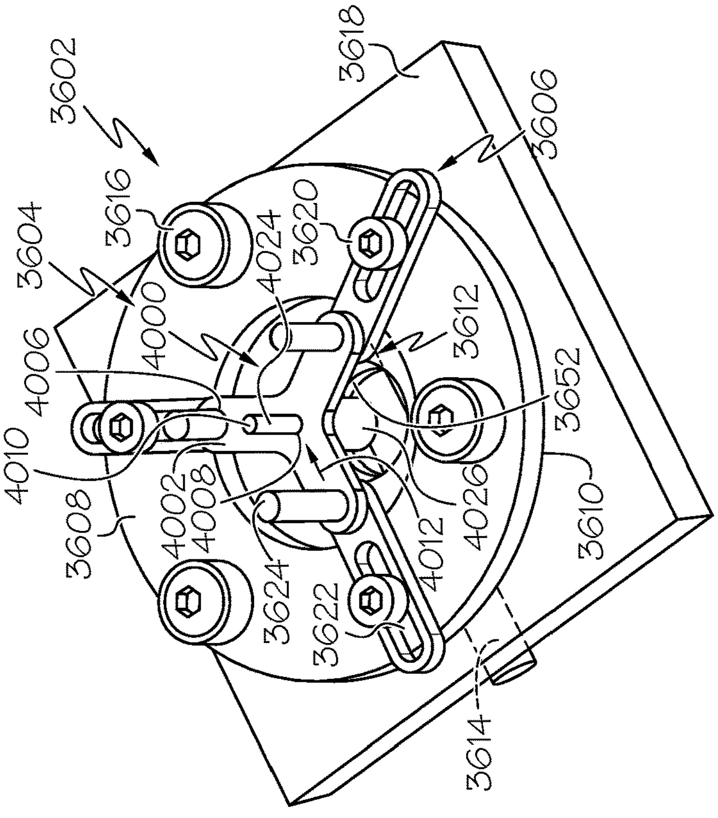
FIG. 40A depicts a perspective view of the guide assembly of FIG. 36A and a needle guide positioned on the guide assembly, according to one or more aspects shown and described herein.

Once the location of the burr hole 3652 is confirmed to be positioned over the DVS 3614, the probe guide 3626 and the navigated probe tip 3636 are removed and, as shown in FIG. 40A, a needle guide 4000 is positioned on the guide assembly 3602. Similar to the probe guide 3626, the needle guide 4000 includes one or more legs 4002 extending in a radial direction relative to the aperture 3612 when positioned on the procedure guide instrument 3604. Each leg 4002 has a hole 4006 formed therein for receiving a corresponding one of the pins 3624. The needle guide 4000 also has a channel 4008 extending in an axial direction relative to the aperture 3612 for receiving a needle 4010. In embodiments, an arrow 4012 may be provided on the needle guide 4000 for indicating the direction of the longitudinal axis of the DVS 3614.

FIG. 40B depicts a safety stop 4014 positioned on a surface of the needle guide 4000 opposite the procedure guide instrument 3604. The safety stop 4014 has substantially the same structure as the needle stop 4024. Specifically, the safety stop 4014 includes one or more legs 4016 extending in a radial direction relative to the aperture 3612 when positioned on the needle guide 4000. Each leg 4016 has a hole 4020 formed therein for receiving a corresponding one of the pins 3624. The safety stop 4014 also has a channel 4022 extending in an axial direction relative to the aperture 3612 for receiving the needle 4010. As discussed in more detail herein, the safety stop 4014 has a thickness slightly greater than a thickness of the dura 3654, for example, 1.5 mm. In embodiments, the needle 4010 is a 28 gauge needle.

Figure 40D:
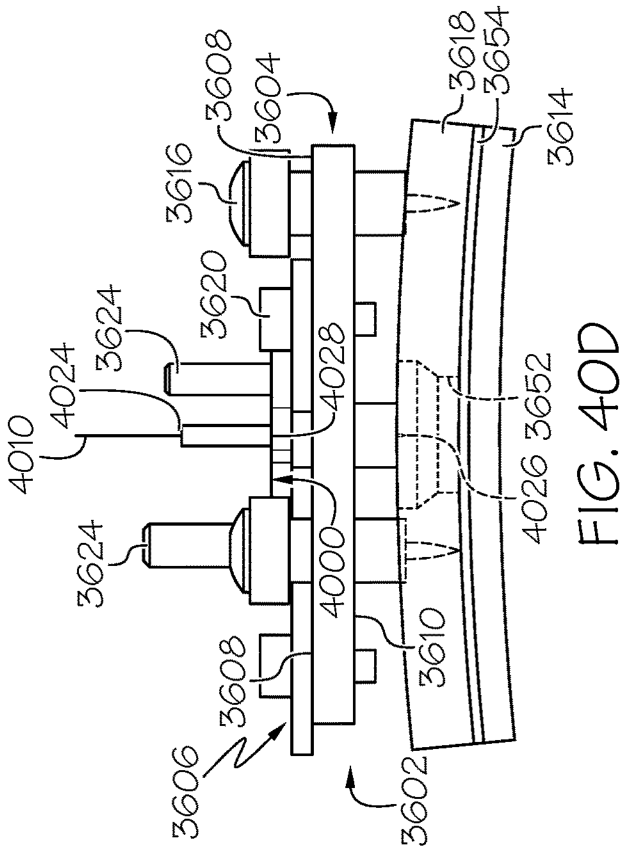
FIG. 40D depicts a cross-sectional view of a needle extending through the needle guide of FIG. 40B and extending through the dura into the DVS, according to one or more aspects shown and described herein.
Figure 40C:
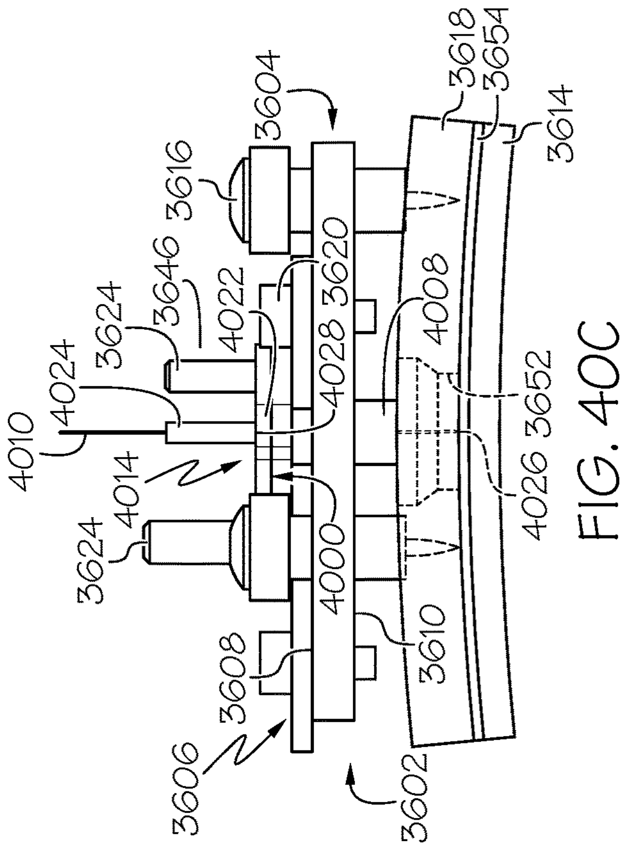
FIG. 40C depicts a cross-sectional view of a needle extending through the needle guide of FIG. 40B and contacting a top surface of the dura, according to one or more aspects shown and described herein.

FIG. 40C depicts a cross-sectional side view of the needle guide 4000 and the safety stop 4014 positioned on the guide assembly 3602. Additionally, the needle 4010 is shown including a needle stop 4024 abutting against a surface of the safety stop 4014 opposite the needle guide 4000. The needle stop 4024 is movably adjustable along the length of the needle 4010. However, the needle stop 4024 may be selectively fixed on the needle 4010 to define a fixed length between the end 4026 of the needle 4010 and the end 4028 of the needle stop 4024 abutting against the safety stop 4014. Accordingly, as shown in FIG. 40C, the needle 4010 is lowered through the channel 4022 of the safety stop 4014, the channel 4008 of the needle guide 4000, and the burr hole 3652 such that the end 4026 of the needle 4010 contacts an upper surface of the dura 3654 without puncturing the dura 3654. Once the end 4026 of the needle 4010 contacts the dura 3654, the needle stop 4024 is secured to the needle 4010 to prevent the needle 4010 from extending into the dura 3654.

Thereafter, as shown in FIG. 40D, the needle 4010 and the needle stop 4024 are removed from the needle guide 4000 to permit the safety stop 4014 to be removed. Once the safety stop 4014 is removed, the needle 4010, including the needle stop 4024 now fixed thereto, is reinserted into the channel 4008 of the needle guide 4000 and into the burr hole 3652. Due to the thickness of the safety stop 4014 being slightly greater than the thickness of the dura 3654, the length defined by the end 4026 of the needle 4010 and the needle stop 4024 is long enough to extend through the dura 3654 and partially into the DVS 3614 with the safety stop 4014 removed.

Figure 40F:
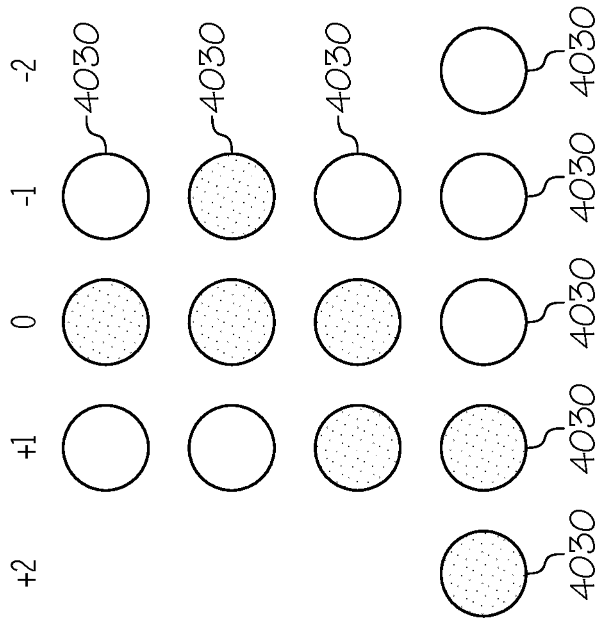
FIG. 40F depicts a plurality of hypothetical scenarios indicating the presence of blood at particular locations after removing the needle of FIG. 40D, according to one or more aspects shown and described herein.
Figure 40E:
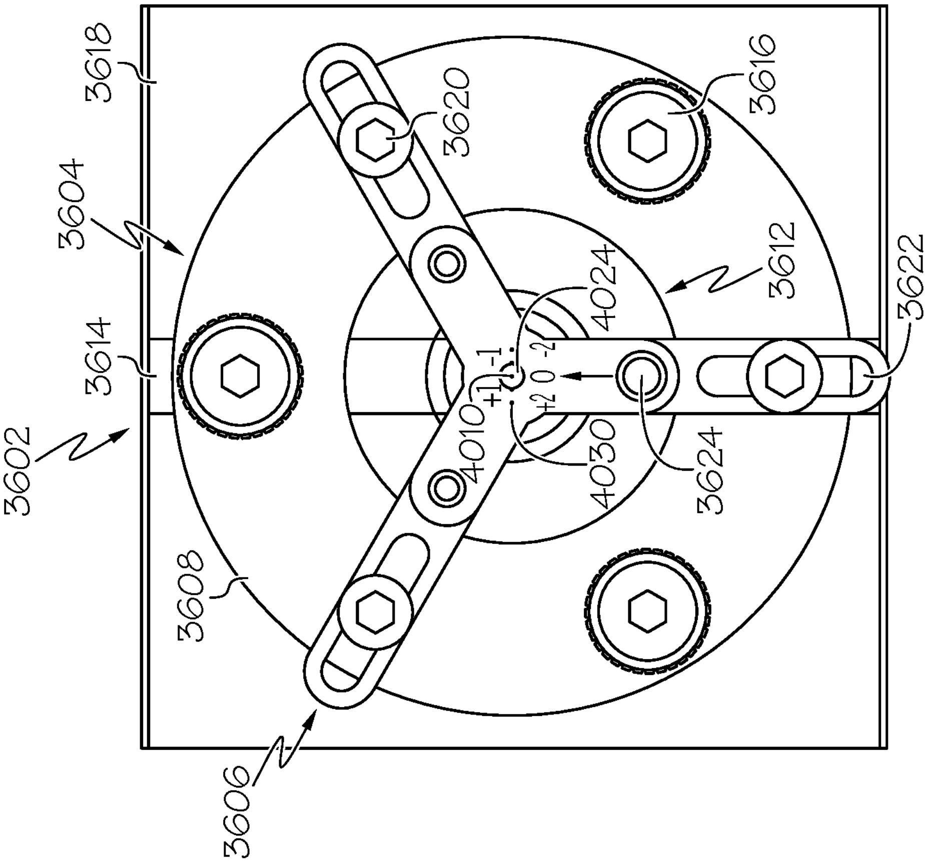
FIG. 40E depicts a plan view of the needle of FIG. 40D extending through the needle guide of FIG. 40B, according to one or more aspects shown and described herein.

FIG. 40E depicts a plan view of the needle guide 4000 with the needle 4010 extended into the dura 3654 (FIG. 40D) and the DVS 3614. In embodiments, the needle guide 4000 has a plurality of channels 4030 through which the needle 4010 may be inserted. The channels 4030 are arranged in a spaced apart linear array and extend perpendicular to the longitudinal axis of the DVS 3614. Each channel 4030 may be denoted with a reference number, for example, "+2", "+1", "0", "−1", "−2". These channels 4030 represent the +/−tolerance as published by the navigated probe manufacturer. Accordingly, each channel 4030 corresponds to an associated implant guide based on a particular offset to be used, as described in more detail herein. Depending on the presence of blood at each location, a midline of the DVS 3614 and a final implant position may advantageously be determined. To identify the precise midline of the DVS 3614 along the longitudinal direction, the needle 4010 is initially inserted into one of the channels 4030, such as the "0" channel. Thereafter, the needle 4010 is inserted into either the "+1" channel or the "−1" channel.

FIG. 40F depicts various scenarios in which blood may be present after the needle 4010 is removed from each of the channels 4030. For example, if blood (indicated by a shaded circle in FIG. 40F) is present in only the "0" channel, an implant guide corresponding to the "0" position will be used, if blood is present in only the "0" position and the "−1" position, an implant guide corresponding to the "−1" position will be used, if blood is present in only the "0" position and the "+1" position, an implant guide corresponding to the "+1" position will be used, if blood is present in only the "+1" position and the "+2" position, an implant guide corresponding to the "+2" position will be used, and if blood is present in only the "−1" position and the "−2" position, an implant guide corresponding to the "−2" position will be used.

Figure 40I:
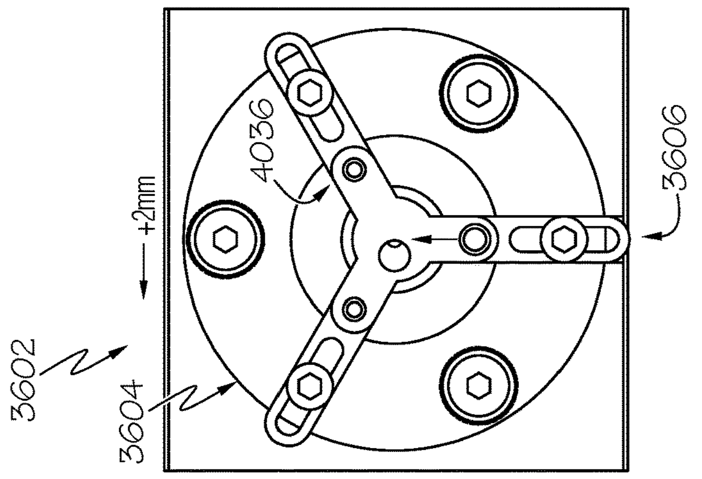
FIG. 40I depicts a plan view of an illustrative implant guide positioned on the guide assembly of FIG. 36A, according to one or more aspects shown and described herein.
Figure 40H:
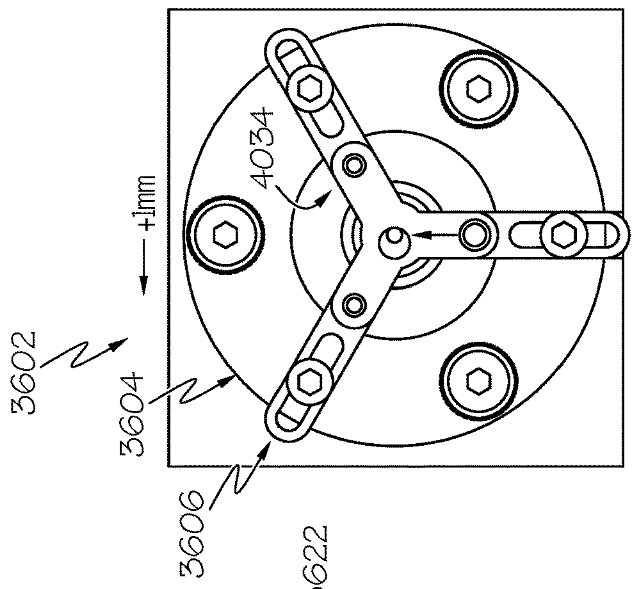
FIG. 40H depicts a plan view of an illustrative implant guide positioned on the guide assembly of FIG. 36A, according to one or more aspects shown and described herein.
Figure 40G:
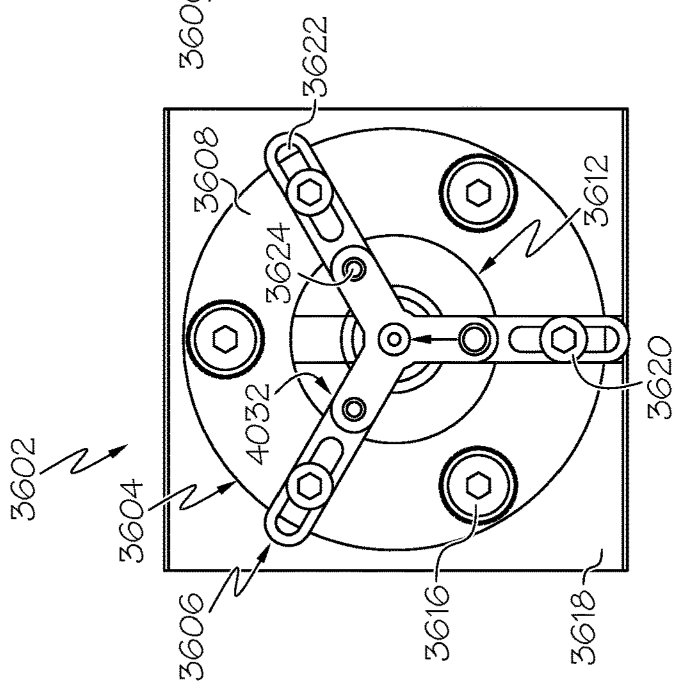
FIG. 40G depicts a plan view of an illustrative implant guide positioned on the guide assembly of FIG. 36A, according to one or more aspects shown and described herein.

FIGS. 40G-40I depict various implant guides to be used based on presence of blood in each of the channels 4030. Specifically, FIG. 40G depicts an implant guide 4032 corresponding to the "0" position in which no offset of the longitudinal axis of the DVS 3614 is required, FIG. 40H depicts an implant guide 4034 corresponding to either the "+1" channel or the "−1" channel as the implant guide 4034 can be flipped for either purposes, and FIG. 40I depicts an implant guide 4036 corresponding to either the "+2" channel or the "−2" channel. Again, each of the implant guides 4032, 4034, 4036 may include an arrow indicating the longitudinal direction of the DVS 3614. As depicted herein, the implant guide 4032 providing no offset, i.e., the implant guide 4032 corresponding to the "0" channel, is utilized for purposes of further illustrating and describing the present disclosure.

Figure 41B:
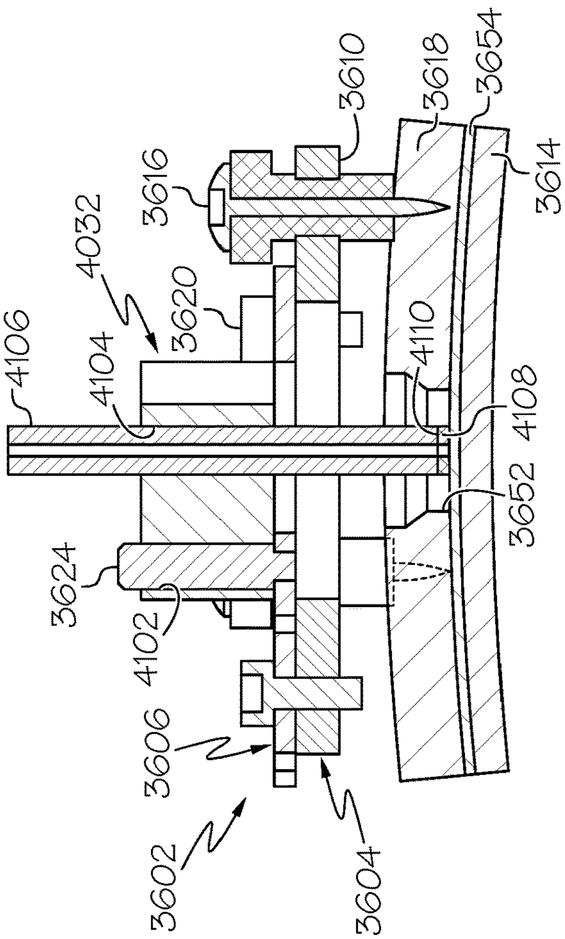
FIG. 41B depicts a cross-sectional view of the guide assembly of FIG. 36A, the implant guide of FIG. 41A, and the applicator stick of FIG. 41A, according to one or more aspects shown and described herein.
Figure 41A:
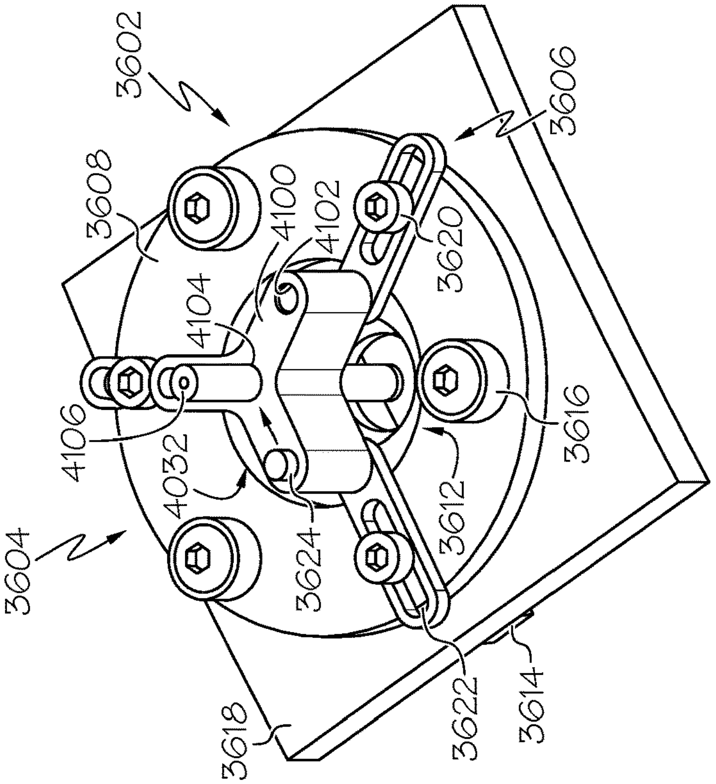
FIG. 41A depicts a perspective view of the guide assembly of FIG. 36A, the implant guide of FIG. 40G positioned on the guide assembly of FIG. 36A, and an applicator stick extending through the implant guide, according to one or more aspects shown and described herein.

As such, FIG. 41A depicts the implant guide 4032 positioned on the guide assembly 3602. Similar to the probe guide 3626, the implant guide 4032 includes one or more legs 4100 extending in a radial direction relative to the aperture 3612 when positioned on the guide assembly 3602. Each leg 4100 has a hole 4102 formed therein for receiving a corresponding one of the pins 3624. The implant guide 4032 also has a channel 4104 extending in an axial direction relative to the aperture 3612 for receiving an applicator stick 4106.

Figure 41C:
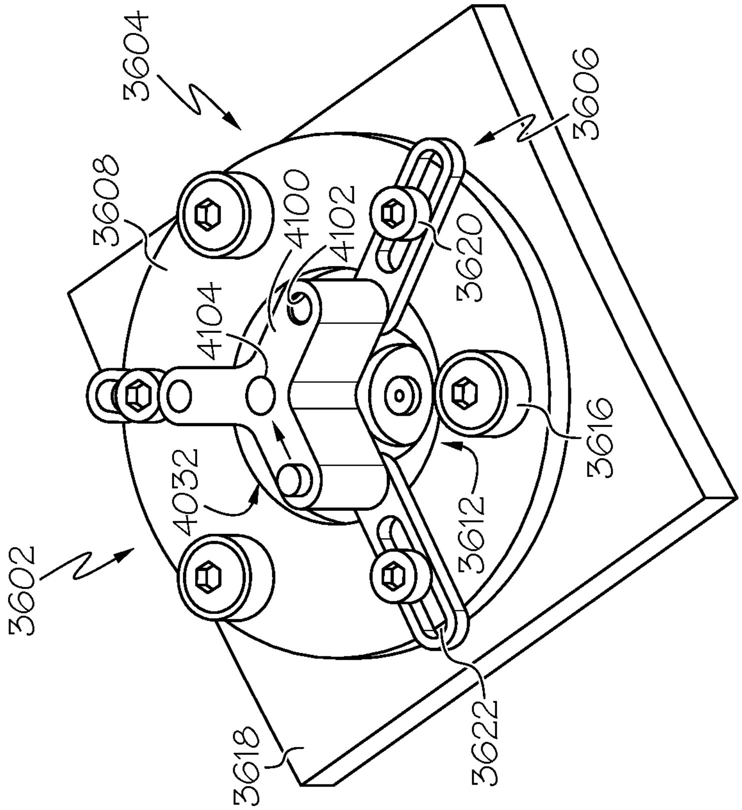
FIG. 41C depicts a perspective view of the guide assembly of FIG. 36A and the implant guide of FIG. 41A with the applicator stick removed after depositing a dura stiffening pad, according to one or more aspects shown and described herein.

FIG. 41B depicts the applicator stick 4106 extending through the channel 4104 of the implant guide 4032. A dura stiffening pad 4108 is provided on an end 4110 of the applicator stick 4106. In embodiments, the dura stiffening pad 4108 has a pair of opposite adhesive surfaces. The dura stiffening pad 4108 may be an adhesively backed fibrous pad that will allow for eventual tissue in-growth onto the dura 3654. Thus, the dura stiffening pad 4108 is initially adhered to the end 4110 of the applicator stick 4106 and, when the applicator stick 4106 extends through the channel 4104 of the implant guide 4032 such that the opposite surface of the dura stiffening pad 4108 contacts the dura 3654 and pressure is applied for a sufficient length of time, the dura stiffening pad 4108 adheres to the dura 3654 as the applicator stick 4106 is removed from the implant guide 4032, as shown in FIG. 41C.

Figure 42A:
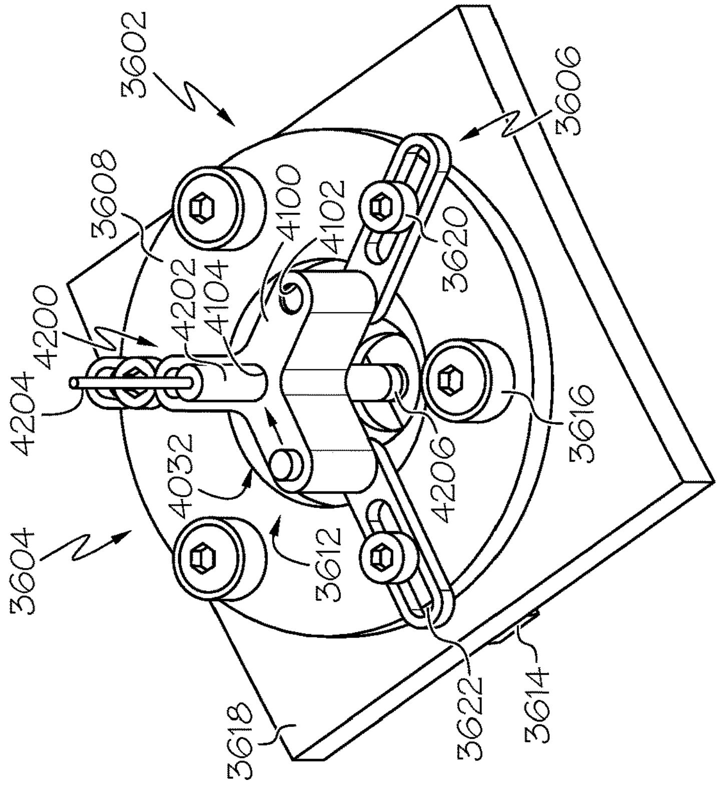
FIG. 42A depicts a perspective view of the guide assembly of FIG. 36A, the implant guide of FIG. 41A, and an implant insertion tool assembly extending through the implant guide, according to one or more aspects shown and described herein.
Figure 42B:
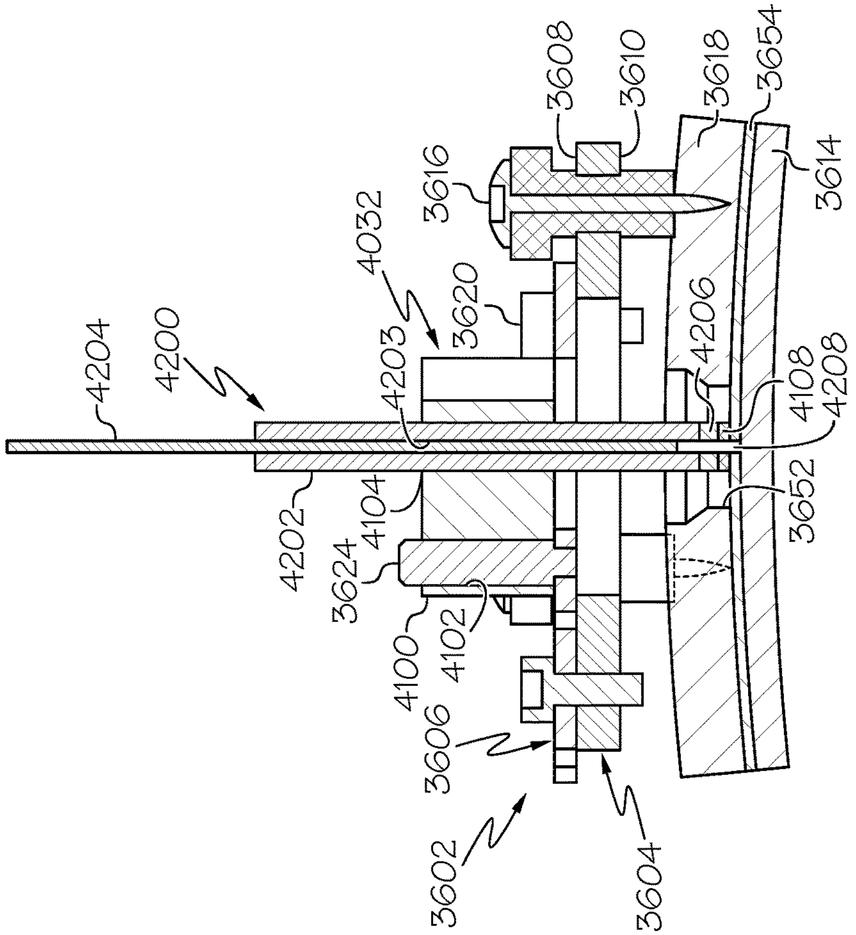
FIG. 42B depicts a cross-sectional view of the guide assembly of FIG. 36A, the implant guide of FIG. 41A, and the implant insertion tool assembly of FIG. 42A, according to one or more aspects shown and described herein.

Thereafter, FIGS. 42A and 42B depicts an implant assembly 4200 extending through the channel 4104 of the implant guide 4032. Specifically, the implant assembly 4200 includes an implant insertion tool 4202 and an implant flex tube 4204 extending through a channel 4203 formed in the implant insertion tool 4202. In embodiments, the implant flex tube 4204 is formed of a silicone rubber. The implant assembly 4200 also includes an implant 4206, such as the CSF implant discussed herein, provided at an end of the implant guide 4032. In embodiments, the implant 4106 may include a valve such as, for example, a check valve, a pressure valve, and the like. A CSF drain element 4208 is provided at an end of the implant 4206 and extends through the dura stiffening pad 4108. In embodiments, the CSF drain element 4208 is 20-25 gauge for penetrating the dura 3654 and extending through the hole formed by the needle 4010. The specific CSF drain element 4208 of the implant 4206 is selected not only for correct length, but also the patient specific selection to also control the desired and maximum volume flow rate of CSF, and as a consequence, the desired and maximum pressure of the discharged CSF. The implant 4206 may be of similar design to implant 1224, however without the need for a threaded body. The implant 4206 is selected from a range of sizes. The size selected is based on the overall length and depth of penetration previously determined, being partially inserted through the DVS 3614, its depth of insertion being limited by its drain component length and the engagement with the dura stiffening pad 4108. The implant 4206 illustrated herein has a rigid distal component 4210 that includes the CSF drain element 4208 and a flexible proximal portion 4212 for attachment to the CSF source. The implant 4206 is adhesively and/or mechanically (e.g. interlocking mating surfaces) secured to the dura stiffening pad 4108 at which point the implant insertion tool 4202 is removed.

Figure 43B:
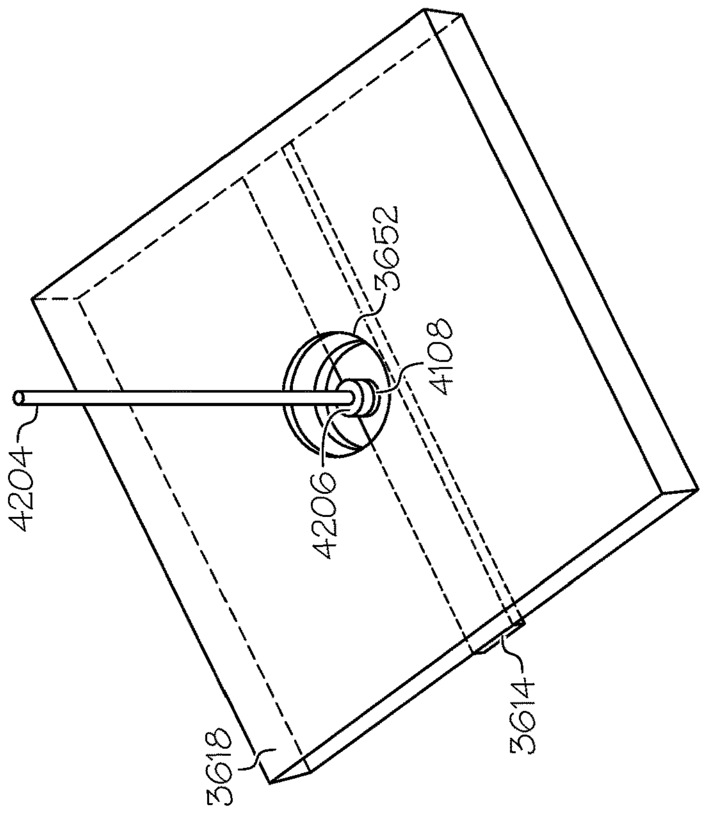
FIG. 43B depicts a perspective view of the implant insertion tool assembly of FIG. 42A with the guide assembly removed, according to one or more aspects shown and described herein.
Figure 43A:
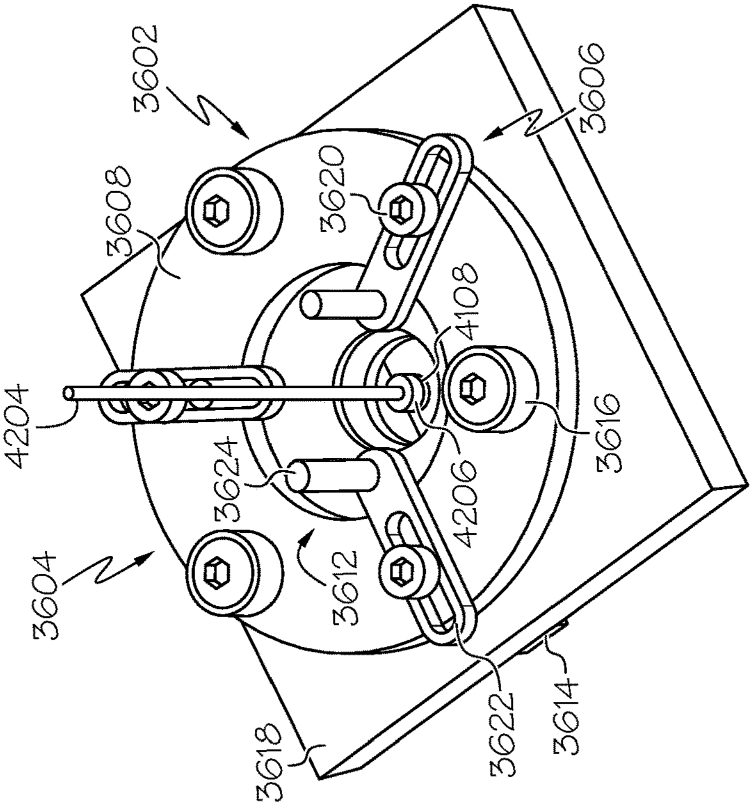
FIG. 43A depicts a perspective view of the guide assembly of FIG. 36A, and the implant insertion tool assembly of FIG. 42A with the implant guide removed, according to one or more aspects shown and described herein.

FIG. 43A depicts the implant guide 4032 removed from the guide assembly 3602 with the implant flex tube 4204 and the implant 4206 remaining in position within the burr hole 3652. FIG. 43B depicts the guide assembly 3602 removed from the subject's skull 3618 by disengaging the adjustment screws 3616.

Figure 44B:
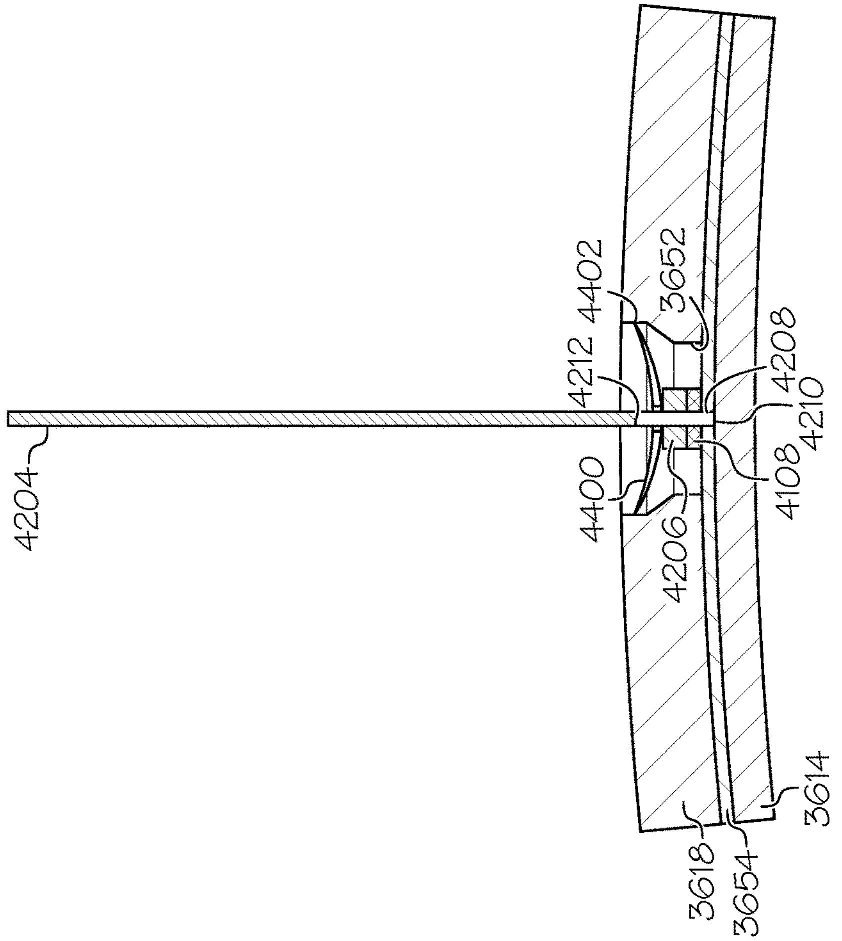
FIG. 44B depicts a cross-sectional view of the implant lock of FIG. 44A positioned on the implant tube of FIG. 44A, according to one or more aspects shown and described herein.
Figure 44A:
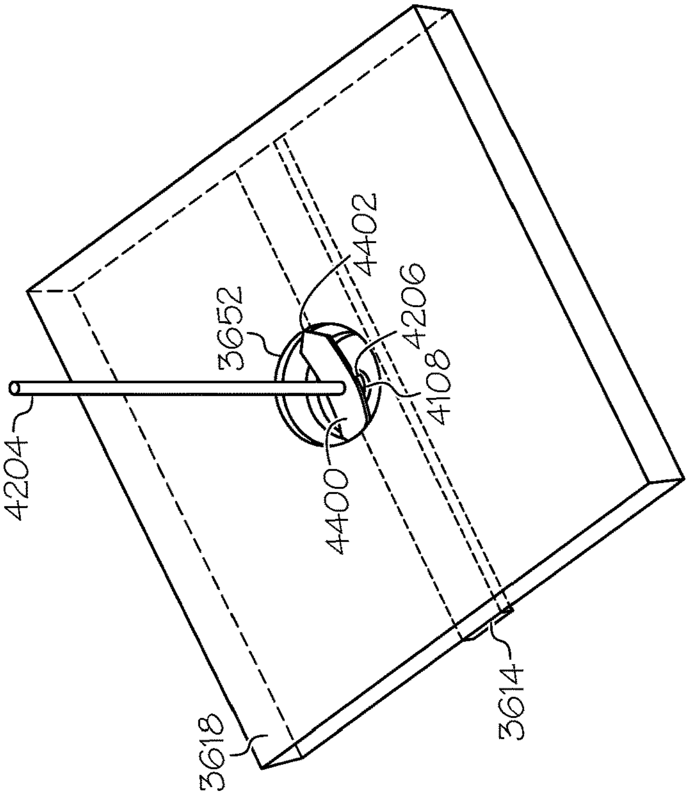
FIG. 44A depicts a perspective view of an implant lock positioned on an implant tube of the implant insertion tool assembly, according to one or more aspects shown and described herein.

FIGS. 44A and 44B depict an implant lock 4400 positioned within the burr hole 3652 for securing the implant flex tube 4204 and the implant 4206 in position relative to the subject's skull 3618. In embodiments, the implant lock 4400 is a flexible member having engaging features 4402 at opposite ends thereof. For example, the engaging features 4402 may be serrated edges or points that engage the subject's skull 3618 via a friction fit when pressed into the burr hole 3652. Thus, movement of the implant flex tube 4204 is less likely to disengage the implant 4206 from the dura 3654 and the DVS 3614. In other embodiments, the implant lock 4400 may be a sealant, such as a non-toxic adhesive, poured into the burr hole 3652 that solidifies for maintaining the position of the implant 4206 within the burr hole 3652 to avoid the use of the implant lock 4400.

Figure 45B:
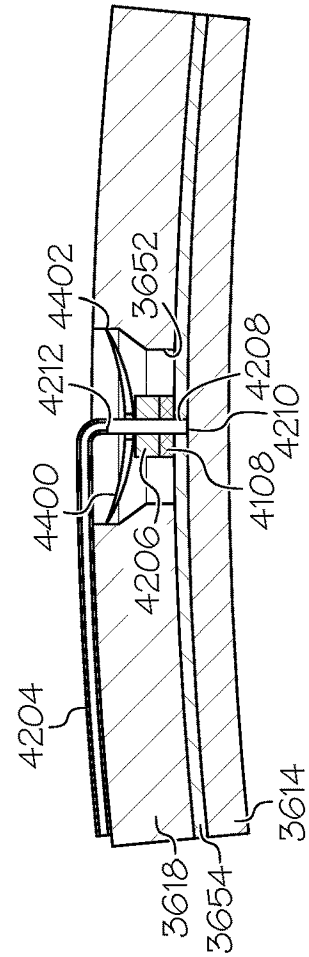
FIG. 45B depicts a cross-sectional view of the implant tube of FIG. 44A bent to extend along the subject's skull, according to one or more aspects shown and described herein.
Figure 45C:
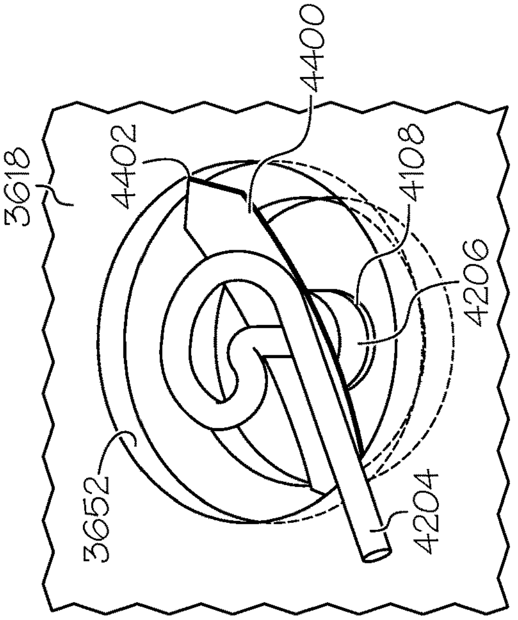
FIG. 45C depicts a perspective view of the implant tube of FIG. 44A curved within the burr hole formed in the subject's skull, according to one or more aspects shown and described herein.
Figure 45A:
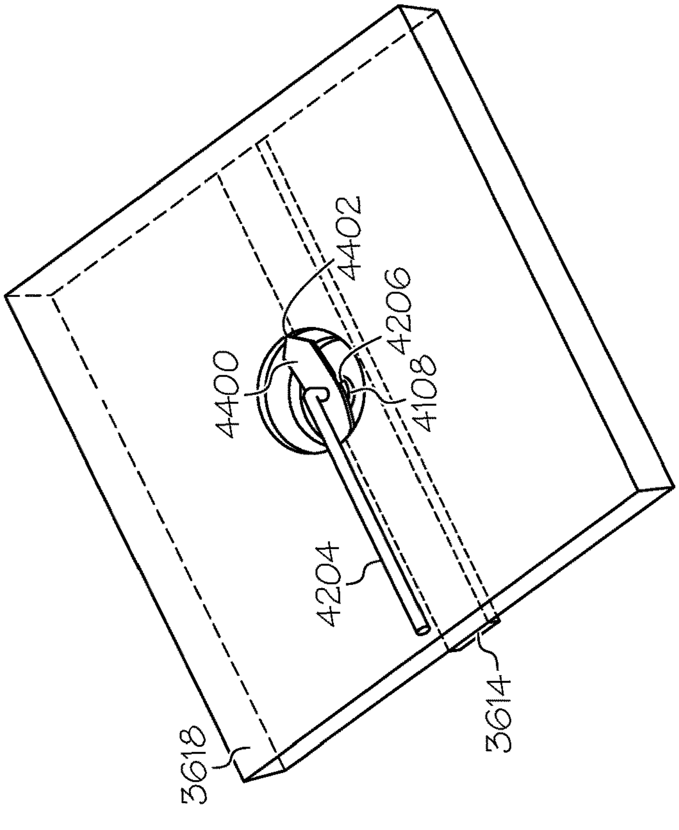
FIG. 45A depicts a perspective view of the implant tube of FIG. 44A bent to extend along the subject's skull, according to one or more aspects shown and described herein.

FIGS. 45A and 45B depict the implant flex tube 4204 being bent to extend along the surface of the subject's skull 3618. FIG. 45C depicts the implant flex tube 4204 being rotated within the burr hole 3652 and, subsequently, extending out of the burr hole 3652. The implant flex tube 4204 being rotated allows the implant flex tube 4204 to extend in any suitable direction.

Figure 46B:
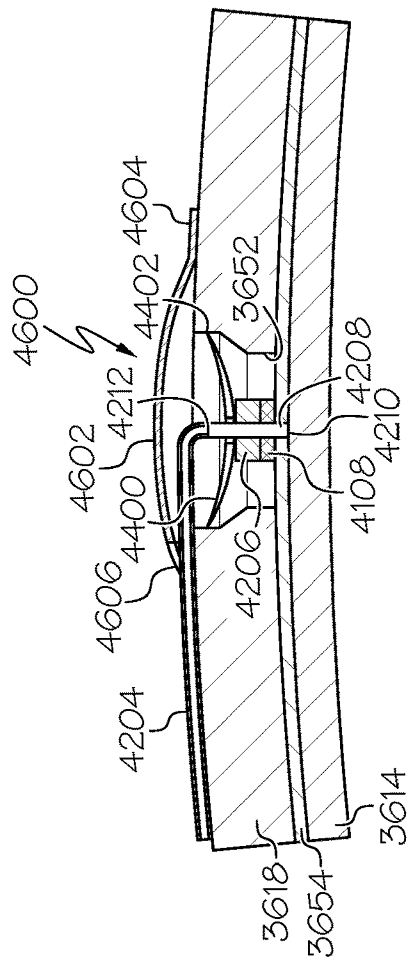
FIG. 46B depicts a cross-sectional view of the protective cap of FIG. 46A positioned over the burr hole and the implant tube of FIG. 44A extending through the protective cap, according to one or more aspects shown and described herein.
Figure 46A:
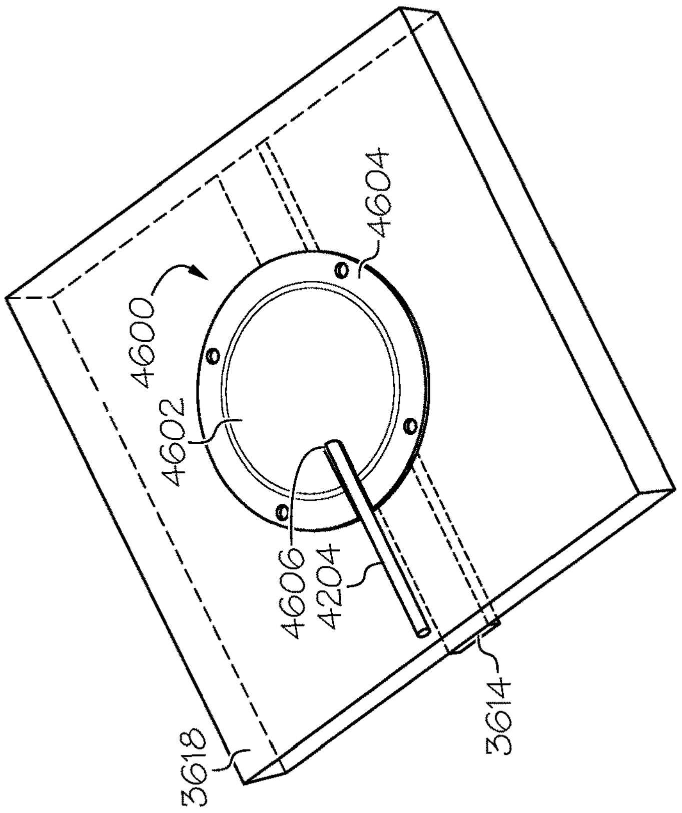
FIG. 46A depicts a perspective view of a protective cap positioned over the burr hole and the implant tube of FIG. 44A extending through the protective cap, according to one or more aspects shown and described herein.

FIG. 46A depicts a protective cap 4600 positioned over the burr hole 3652 to prevent contamination. In embodiments, the protective cap 4600 has a dome shape body 4602 and a flange 4604 that may be secured to the subject's skull 3618 in any suitable manner such as, for example, screws, an adhesive, or the like. Further, the protective cap 4600 has a port 4606 formed therein to permit the implant flex tube 4204 to extend through the protective cap 4600. FIG. 46B depicts a cross-sectional view of the protective cap 4600 illustrating the implant flex tube 4204 extending through the port 4606 formed therein.

Accordingly, it should be appreciated that the present disclosure may advantageously result in the ability to identify a midline of a DVS and align a plurality of devices. e.g., drilling devices, needle devices, and the like, with the identified midline of the DVS without having to reorient each device when positioned on the subject.

Various aspects of the present disclosure may include a kit. More specifically, a kit may include a DVS implant subassembly 1660, including a range of sizes of the following components: DVS implant anchor 202 and a DVS implant 1224, a DVS implant driver 1222, a PFC device 1970, and CSF source tube 2102. In some aspects, the kit may further include a needle 2904 as described herein to insert the CSF source tube 2102 within the subject's CSF source (e.g., cisterna magna, lateral ventricle, or SAS) and/or a tools as described herein, to locate and/or drill a cranial hole (e.g., burr hole) over the subject's DVS.

It should now be understood that the methods, devices, systems, and/or kits described herein encompass various components for accessing CSF in the CSF containing space of a subject, and more particularly, to methods, devices, systems, and/or kits to drain CSF from the subject's CSF containing space into the subject's DVS in such a manner that does not require penetration into the gray matter of the brain.

While particular embodiments have been illustrated and described herein, it should be understood that various other changes and modifications may be made without departing from the spirit and scope of the claimed subject matter. Moreover, although various aspects of the claimed subject matter have been described herein, such aspects need not be utilized in combination. It is therefore intended that the appended claims cover all such changes and modifications that are within the scope of the claimed subject matter.

Various aspects of the present disclosure are represented in the following enumerated clauses:

Clause 1. A dural venous sinus (DVS) implant anchor, the DVS implant anchor comprising: a body comprising: a first portion extending in a first longitudinal direction, a second portion extending in a second longitudinal direction opposite the first longitudinal direction, and a connector portion coupled to the first portion and the second portion at an offset depth that corresponds to a depth of a first part of a thickness of a skull of the subject, wherein, when the DVS implant anchor is disposed within a DVS burr hole in the skull of the subject, the first portion extends along an outside surface of the skull and the second portion is at least partially disposed within the DVS burr hole.

Clause 2. The DVS implant anchor according to Clause 1, further comprising: an adjustment hole and a fixation hole defined in the first portion of the body.

Clause 3. The DVS implant anchor according to any one of Clauses 1-2, further comprising: a DVS implant aperture defined in the second portion of the anchor body.

Clause 4. The DVS implant anchor according to any one of Clauses 1-3, wherein the adjustment hole and the fixation hole are located on the first portion such that the adjustment hole and the fixation hole are disposed over the skull of the subject when the DVS implant aperture is positioned within the DVS burr hole.

Clause 5. The DVS implant anchor according to any one Clauses 1-4, wherein an axis defined by the DVS implant aperture is aligned with an axis of the DVS burr hole to centrally locate the DVS implant aperture within the DVS burr hole.

Clause 6. The DVS implant anchor according to any one of Clauses 1-5, wherein an axis defined by the DVS implant aperture is not aligned with an axis of the DVS burr hole to centrally locate the DVS implant aperture within the DVS burr hole.

Clause 7. The DVS implant anchor according to any one of Clauses 1-6, wherein the DVS implant aperture is defined by an outer diameter and an inner diameter of the second portion, and wherein a threaded portion is defined in the inner diameter of the second portion.

Clause 8. The DVS implant anchor according to any one of Clauses 1-7, wherein the adjustment hole is defined as a slotted hole and the fixation hole is defined as a non-slotted hole.

Clause 9. The DVS implant anchor according to any one of Clauses 1-8, further comprising a first fastener that is fastened through the adjustment hole to adjustably couple the DVS implant anchor to the skull of the subject.

Clause 10. The DVS implant anchor according to any one of Clauses 1-9, further comprising a second fastener that is fastened through the fixation hole to fixedly couple the DVS implant anchor to a skull of the subject.

Clause 11. The DVS implant anchor according to any one of Clauses 1-10, wherein the body is formed from a material selected from a polymer, a metal, a biologic, or a resorbable material.

Clause 12. The DVS implant anchor according to any one of Clauses 1-11, wherein the body is formed via blow molding, compression molding, injection molding, casting, machining, or 3D printing.

Clause 13. A surgical method for coupling a dural venous sinus (DVS) implant anchor, the method comprising: positioning the DVS implant anchor within a cranial hole in a skull of a subject; coupling the DVS implant anchor to the skull via an adjustment hole defined in a first portion of a body of the DVS implant anchor; and adjusting a DVS implant aperture disposed in a second portion of the body of the DVS implant anchor with respect to a dural venous sinus of the subject.

Clause 14. The surgical method according to Clause 13, further comprising drilling the cranial hole in the skull of a subject.

Clause 15. The surgical method according to any one of Clauses 13-14, wherein drilling the cranial hole comprises drilling a DVS burr hole.

Clause 16. The surgical method according to any one of Clauses 13-15, further comprising: measuring a depth of the cranial hole; and selecting the DVS implant anchor from a kit containing a plurality of different sized DVS implant anchor, wherein the selected DVS implant anchor corresponds in size to the depth of the cranial hole.

Clause 17. The surgical method according to any one of Clauses 13-16, further comprising placing an adhesive or conformal fibrous sponge-like material pad on a bottom of the DVS implant anchor.

Clause 18. The surgical method according to any one of Clauses 13-17, wherein adjusting the DVS implant aperture comprises translating the DVS implant aperture via a slot of the adjustment hole in one or more directions.

Clause 19. The surgical method according to any one of Clauses 13-17, wherein adjusting the DVS implant aperture comprises rotating the DVS implant aperture about a first fastener secured to the skull of the subject.

Clause 20. The surgical method according to any one of Clauses 13-19, further comprising securing the DVS implant anchor to the skull of the subject via a fixation hole defined in the first portion of the body of the DVS implant anchor.

Clause 21. The surgical method according to any one of Clauses 13-20, wherein securing the DVS implant anchor comprises advancing a second fastener into the skull of the subject until a head of the first fastener holds the DVS implant anchor against the skull of the subject.

Clause 22. An assembly, comprising: a DVS implant driver comprising a first end spaced apart from a second end; and a DVS implant comprising: a DVS implant body defined by an internal surface and an external surface, the DVS implant body shaped to receive the second end of the DVS implant driver such that the second end of the DVS implant driver abuts the internal surface, and one or more threads disposed on the external surface.

Clause 23. The assembly according to Clause 22, wherein the one or more threads disposed on the external surface of the DVS implant body are configured to threadedly engage with the threaded portion of the DVS implant anchor of Clause 7.

Clause 24. The assembly according to any one of Clauses 22-23, wherein the DVS implant driver further comprises a finger grip disposed on the first end.

Clause 25. The assembly according to any one of Clauses 22-24, wherein the finger grip comprises a plurality of cylindrical protrusions extending radially from the finger grip.

Clause 26. The assembly according to any one of Clauses 22-25, wherein the DVS implant driver further comprises: a first cylindrical protrusion extending from the first end, the first cylindrical protrusion defining a blood flow outlet; a second cylindrical protrusion extending from the second end, the second cylindrical protrusion defining a blood flow inlet; and a blood flow lumen extending through the DVS implant driver from the blood flow outlet of the first cylindrical protrusion to blood flow inlet of the second cylindrical protrusion.

Clause 27. The assembly according to any one of Clauses 22-26, wherein the second cylindrical protrusion functioning as a needle configured to penetrate a dura of a subject when the assembly is coupled to the DVS implant anchor according to any one of Clauses 1-12.

Clause 28. The assembly according to any one of Clauses 22-27, wherein the blood flow inlet is shaped and sized to accommodate a predetermined minimum or maximum cerebrospinal (CSF) flow rate and/or a predetermined pressure.

Clause 29. The assembly according to any one of Clauses 22-28, wherein the external surface of the DVS implant body concentrically surrounds the second cylindrical protrusion of the DVS implant driver to form a CSF outlet tip.

Clause 30. The assembly according to any one of Clauses 22-29, wherein the CSF outlet tip is curved to point into or against a blood flow of a DVS of a subject when the assembly is coupled to the DVS implant anchor according to any one of Clauses 1-12.

Clause 31. The assembly according to any one of Clauses 22-30, wherein the DVS implant driver is removable from the DVS implant after the DVS implant is coupled to the DVS implant anchor according to any one of Clauses 1-12.

Clause 32. The assembly according to any one of Clauses 22-31, wherein the DVS implant is configured to be coupled to a CSF pressure and flow control (PFC) device that is insertable within the DVS implant after removal of the DVS implant driver.

Clause 33. The assembly according to any one of Clauses 22-32, further comprising the PFC device.

Clause 34. The assembly according to any one of Clauses 22-33, wherein the PFC device comprises a CSF inlet, a CSF outlet, and an integrated pump reservoir mechanism.

Clause 35. The assembly according to any one of Clauses 22-34, wherein the PFC device further comprises: a first CSF flow lumen fluidly coupled to and extending between a tip and a central portion of the CSF inlet; a mechanical device chamber fluidly coupled to the first CSF flow lumen, the mechanical device chamber comprising a mechanical device configured to controllably prevent fluid flow through the mechanical device chamber; and a second CSF flow lumen defined within the CSF outlet and fluidly coupled to the mechanical device chamber.

Clause 36. The assembly according to any one of Clauses 22-35, wherein the mechanical device is selected from the group comprising a ball valve, a slit valve, and a pinch valve.

Clause 37. The assembly according to any one of Clauses 22-36, wherein the CSF inlet is fluidly couplable to a CSF source tube extends from a CSF source.

Clause 38. A method, comprising: inserting the assembly according to any one of Clauses 22-31 into the DVS implant anchor according to any one of Clauses 1-12; removing the DVS implant driver from the DVS implant; and inserting the PFC device according to any one of Clauses 33-37.

Clause 39. The method of Clause 38, further comprising: inserting a CSF source tube into a CSF source; and coupling the CSF inlet to the CSF source tube.

Clause 40. A DVS implant device alignment assembly, comprising: a procedure guide instrument including an upper surface, a lower surface, and one or more locking members for securing the procedure guide instrument to a subject's skull, an aperture formed in the procedure guide instrument and axially extending through the upper surface and the lower surface; and a plurality of locking adjustment arms slidably and lockingly positioned relative to the procedure guide instrument, each of the locking adjustment arms having a positioning element, optionally a pin, extending in a direction transverse to the upper surface of the procedure guide instrument.

Clause 41. The DVS implant device alignment assembly of Clause 40, wherein the locking adjustment arms are circumferential arranged about the aperture and slidable in a radial direction along the upper surface of the procedure guide instrument.

Clause 42. The DVS implant device alignment assembly of any one of Clauses 40-41, wherein one or more of the pins have a diameter different from a diameter of the other pins.

Clause 43. The DVS implant device alignment assembly of any one of Clauses 40-42, wherein one or more of the pins have a color different from a color of the other pins.

Clause 44. The DVS implant device alignment assembly of any one of Clauses 40-43, wherein the procedure guide instrument includes a plurality of navigation components configured to communicate with an external electronic or optical device.

Clause 45. The DVS implant device alignment assembly of any one of Clauses 40-44 further comprising: a probe guide positionable over the aperture of the procedure guide instrument, the probe guide including a plurality of legs extending in a radial direction relative to the aperture, each leg having a hole formed therein for receiving a corresponding one of the pins, a channel extending axially through the probe guide; and a navigated probe tip insertable in an axial direction through the channel, an end of the navigated probe tip marking a location to be drilled.

Clause 46. The DVS implant device alignment assembly of any one of Clauses 40-45, further comprising: a burr guide positionable over the aperture of the procedure guide instrument, the burr guide including a plurality of legs extending in a radial direction relative to the aperture, each leg having a hole formed therein for receiving a corresponding one of the pins, a circular channel extending axially through the burr guide for receiving a drilling device.

Clause 47. The DVS implant device alignment assembly of any one of Clauses 40-46, further comprising: a needle guide positionable over the aperture of the procedure guide instrument, the needle guide including a plurality of legs extending in a radial direction relative to the aperture, each leg having a hole formed therein for receiving a corresponding one of the pins, a channel extending axially through the needle guide; a safety stop positionable on an upper surface of the needle guide opposite the aperture, the safety stop having a shape corresponding to a shape of the needle guide, the safety stop having a thickness between 1 mm and 2 mm; and a needle axially extending through the channel formed in the needle guide and the safety stop, the needle including a needle stop abutting against a surface of the safety stop opposite the needle guide when lowered onto the safety stop.

Clause 48. The DVS implant device alignment assembly of any one of Clauses 40-47, wherein the needle guide has a plurality channels formed therein and arranged in a spaced apart linear array and the needle is positionable within each of the plurality of channels.

Clause 49. The DVS implant device alignment assembly of any one of Clauses 40-48, further comprising: an implant guide positionable over the aperture of the procedure guide instrument, the implant guide including a plurality of legs extending in a radial direction relative to the aperture, each leg having a hole formed therein for receiving a corresponding one of the pins, a channel extending axially through the implant guide; an applicator stick extending through the channel of the implant guide; and a dura stiffening pad removably adhered to an end of the applicator stick.

Clause 50. The DVS implant device alignment assembly of any one of Clauses 40-49, further comprising an implant assembly, the implant assembly comprising: an implant insertion tool extending through the channel of the implant guide; an implant flex tube extending through the implant insertion tool; and an implant provided at an end of the implant flex tube.

Clause 51. A surgical method for the placement of a DVS implant device on a DVS, comprising: securing a procedure guide instrument on a subject's skull, the procedure guide instrument including an upper surface, a lower surface, and one or more locking members for securing the procedure guide instrument to a subject's skull, an aperture formed in the procedure guide instrument and axially extending through the upper surface and the lower surface; slidingly positioning a plurality of locking adjustment arms relative to the procedure guide instrument, each of the locking adjustment arms having a positioning element, optionally a pin, extending in a direction transverse to the upper surface of the procedure guide instrument; positioning a probe guide over the aperture of the procedure guide instrument, the probe guide including a plurality of legs extending in a radial direction relative to the aperture, each leg having a hole formed therein for receiving a corresponding one of the pins, a channel extending axially through the probe guide; inserting a navigated probe tip in an axial direction through the channel of the probe guide; locking the plurality of locking adjustment arms in position relative to the procedure guide instrument; and marking a location to be drilled with an end of the navigated probe tip.

Clause 52. The surgical method of Clause 51, further comprising: removing the probe guide and the navigated probe tip from the plurality of locking adjustment arms; positioning a burr guide over the aperture of the procedure guide instrument, the burr guide including a plurality of legs extending in a radial direction relative to the aperture, each leg having a hole formed therein for receiving a corresponding one of the pins, a circular channel extending axially through the burr guide for receiving a drilling device; and drilling a burr hole into the subject's skull to expose a dura above the DVS.

Clause 53. The surgical method of any one of Clauses 51-52, further comprising: removing the burr guide from the plurality of locking adjustment arms; positioning a needle guide over the aperture of the procedure guide instrument, the needle guide including a plurality of legs extending in a radial direction relative to the aperture, each leg having a hole formed therein for receiving a corresponding one of the pins, a channel extending axially through the needle guide; positioning a safety stop on an upper surface of the needle guide opposite the aperture, the safety stop having a shape corresponding to a shape of the needle guide, the safety stop having a thickness between 1 mm and 2 mm; and extending a needle through the channel formed in the needle guide and the safety stop; adjusting a needle stop on the needle such that an end of the needle contacts an upper surface of the dura when an end of the needle stop contacts a surface of the safety stop.

Clause 54. The surgical method of any one of Clauses 51-53, further comprising: removing the safety stop; extending the needle through the channel formed in the needle guide such that the needle extends through the dura; removing the needle; and determining whether blood is present in the channel.

Clause 55. The surgical method of any one of Clauses 51-54, further comprising: extending the needle through two or more adjacent channels formed in the needle guide; removing the needle from the adjacent channels; and determining whether blood is present in the adjacent channels.

Clause 56. The surgical method of any one of Clauses 51-55, further comprising: positioning an implant guide over the aperture of the procedure guide instrument, the implant guide including a plurality of legs extending in a radial direction relative to the aperture, each leg having a hole formed therein for receiving a corresponding one of the pins, a channel extending axially through the implant guide, the alignment of the channel relative to the aperture corresponding to the presence of blood in the channels and the adjacent channels of the needle guide.

Clause 57. The surgical method of any one of Clauses 51-56, further comprising: extending an applicator stick through the channel of the implant guide, a dura stiffening pad removably adhered to an end of the applicator stick; removing the applicator stick from the implant guide; and leaving the dura stiffening pad on the dura.

Clause 58. The surgical method of any one of Clauses 51-57, further comprising: extending an implant insertion tool, an implant flex tube, and an implant through the channel of the implant guide; and removing the implant insertion tool from the implant guide leaving the implant fixed to the dura stiffening pad and the implant flex tube extending from the implant.

Clause 59. The surgical method of any one of Clauses 51-58, further comprising: positioning an implant lock within the burr hole to fix the implant and the dura stiffening pad within the burr hole.

Clause 60. The surgical method of any one of Clauses 51-59, wherein the implant lock is a flexible member having engaging features at opposite ends thereof for engaging the subject's skull and maintaining the position of the implant lock within the burr hole.

Clause 61. The surgical method of any one of Clauses 51-60, further comprising: bending the implant flex tube to extend out of the burr hole and along an outer surface of the subject's skull; and positioning a protective cap over the burr hole, the burr hole having a port formed therein, the implant flex tube extending through the port.

Clause 62. An apparatus of any one of Clauses 1-61 substantially as shown and described herein.

Clause 63. An assembly any one of Clauses 1-61 substantially as shown and described herein.

Clause 64. A device any one of Clauses 1-61 substantially as shown and described herein.

Clause 65. A method of inserting an assembly any one of Clauses 1-61 substantially as shown and described herein.

The invention claimed is:

1. A surgical method for coupling a dural venous sinus (DVS) implant anchor, the method comprising:

positioning the DVS implant anchor within a cranial hole in a skull of a subject;

coupling the DVS implant anchor to the skull via an adjustment hole defined in a first portion of a body of the DVS implant anchor; and adjusting the location of a DVS implant aperture disposed in a second portion of the body of the DVS implant anchor with respect to a dural venous sinus of the subject.

2. The surgical method according to claim 1, further comprising:

drilling the cranial hole in the skull of a subject, wherein drilling the cranial hole comprises drilling a DVS burr hole;

measuring a depth of the cranial hole; and selecting the DVS implant anchor from a kit containing a plurality of different sized DVS implant anchor, wherein the selected DVS implant anchor corresponds in size to the depth of the cranial hole.

3. The surgical method according to claim 1, further comprising placing an adhesive or conformal fibrous sponge-like material pad on a bottom of the DVS implant anchor.

4. The surgical method according to claim 1, wherein adjusting the DVS implant aperture comprises translating the DVS implant aperture via a slot of the adjustment hole in one or more directions.

5. The surgical method according to claim 1, wherein:

adjusting the DVS implant aperture comprises rotating the DVS implant aperture about a first fastener secured to the skull of the subject further comprising securing the DVS implant anchor to the skull of the subject via a fixation hole defined in the first portion of the body of the DVS implant anchor.

6. The surgical method according to claim 5, wherein securing the DVS implant anchor comprises advancing a second fastener into the skull of the subject until a head of the first fastener holds the DVS implant anchor against the skull of the subject.

* * * * *